United States Patent
Kabasawa et al.

(10) Patent No.: US 12,317,744 B2
(45) Date of Patent: May 27, 2025

(54) COMPOUND HAVING A FUSED-AZOLE RING STRUCTURE AND ORGANIC ELECTROLUMINESCENT ELEMENT

(71) Applicant: Hodogaya Chemical Co., Ltd., Tokyo (JP)

(72) Inventors: Naoaki Kabasawa, Tokyo (JP); Keigo Naito, Tokyo (JP); Taeyoung Kim, Tokyo (JP)

(73) Assignee: Hodogaya Chemical Co., Ltd., Tokyo (JP)

( * ) Notice: Subject to any disclaimer, the term of this patent is extended or adjusted under 35 U.S.C. 154(b) by 549 days.

(21) Appl. No.: 16/315,802

(22) PCT Filed: Jul. 6, 2017

(86) PCT No.: PCT/JP2017/024779
§ 371 (c)(1),
(2) Date: Jan. 7, 2019

(87) PCT Pub. No.: WO2018/008718
PCT Pub. Date: Jan. 11, 2018

(65) Prior Publication Data
US 2019/0252621 A1    Aug. 15, 2019

(30) Foreign Application Priority Data

Jul. 7, 2016  (JP) ................. 2016-134799

(51) Int. Cl.
*H10K 85/60*  (2023.01)
*C07D 263/57*  (2006.01)
(Continued)

(52) U.S. Cl.
CPC ......... *H10K 85/657* (2023.02); *C07D 263/57* (2013.01); *C07D 413/04* (2013.01);
(Continued)

(58) Field of Classification Search
None
See application file for complete search history.

(56) References Cited

U.S. PATENT DOCUMENTS

| 2,807,616 A | 9/1957 | Falco et al. |
| 7,514,159 B2 | 4/2009 | Nakamura |

(Continued)

FOREIGN PATENT DOCUMENTS

| CN | 1575069 A | 2/2005 |
| CN | 105294670 A | 2/2016 |

(Continued)

OTHER PUBLICATIONS

Machine-translated English document of JP 2016058205 A, Iijima Takayuki, Apr. 21, 2016 (Year: 2016).*

(Continued)

*Primary Examiner* — Seokmin Jeon
(74) *Attorney, Agent, or Firm* — Troutman Pepper Locke LLP; James E. Armstrong, IV; Nicolas J. DiCeglie, Jr.

(57) ABSTRACT

To provide an organic compound having a high electron injection/transport performances, an excellent hole blocking ability, and a stable thin-film state, as a material for organic electroluminescent devices with high efficiency and high durability, and also to provide an organic electroluminescent device having a high efficiency and high durability by using the compound.

An organic electroluminescent device comprising a pair of electrodes, and one or more organic layers sandwiched between the pair of electrodes, wherein the compound having a fused-azole ring structure of the general formula (1) is used as a constituent material of at least one organic layer.

(Continued)

- 9 CATHODE
- 8 ELECTRON INJECTION LAYER
- 7 ELECTRON TRANSPORT LAYER
- 6 HOLE BLOCKING LAYER
- 5 LIGHT EMITTING LAYER
- 4 HOLE TRANSPORT LAYER
- 3 HOLE INJECTION LAYER
- 2 TRANSPARENT ANODE
- 1 GLASS SUBSTRATE

[Chemical Formula 1]

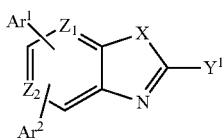

(1)

6 Claims, 1 Drawing Sheet

(51) Int. Cl.
| | |
|---|---|
| C07D 413/04 | (2006.01) |
| C07D 413/10 | (2006.01) |
| C07D 413/14 | (2006.01) |
| C07D 417/10 | (2006.01) |
| C07D 471/04 | (2006.01) |
| C07D 471/10 | (2006.01) |
| C09K 11/06 | (2006.01) |
| H10K 50/00 | (2023.01) |
| H10K 50/11 | (2023.01) |
| H10K 50/16 | (2023.01) |
| H10K 50/17 | (2023.01) |
| H10K 50/18 | (2023.01) |
| H10K 101/10 | (2023.01) |

(52) U.S. Cl.
CPC ......... *C07D 413/10* (2013.01); *C07D 413/14* (2013.01); *C07D 417/10* (2013.01); *C07D 471/04* (2013.01); *C07D 471/10* (2013.01); *C09K 11/06* (2013.01); *H10K 50/00* (2023.02); *H10K 85/615* (2023.02); *H10K 85/622* (2023.02); *H10K 85/624* (2023.02); *H10K 85/626* (2023.02); *H10K 85/654* (2023.02); *H10K 85/6572* (2023.02); *H10K 85/6574* (2023.02); *C09K 2211/1018* (2013.01); *H10K 50/11* (2023.02); *H10K 50/16* (2023.02); *H10K 50/171* (2023.02); *H10K 50/18* (2023.02); *H10K 2101/10* (2023.02)

(56) References Cited

U.S. PATENT DOCUMENTS

| | | | |
|---|---|---|---|
| 8,119,814 | B2 | 2/2012 | Shin et al. |
| 8,883,833 | B2 | 11/2014 | Singh et al. |
| 9,005,776 | B2 | 4/2015 | Yokoyama et al. |
| 9,966,538 | B2 | 5/2018 | Choi et al. |
| 10,069,082 | B2 | 9/2018 | Ren et al. |
| 10,193,072 | B2 | 1/2019 | Jeong et al. |
| 11,316,114 | B2 | 4/2022 | Cho et al. |
| 2002/0121860 | A1* | 9/2002 | Seo .............................. 313/506 |
| 2004/0251467 | A1 | 12/2004 | Nakamura |
| 2006/0134460 | A1* | 6/2006 | Kondakova .................. 428/690 |
| 2008/0093981 | A1* | 4/2008 | Nakamura .................... 313/504 |
| 2008/0220286 | A1 | 9/2008 | Qiu et al. |
| 2009/0130076 | A1 | 5/2009 | Singh et al. |
| 2009/0130077 | A1 | 5/2009 | Singh et al. |
| 2009/0149649 | A1 | 6/2009 | Shin et al. |
| 2009/0264405 | A1* | 10/2009 | Ali .......................... 514/210.18 |
| 2010/0190994 | A1 | 7/2010 | Lee et al. |
| 2012/0012831 | A1 | 1/2012 | Yokoyama et al. |
| 2012/0207729 | A1 | 8/2012 | Singh et al. |
| 2014/0239269 | A1 | 8/2014 | Jeong et al. |
| 2014/0275553 | A1 | 9/2014 | Singh et al. |
| 2016/0181544 | A1 | 6/2016 | Choi et al. |
| 2017/0148996 | A1 | 5/2017 | Ren et al. |
| 2017/0244049 | A1 | 8/2017 | Aspuru-Guzik et al. |
| 2018/0040829 | A1* | 2/2018 | Lee ..................... H01L 51/0071 |
| 2019/0067593 | A1* | 2/2019 | Cho .................... H01L 51/0067 |

FOREIGN PATENT DOCUMENTS

| | | | | |
|---|---|---|---|---|
| CN | 105418357 | A | | 3/2016 |
| CN | 105481845 | A | | 4/2016 |
| CN | 108699054 | A | | 10/2018 |
| EP | 2409974 | A1 | | 1/2012 |
| GB | 2357296 | A | * 6/2001 | ............... C10L 1/22 |
| JP | 49-61195 | A | | 6/1974 |
| JP | S58-176275 | A | | 10/1983 |
| JP | H1-294788 | A | | 11/1989 |
| JP | H04-146446 | A | | 5/1992 |
| JP | 2581589 | B2 | | 2/1997 |
| JP | 2005-289921 | A | | 10/2005 |
| JP | 2006-093673 | A | | 4/2006 |
| JP | 3820037 | B2 | | 9/2006 |
| KR | 10-2009-0059849 | A | | 6/2009 |
| KR | 10-1385216 | B1 | | 4/2014 |
| KR | 10-2014-0094408 | A | | 7/2014 |
| KR | 10-2015-0030294 | A | | 3/2015 |
| KR | 10-2015-0064442 | A | | 6/2015 |
| WO | 2008/117976 | A1 | | 10/2008 |
| WO | 2015/083948 | A1 | | 6/2015 |
| WO | 2015/175678 | A1 | | 11/2015 |
| WO | 2016/197353 | A1 | | 12/2016 |
| WO | 2017/078403 | A1 | | 5/2017 |
| WO | 2017/156698 | A1 | | 9/2017 |

OTHER PUBLICATIONS

English translation of KR 2014/0094408 A and the original KR 2014/0094408 A, Jeong Keun Park, Jul. 30, 2014 (Year: 2014).*
M. Luisa Gelmi et al. "Oxazol-5(4H)-ones Part 7. New Synthesis of Oxazolo[5,4-b]pyridines", J. Chem. Soc. Perkin Trans. 1992, pp. 701-705 (Year: 1992).*
Machine translated English version of JP 2016/119355 A, Shun Hamaguchi, Jun. 30, 2016 (Year: 2016).*
Minwoo Han et al. "Formation of Rigid Organic Nanotubes with Controlled Internal Cavity Based on Frustrated Aggregate Internal Rearrangement Mechanism", J. Phys. Chem. B, 2013, vol. 117, p. 7763-7770 (Year: 2013).*
Machine translated English version of JP 2005/289921 A, Koji Inoue et al., Oct. 20, 2005 (Year: 2005).*
Gelmi, M. Luisa et al. "Oxazol-5(4H)-ones. Part 7.' New Synthesis of Oxazolo[5,4-b]pyridines," Journal of the Chemical Society, Perkin Translations 1, Mar. 1992, No. 6, pp. 701-705 and a cover sheet.
International Search Report mailed Oct. 3, 2017, issued for PCT/JP2017/024779.
Office Action mailed May 25, 2021. issued for Corresponding Japanese Patent Application No. 2018-526435.
Office Action dated Jan. 21, 2021, issued for the corresponding Taiwanese Patent Application No. 106122766 and Japanese translation thereof.
V. Sridharan et al., "A novel synthetic route for the synthesis of 4,6-diaryl-2-methyl-1,3-benzoxazoles", Journal of Heterocyclic Chemistry, Nov. 1, 2005, pp. 1321-1330. (cited in the Dec. 4, 2019 Search Report issued for EP17824321.8).
S. K. Alla et al., "Organocatalytic Syntheses of Benzoxazoles and Benzothiazoles using Aryl Iodide and Oxone via C-H Functionalization and C-O/S Bond Formation", Journal of Organic Chemistry, vol. 79, No. 16, Jul. 29, 2014, pp. 7502-7511. (cited in the Dec. 4, 2019 Search Report issued for EP17824321.8).
V. Kavala et al., "One-Pot Tandem Synthesis of 2-Arylbenzoxazole Derivatives via Copper-Catalyzed C-N and C-O Bond Formation", Advanced Synthesis & Catalysis, vol. 354, No. 11-12, Aug. 13, 2012, pp. 2229-2240. (cited in the Dec. 4, 2019 Search Report issued for EP17824321.8).
N. Park et al., "Synthesis of Benzothiazoles through Copper-Catalyzed One-Pot Three-Component Reactions with Use of Sodium Hydrosulfide as a Sulfur Surrogate", European Journal of Organic

(56) References Cited

OTHER PUBLICATIONS

Chemistry, vol. 2012, No. 10, Feb. 16, 2012, pp. 1984-1993. (cited in the Dec. 4, 2019 Search Report issued for EP17824321.8).

D. K. Swamy et al., "Studies on synthesis, antibacterial screening and the mass fragmentation of 1-(4,6-dimethylbenzothiazolyl)-3,5-disubstituted-1,2,4-1H-triazoles", J. Chem. Pharm. Res, 2010, 2(3), Jan. 1, 2010, pp. 411-416. (cited in the Dec. 4, 2019 Search Report issued for EP17824321.8).

A. Reiser et al., "Fluorescence of Aromatic Benzoxazole Derivatives", Journal of the American Chemical Society, American Chemical Society, US, vol. 94, No. 7, Apr. 5, 1972, pp. 2414-2421. (cited in the Dec. 4, 2019 Search Report issued for EP17824321.8).

A. Zaletova et al., "Synthesis of 4,6-Disubstituted-2-(1H-indol-3-yl)benzothiazoles", Collection Symposium Series (Xiiith Symposium On Chemistry of Nucleic Acid Components Spindleruv Mlyn, Czech Republic; Sep. 3-9, 2005, vol. 69, No. 2, Jan. 1, 2004, pp. 453-460. (cited in the Dec. 4, 2019 Search Report issued for EP17824321.8).

Supplementary European Search Report dated Dec. 4, 2019, issued for the European patent application No. 17824321.8.

Clark et al. "2-(Substituted phenyl)oxazolo[4,5-b]pyridines and 2-(Substituted phenyl)oxazolo[5,4-b]pyridines as Nonacidic Antiinflammatory Agents", Journal of Medicinal Chemistry, vol. 21, No. 11, (1978).

Office Action issued in Korean Patent Application No. KR 10-2019-7002857 (with Japanese translation), dated Nov. 18, 2021.

Japanese Examiner's Report issued in Japanese Patent Application No. JP 2018-526435, dated Apr. 6, 2022.

Xu et al. "Synthesis of 2-Arylbenzothiazoles by Copper-Catalyzed One-Pot Three-Component Reactions in Water", Journal of Heterocyclic Chemistry, vol. 53, pp. 1207-1213, (2015).

STN Registry, CAS No. 134072-13-2 (1907).

Decision of Refusal issued in Korean Patent Application No. KR 10-2019-7002857, dated May 20, 2022 (with Japanese translation).

Office Action issued in corresponding Chinese Patent Application No. CN 201780041812.2, dated Nov. 14, 2022, with Japanese translation.

* cited by examiner

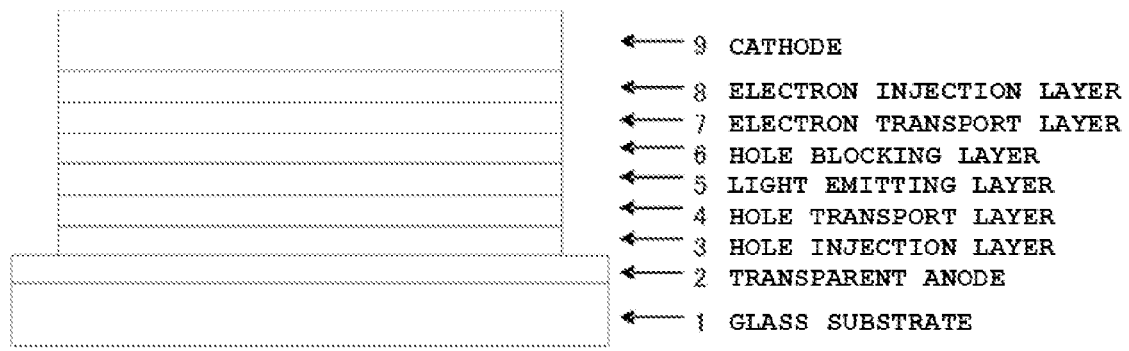

COMPOUND HAVING A FUSED-AZOLE RING STRUCTURE AND ORGANIC ELECTROLUMINESCENT ELEMENT

TECHNICAL FIELD

The present invention relates to compounds suitable for an organic electroluminescent device (hereinafter referred to as organic EL devices) which is a preferred self-luminous device for various display devices, and relates to the organic electroluminescent device. Specifically, this invention relates to compounds having a fused-azole ring structure, and organic EL devices using the compounds.

BACKGROUND ART

The organic EL device is a self-luminous device and has been actively studied for their brighter, superior visibility and the ability to display clearer images in comparison with liquid crystal devices.

In 1987, C. W. Tang and colleagues at Eastman Kodak developed a laminated structure device using materials assigned with different roles, realizing practical applications of an organic EL device with organic materials. These researchers laminated an electron-transporting phosphor and a hole-transporting organic substance, and injected both charges into a phosphor layer to cause emission in order to obtain a high luminance of 1,000 cd/m$^2$ or more at a voltage of 10 V or less (refer to PTLs 1 and 2, for example).

To date, various improvements have been made for practical applications of the organic EL device. Various roles of the laminated structure are further subdivided to provide an electroluminescence device that includes an anode, a hole injection layer, a hole transport layer, a light emitting layer, an electron transport layer, an electron injection layer, and a cathode successively formed on a substrate, and high efficiency and durability have been achieved by the electroluminescence device (refer to NPL 1, for example).

Further, there have been attempts to use triplet excitons for further improvements of luminous efficiency, and the use of a phosphorescence emitting compound has been examined (refer to NPL 2, for example).

Devices that use light emission caused by thermally activated delayed fluorescence (TADF) have also been developed. In 2011, Adachi et al. at Kyushu University, National University Corporation realized 5.3% external quantum efficiency with a device using a thermally activated delayed fluorescent material (refer to NPL 3, for example).

The light emitting layer can be also fabricated by doping a charge transporting compound generally called a host material, with a fluorescent compound, a phosphorescence-emitting compound, or a delayed fluorescent-emitting material. As described in the NPL, the selection of organic materials in an organic EL device greatly influences various device characteristics such as efficiency and durability (refer to NPL 2, for example).

In an organic EL device, charges injected from both electrodes recombine in a light emitting layer to cause emission. What is important here is how efficiently the hole and electron charges are transferred to the light emitting layer.

The probability of hole-electron recombination can be improved by improving electron injectability, electron mobility, and hole blocking performance of blocking injected holes from the anode, and high luminous efficiency can be obtained by confining excitons generated in the light emitting layer. The role of an electron transport material is therefore important, and there is a need for a hole transport material that has high electron injectability, high electron mobility, high hole blocking performance, and high durability to holes.

Heat resistance and amorphousness of the materials are also important with respect to the lifetime of the device. The materials with low heat resistance cause thermal decomposition even at a low temperature by heat generated during the drive of the device, which leads to the deterioration of the materials. The materials with low amorphousness cause crystallization of a thin film even in a short time and lead to the deterioration of the device. The materials in use are therefore required to have characteristics of high heat resistance and satisfactory amorphousness.

A typical light-emitting material, tris(8-hydroxyquinoline)aluminium (hereinafter referred to as Alq$_3$) generally serves also as an electron transporting material, but electron transfer is slow, and the work function is 5.6 eV, so it could not be said that the material may have a hole blocking ability.

Compounds having a benzotriazole structure are proposed as compounds improved in the characteristics such as electron injection characteristic and mobility (refer to PTL 3, for example). While the devices using these compounds for the electron transport layer have been improved in luminous efficiency and the like, the improvements are still insufficient. Further lower driving voltage and higher luminous efficiency are therefore needed.

As an electron transporting material having an excellent hole blocking ability, 3-(4-biphenylyl)-4-phenyl-5-(4-t-butylphenyl)-1,2,4-triazole (hereinafter referred to as TAZ) is proposed (refer to PTL 4, for example).

TAZ has a large work function of 6.6 eV and has a high hole blocking ability, and is therefore used as an electron transportable hole blocking layer to be laminated on the cathode side of the fluorescent light emitting layer or the phosphorescence emitting layer formed through vacuum evaporation, coating or the like, and contributes toward increasing the efficiency of organic EL devices (refer to NPL 4, for example).

However, TAZ has a serious problem in that its electron transportability is low, and it must be combined with an electron transporting material having a higher electron transportability in using it for constructing organic EL devices (refer to NPL 5, for example).

BCP has a large work function of 6.7 eV and has a high hole blocking ability, but has a low glass transition point (Tg) of 83° C., and therefore its film stability is poor, and accordingly, it could not be said that BCP may fully function as a hole blocking layer.

All the materials are insufficient in the stability of films thereof or insufficient in the function thereof of blocking holes. For improving the characteristics of organic EL devices, desired are organic compounds showing an excellent electron injecting/transporting performance, an excellent hole blocking ability and showing a high stability as thin films.

CITATION LIST

Patent Literature

PTL 1: JP-A-8-048656
PTL 2: Japanese Patent No. 3194657
PTL 3: WO2013/054764
PTL 4: Japanese Patent No. 2734341
PTL 5: JP-A-2010-83862
PTL 6: WO2015/038503

Non Patent Literature

NPL 1: The Japan Society of Applied Physics, 9th Lecture Preprints, pp. 55 to 61 (2001)
NPL 2: The Japan Society of Applied Physics, 9th Lecture Preprints, pp. 23 to 31 (2001)
NPL 3: Appl. Phys. Let., 98, 083302 (2011)
NPL 4: Preprint in 28p-A-6 Lecture of the 50th Applied Physics-Associated Joint Lecture Presentation, p. 1413 (2003)
NPL 5: The organic Molecule/Bioelectronics Section Committee of the Japan Society of Applied Physics. 2000, 11 (1), 13-19
NPL 6: J. Org. chcm., 71, 1802(2006)
NPL 7: J. Org. chcm., 79, 6310(2014)

SUMMARY OF INVENTION

Technical Problem

An object of the invention is to provide an organic compound which shows an excellent electron injecting/transporting performance, has a hole blocking ability and shows a high stability as a thin film, that is, having excellent characteristics as a material for organic electroluminescent device having high efficiency and high durability; and to provide an organic EL device comprising the compound and having high efficiency and high durability.

Physical properties of the organic compound to be provided by the present invention include (1) a good electron injection characteristic, (2) large electron mobility, (3) an excellent hole blocking ability, and is (4) stable as a thin film and (5) excellent in heat resistance. Physical properties of the organic EL device to be provided by the present invention include (1) high luminous efficiency and high power efficiency, (2) low turn on voltage, (3) low actual driving voltage, and (4) a long lifetime.

Solution to Problem

For attaining the above-mentioned object, the present inventors have noted that, the nitrogen atom of an electrophilic fused-azole ring has the ability to coordinate with a metal and is excellent in heat resistance, and have planned and chemically synthesized compounds having a fused-azole ring structure; and using the compound, the inventors have produced various organic electroluminescent devices experimentally, and have assiduously investigated and evaluated the characteristics of the devices and, as a result, have completed the present invention.

1) A compound of the following general formula (1) having a fused-azole ring structure.

[Chemical Formula 1]

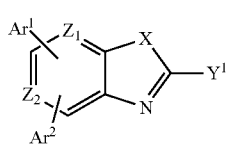

(1)

In the formula, $Ar^1$ and $Ar^2$ may be the same or different, and each represents a hydrogen atom, a deuterium atom, a substituted or unsubstituted aromatic hydrocarbon group, a substituted or unsubstituted aromatic heterocyclic group, a substituted or unsubstituted condensed polycyclic aromatic group, or alkyl. $Y^1$ represents a substituted or unsubstituted aromatic hydrocarbon group, a substituted or unsubstituted aromatic heterocyclic group, a substituted or unsubstituted condensed polycyclic aromatic group, or alkyl. X represents an oxygen atom or a sulfur atom. $Z_1$ and $Z_2$ may be the same or different, and each represents a carbon atom or a nitrogen atom.

2) The compound having a fused-azole ring structure of 1), wherein the compound is represented by the following general formula (2).

[Chemical Formula 2]

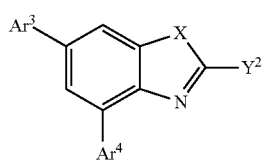

(2)

In the formula, $Ar^3$ and $Ar^4$ may be the same or different, and each represents a hydrogen atom, a deuterium atom, a substituted or unsubstituted aromatic hydrocarbon group, a substituted or unsubstituted aromatic heterocyclic group, a substituted or unsubstituted condensed polycyclic aromatic group, or a substituted or unsubstituted alkyl. $Y^2$ represents a substituted or unsubstituted aromatic hydrocarbon group, a substituted or unsubstituted aromatic heterocyclic group, a substituted or unsubstituted condensed polycyclic aromatic group, or alkyl. X represents an oxygen atom or a sulfur atom.

3) The compound having a fused-azole ring structure of 1), wherein the compound is represented by the following general formula (3).

[Chemical Formula 3]

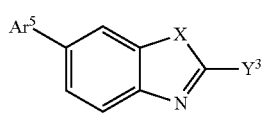

(3)

In the formula, $Ar^5$ represents a hydrogen atom, a deuterium atom, a substituted or unsubstituted aromatic hydrocarbon group, a substituted or unsubstituted aromatic heterocyclic group, or a substituted or unsubstituted condensed polycyclic aromatic group. $Y^3$ represents a substituted or unsubstituted aromatic hydrocarbon group, a substituted or unsubstituted aromatic heterocyclic group, a substituted or unsubstituted condensed polycyclic aromatic group, or alkyl. X represents an oxygen atom or a sulfur atom.

4) The compound having a fused-azole ring structure of 1), wherein the compound is represented by the following general formula (4).

[Chemical Formula 4]

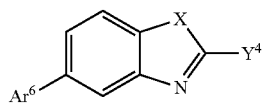

(4)

In the formula, Ar$^6$ represents a hydrogen atom, a deuterium atom, a substituted or unsubstituted aromatic hydrocarbon group, a substituted or unsubstituted aromatic heterocyclic group, or a substituted or unsubstituted condensed polycyclic aromatic group. Y$^4$ represents a substituted or unsubstituted aromatic hydrocarbon group, a substituted or unsubstituted aromatic heterocyclic group, a substituted or unsubstituted condensed polycyclic aromatic group, or alkyl. X represents an oxygen atom or a sulfur atom.

5) The compound having a fused-azole ring structure of 1), wherein the compound is represented by the following general formula (5).

[Chemical Formula 5]

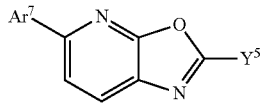

(5)

In the formula, Ar$^7$ represents a hydrogen atom, a deuterium atom, a substituted or unsubstituted aromatic hydrocarbon group, a substituted or unsubstituted aromatic heterocyclic group, or a substituted or unsubstituted condensed polycyclic aromatic group. Y$^5$ represents a substituted or unsubstituted aromatic hydrocarbon group, a substituted or unsubstituted aromatic heterocyclic group, or a substituted or unsubstituted condensed polycyclic aromatic group.

6) The compound having a fused-azole ring structure of 1), wherein the compound is represented by the following general formula (6).

[Chemical Formula 6]

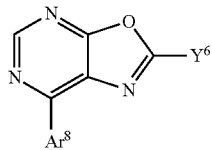

(6)

In the formula, Ar$^8$ represents a hydrogen atom, a deuterium atom, a substituted or unsubstituted aromatic hydrocarbon group, a substituted or unsubstituted aromatic heterocyclic group, or a substituted or unsubstituted condensed polycyclic aromatic group. Y$^6$ represents a substituted or unsubstituted aromatic hydrocarbon group, a substituted or unsubstituted aromatic heterocyclic group, or a substituted or unsubstituted condensed polycyclic aromatic group.

7) An organic electroluminescent device comprising a pair of electrodes, and one or more organic layers sandwiched between the pair of electrodes, wherein the compound having a fused-azole ring structure of any one of 1) to 6) is used as a constituent material of at least one organic layer.

8) The organic electroluminescent device of 7), wherein the organic layer using the compound having a fused-azole ring structure is an electron transport layer.

9) The organic electroluminescent device of 7), wherein the organic layer using the compound having a fused-azole ring structure is a hole blocking layer.

10) The organic electroluminescent device of 7), wherein the organic layer using the compound having a fused-azole ring structure is a light emitting layer.

11) The organic electroluminescent device of 7), wherein the organic layer using the compound having a fused-azole ring structure is an electron injection layer.

Specific examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by Y$^1$ to Y$^6$ and Ar$^1$ to Ar$^8$ in the general formulae (1) to (6) include aryl of 6 to 30 carbon atoms and heteroaryl of 2 to 20 carbon atoms, besides phenyl, biphenylyl, terphenylyl, naphthyl, anthracenyl, phenanthryl, fluorenyl, spirobifluorenyl, indenyl, pyrenyl, perylenyl, fluoranthenyl, triphenylenyl, pyridyl, pyrimidinyl, triazinyl, furyl, pyrrolyl, thienyl, quinolyl, isoquinolyl, benzofuranyl, benzothienyl, indolyl, carbazolyl, benzoxazolyl, benzothiazolyl, quinoxalinyl, benzoimidazolyl, pyrazolyl, dibenzofuranyl, dibenzothienyl, naphthyridinyl, phenanthrolinyl, acridinyl, and carbolinyl.

Specific examples of the "substituent" in the "substituted aromatic hydrocarbon group", the "substituted aromatic heterocyclic group", and the "substituted condensed polycyclic aromatic group" represented by Y$^1$ to Y$^6$ and Ar$^1$ to Ar$^8$ in the general formulae (1) to (6) include a deuterium atom; cyano; nitro; halogen atoms such as a fluorine atom, a chlorine atom, a bromine atom, and an iodine atom; linear or branched alkyloxys of 1 to 6 carbon atoms such as methyloxy, ethyloxy, and propyloxy; alkenyls such as vinyl and allyl; aryloxys such as phenyloxy and tolyloxy; arylalkyloxys such as benzyloxy and phenethyloxy; aromatic hydrocarbon groups or condensed polycyclic aromatic groups such as phenyl, biphenylyl, terphenylyl, naphthyl, anthracenyl, phenanthrenyl, fluorenyl, spirobifluorenyl, indenyl, pyrenyl, perylenyl, fluoranthenyl, and triphenylenyl; aromatic heterocyclic groups such as pyridyl, thienyl, furyl, pyrrolyl, quinolyl, isoquinolyl, benzofuranyl, benzothienyl, indolyl, carbazolyl, benzoxazolyl, benzothiazolyl, quinoxalinyl, benzoimidazolyl, pyrazolyl, dibenzofuranyl, dibenzothienyl, and carbolinyl. These substituents may be further substituted with the exemplified substituents above. These substituents may bind to each other to form a ring via a single bond, substituted or unsubstituted methylene, an oxygen atom, or a sulfur atom.

Specific examples of the "alkyl" represented by Y$^1$ to Y$^4$ in the general formulae (1) to (6) include methyl, ethyl, n-propyl, isopropyl, n-butyl, isobutyl, tert-butyl, n-pentyl, isopentyl, neopentyl, n-hexyl, cyclopentyl, cyclohexyl, 1-adamantyl, 2-adamantyl, vinyl, allyl, isopropenyl, and 2-butenyl.

The compounds having a fused-azole ring structure of the general formula (1), for preferred use in the organic EL device of the present invention, can be used as a constitutive material of an electron injection layer or an electron transport layer of an organic EL device. The compounds having a fused-azole ring structure of the general formula (1) have high electron mobility and are therefore preferred compounds as a material of a hole injection layer or an electron transport layer.

In the organic EL device of the present invention, materials for an organic EL device have excellent electron injection/transport performances, stability as a thin film, and durability. Therefore, compared with the conventional organic EL devices, electron transport efficiency to a light emitting layer from an electron transport layer is improved. As a result, luminous efficiency is improved, and also driving voltage is decreased, and thus, durability of the organic EL device can be improved.

Thus, an organic EL device having high efficiency, low driving voltage, and a long lifetime can be attained.

Advantageous Effects of Invention

The organic EL device of the present invention can achieve an organic EL device which can efficiently inject/transport electrons from an electron transport layer into a light emitting layer, and therefore has electron injection/transport performances, stability as a thin film, durability, high efficiency, low driving voltage, and a long lifetime by selecting a compound having a specific fused-azole ring structure, which can effectively exhibit electron injection/transport roles.

According to the present invention, the luminous efficiency, driving voltage, and durability of the conventional organic EL devices can be improved.

BRIEF DESCRIPTION OF DRAWINGS

The FIGURE is a diagram illustrating the configuration of the organic EL devices of Examples 29 to 43 and Comparative Examples 1 to 2.

DESCRIPTION OF EMBODIMENTS

These compounds can be synthesized, for example, according to a known method as described below (refer to PTLs 5 and 6, NPLs 6 and 7, for example).

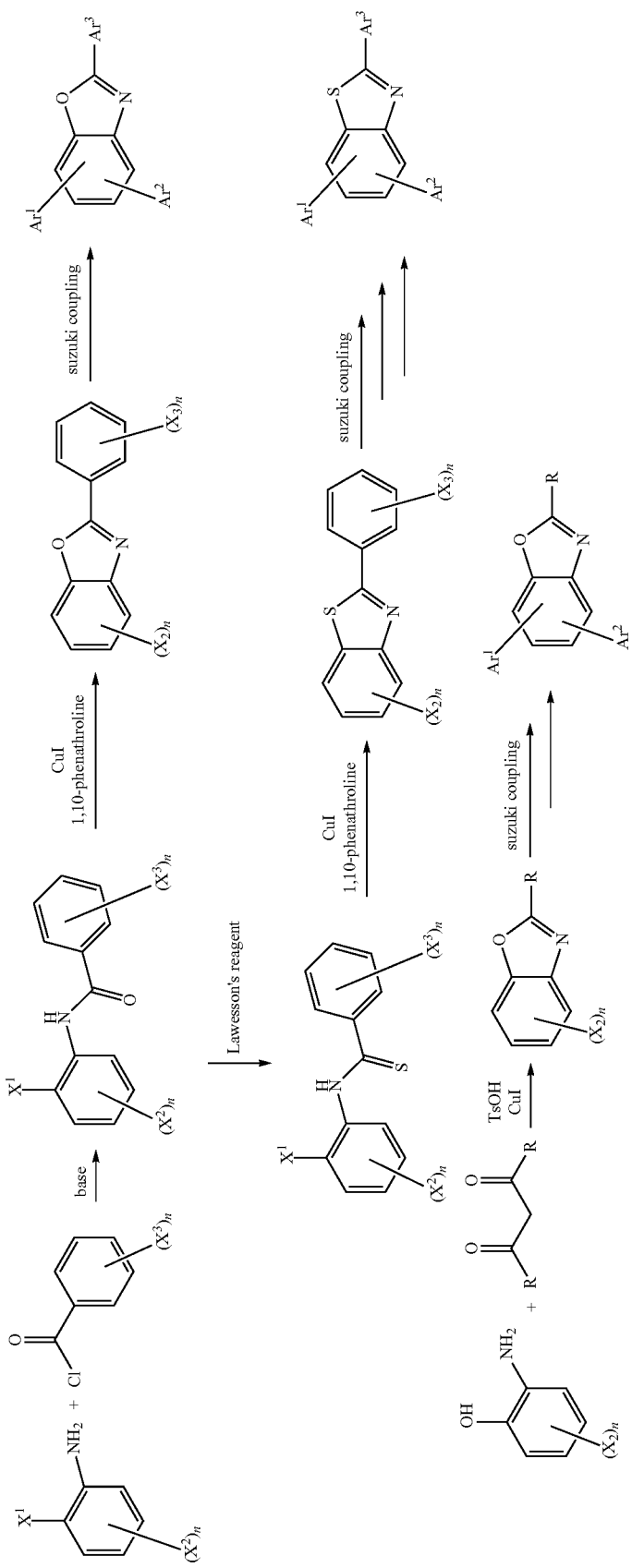

The following presents specific examples of preferred compounds among the benzoxazole compounds of the general formula (1) preferably used in the organic EL device of the present invention. The present invention, however, is not restricted to these compounds.
[Chemical Formula 7]
[Chemical Formula 8]
[Chemical Formula 9]
[Chemical Formula 10]
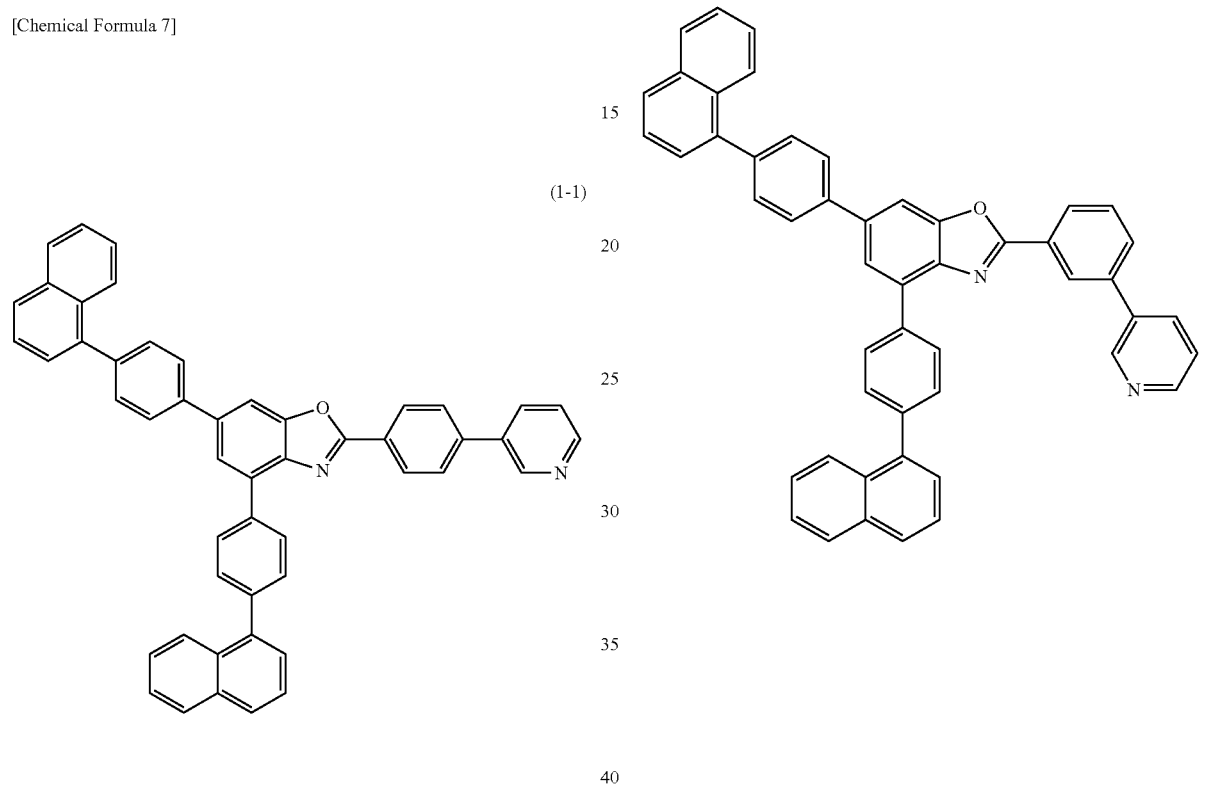
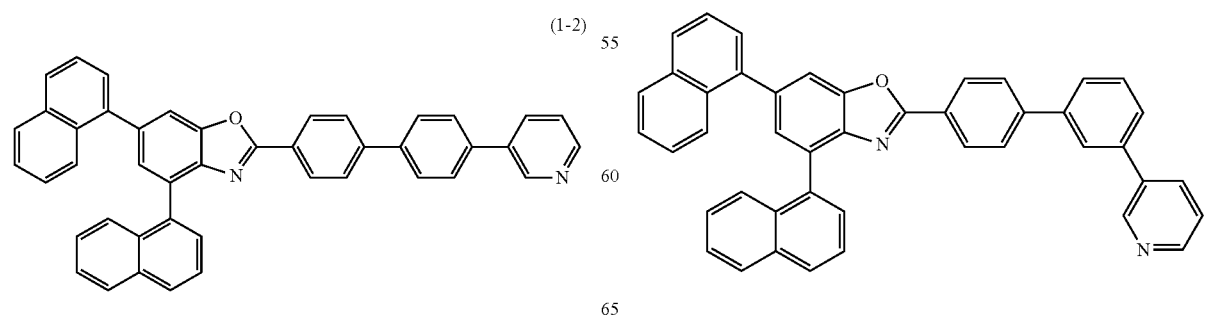

[Chemical Formula 11]
(1-5)
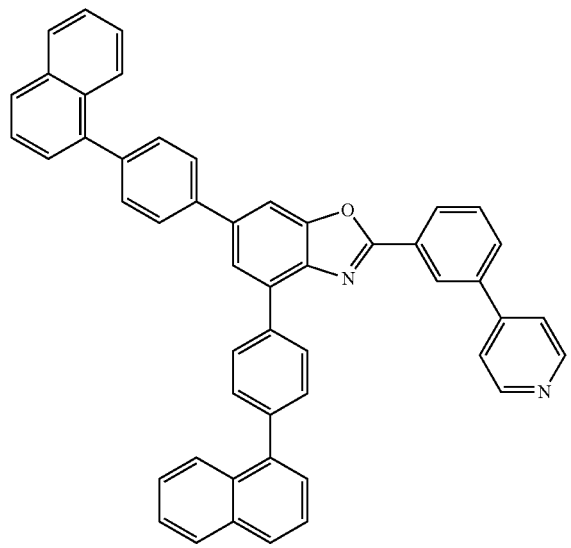
[Chemical Formula 12]
(1-6)
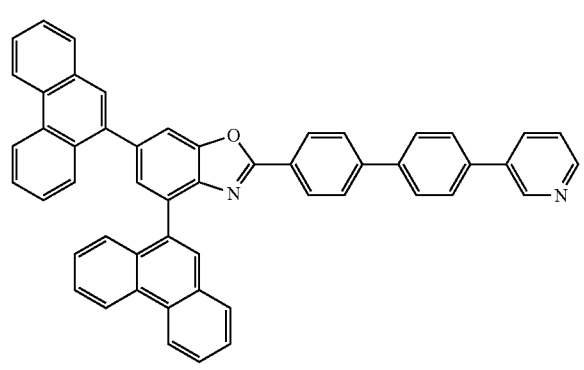
[Chemical Formula 13]
(1-7)
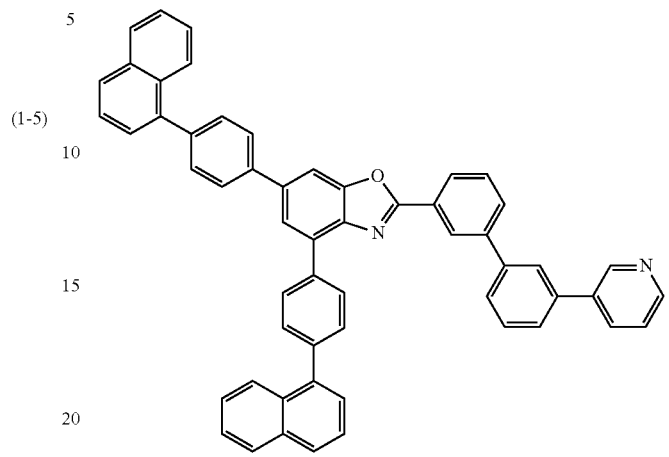
[Chemical Formula 14]
(1-8)
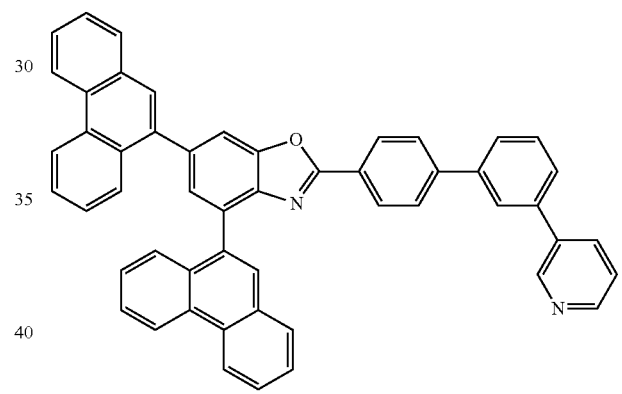
[Chemical Formula 15]
(1-9)
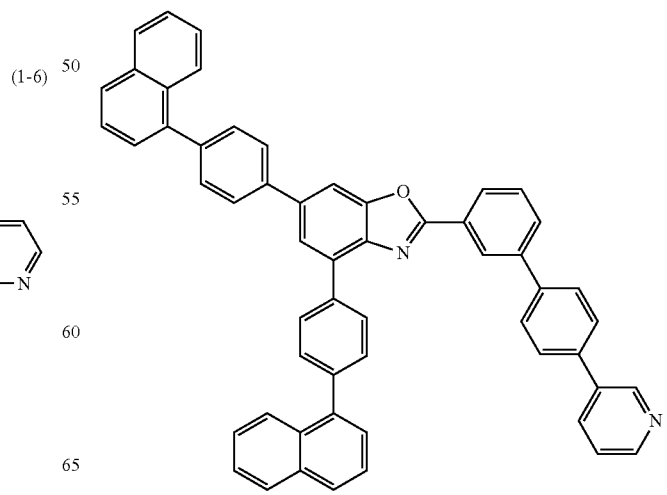

[Chemical Formula 16]
(1-10)
[Chemical Formula 17]
(1-11)
[Chemical Formula 18]
(1-12)
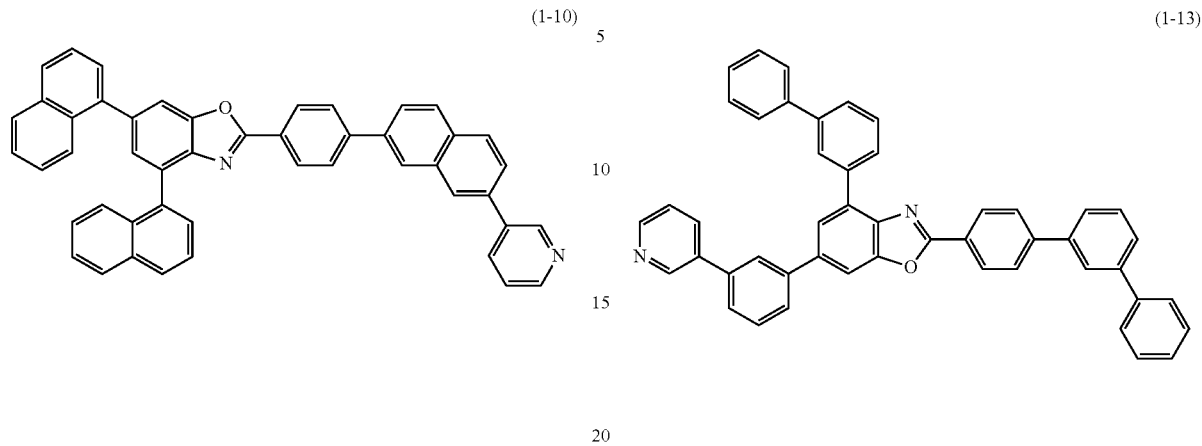
[Chemical Formula 19]
(1-13)
[Chemical Formula 20]
(1-14)
[Chemical Formula 21]
(1-15)
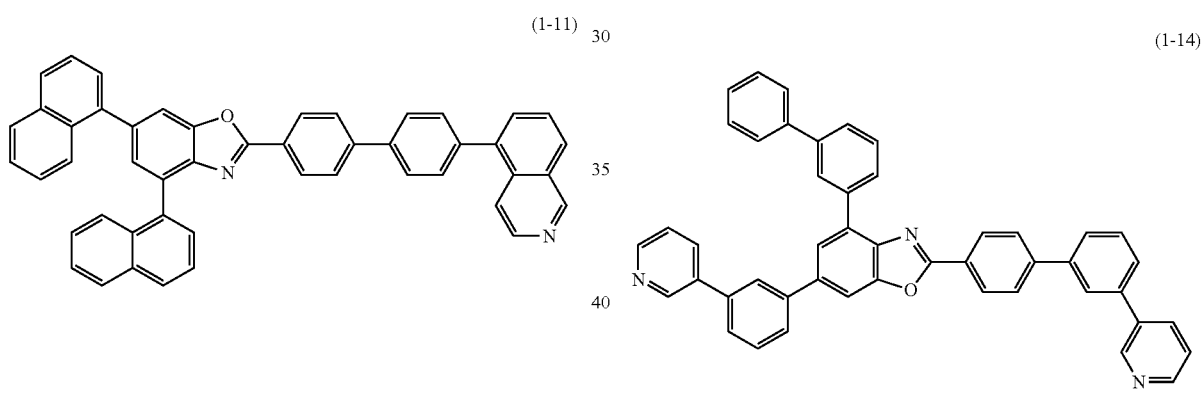
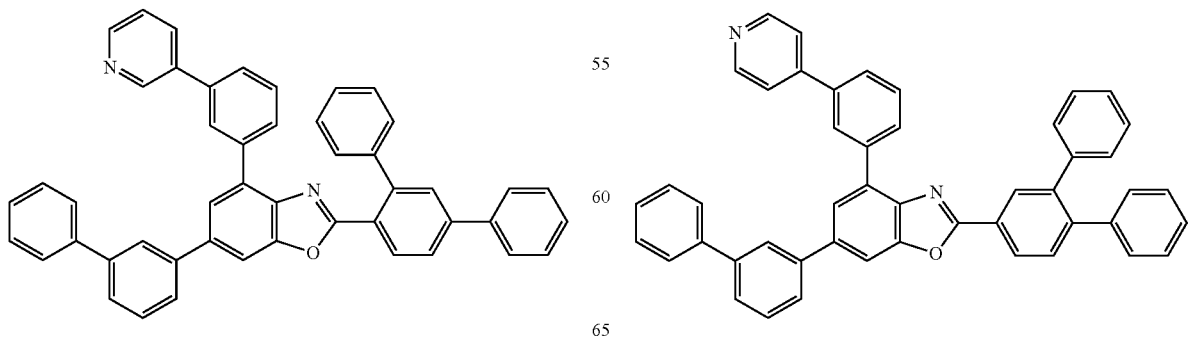

[Chemical Formula 22]
(1-16)
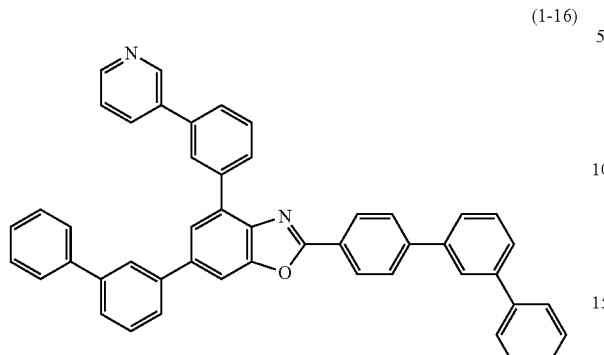
[Chemical Formula 23]
(1-17)
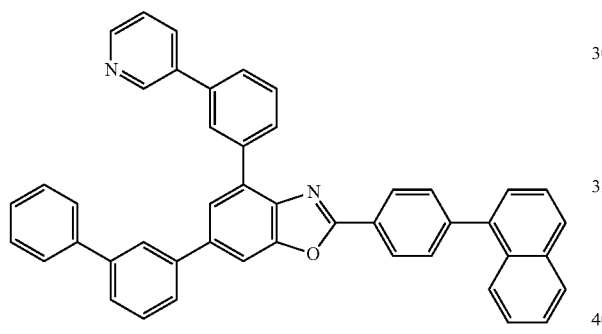
[Chemical Formula 24]
(1-18)
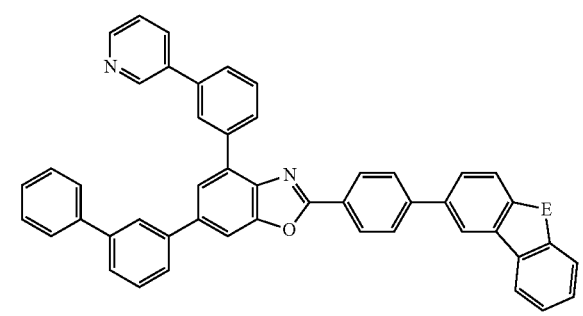
[Chemical Formula 25]
(1-19)
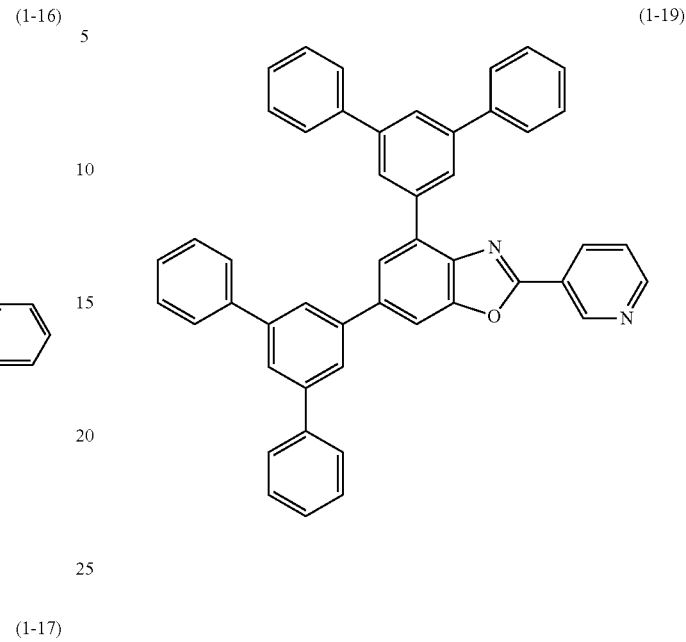
[Chemical Formula 26]
(1-20)
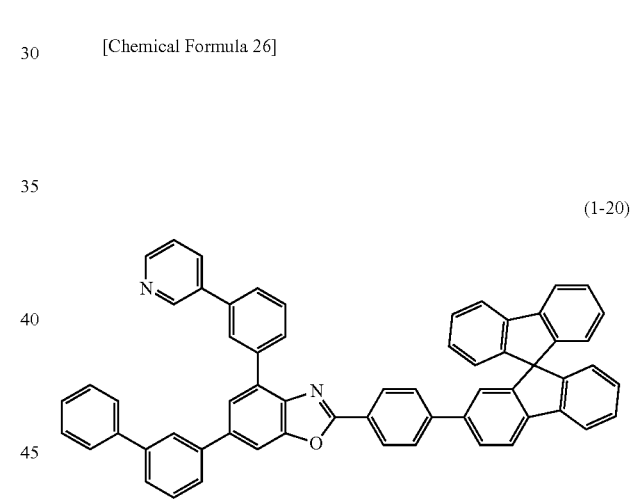
[Chemical Formula 27]
(1-21)

[Chemical Formula 28]
(1-22)
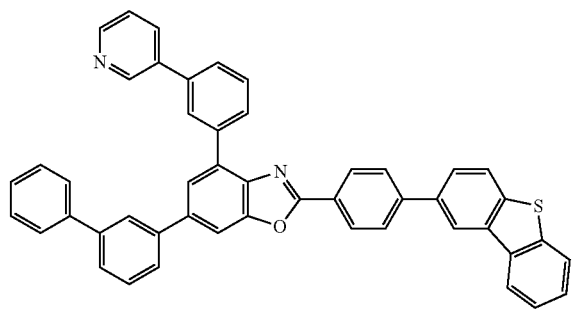
[Chemical Formula 29]
(1-23)
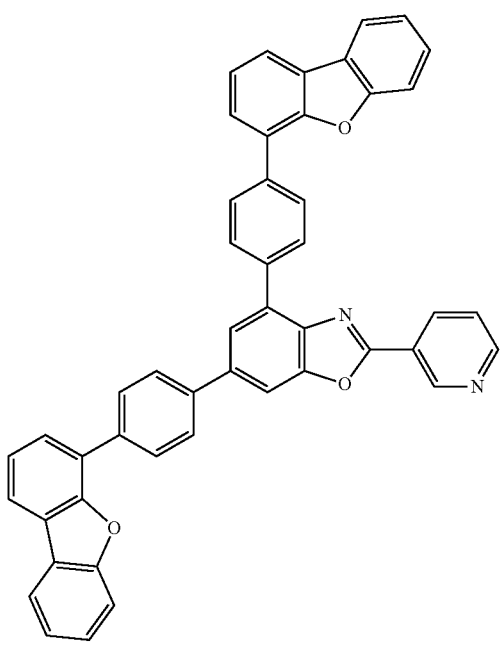
[Chemical Formula 30]
(1-24)
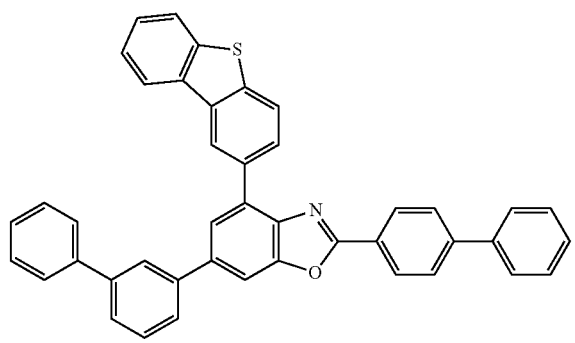
[Chemical Formula 31]
(1-25)
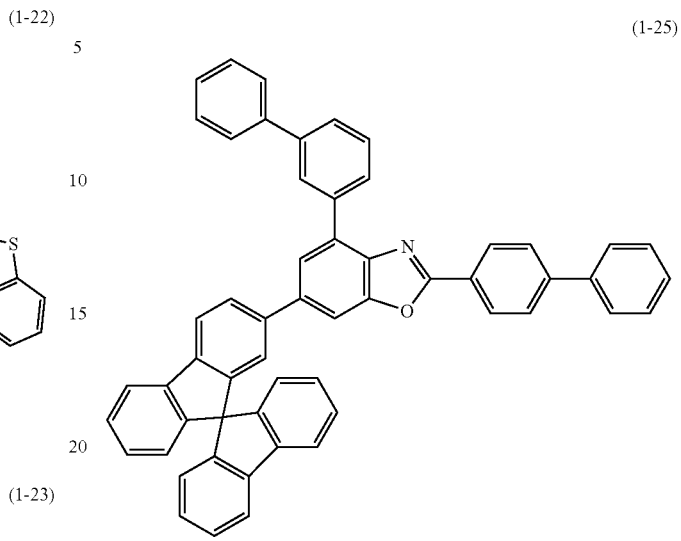
[Chemical Formula 32]
(1-26)
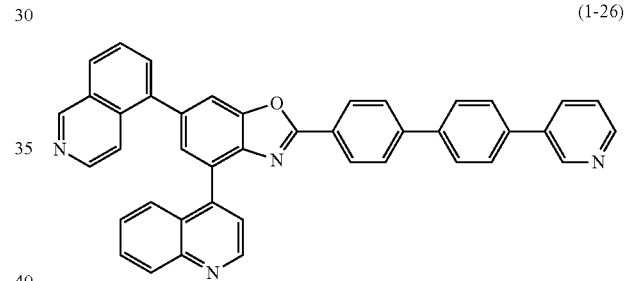
[Chemical Formula 33]
(1-27)
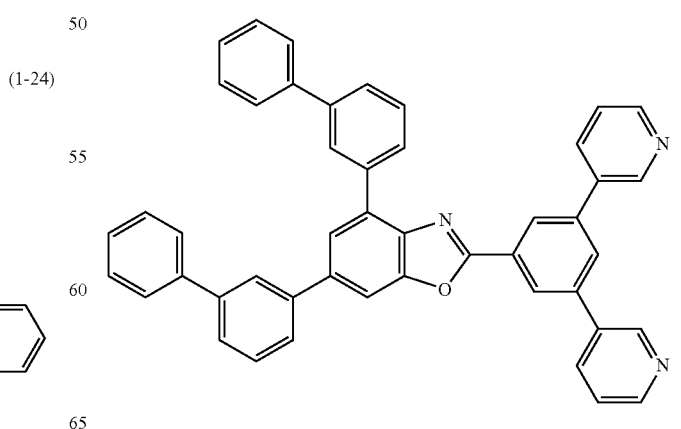

[Chemical Formula 34]
(1-28)
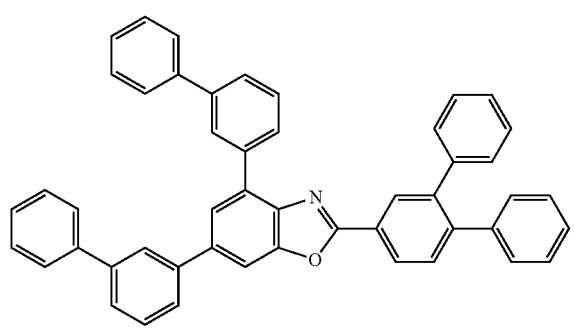
[Chemical Formula 35]
(1-29)
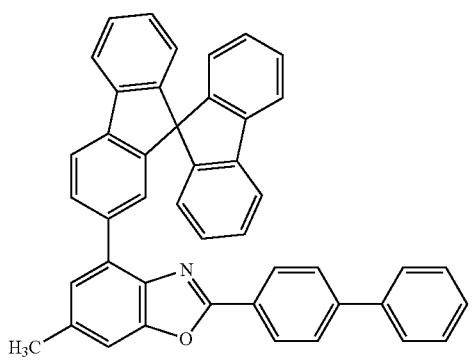
[Chemical Formula 36]
(1-30)
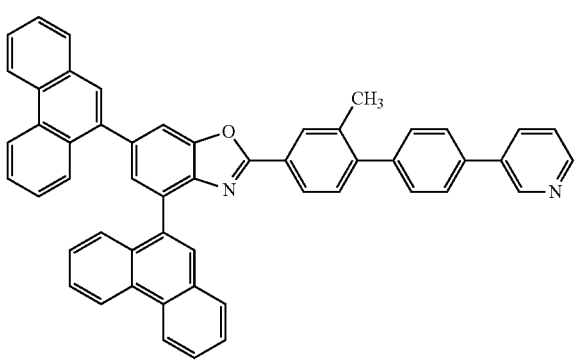
[Chemical Formula 37]
(1-31)
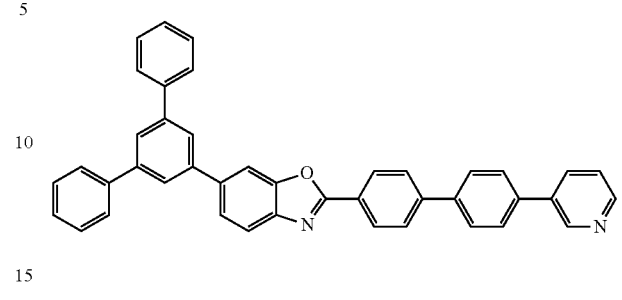
[Chemical Formula 38]
(1-32)
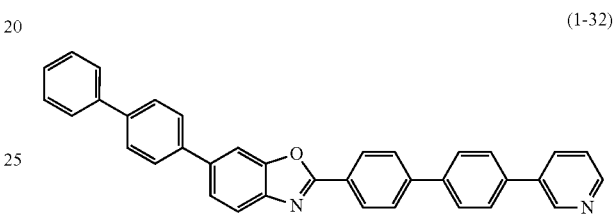
[Chemical Formula 39]
(1-33)
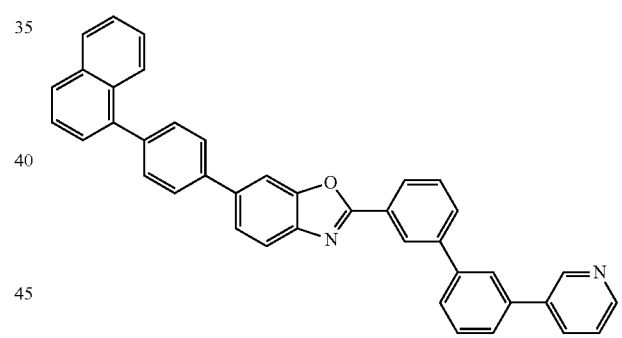
[Chemical Formula 40]
(1-34)
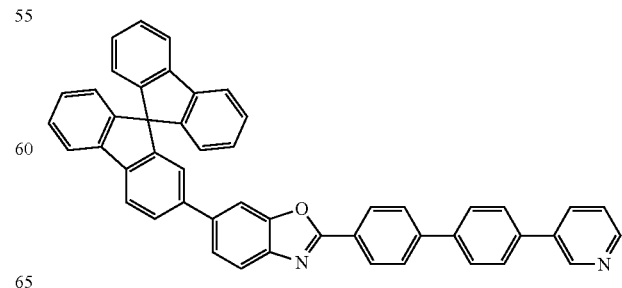

[Chemical Formula 41]
(1-35)
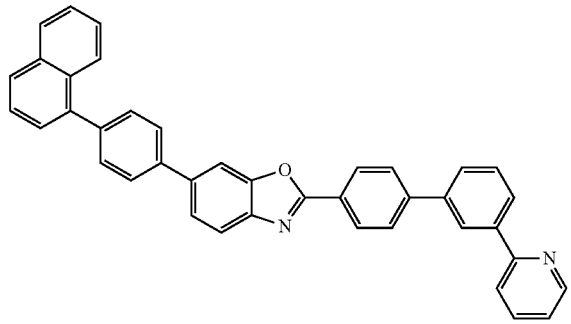
[Chemical Formula 42]
(1-36)
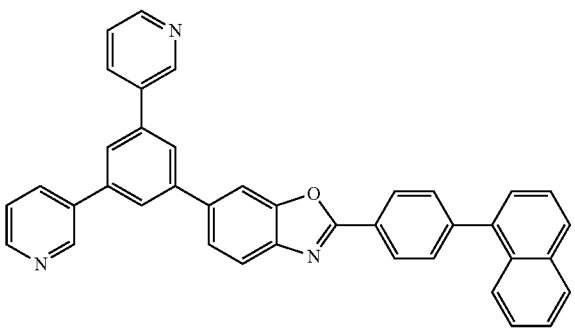
[Chemical Formula 43]
(1-37)
[Chemical Formula 44]
(1-38)
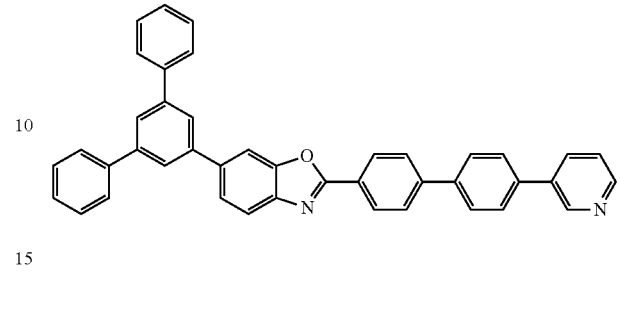
[Chemical Formula 45]
(1-39)
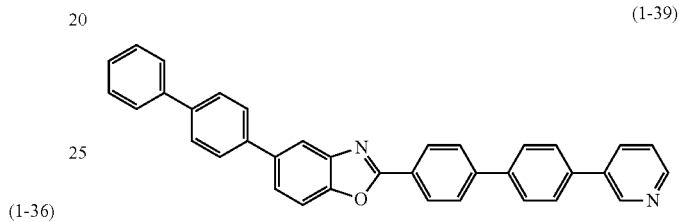
[Chemical Formula 46]
(1-40)
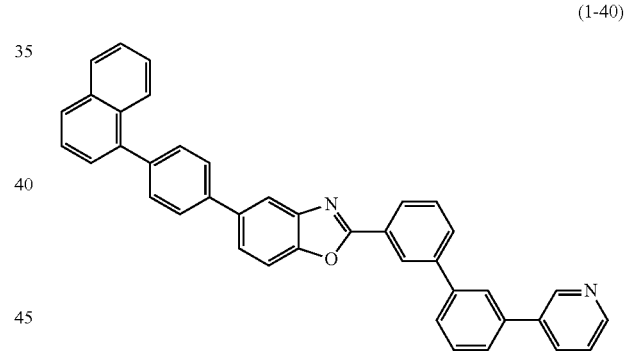
[Chemical Formula 47]
(1-41)
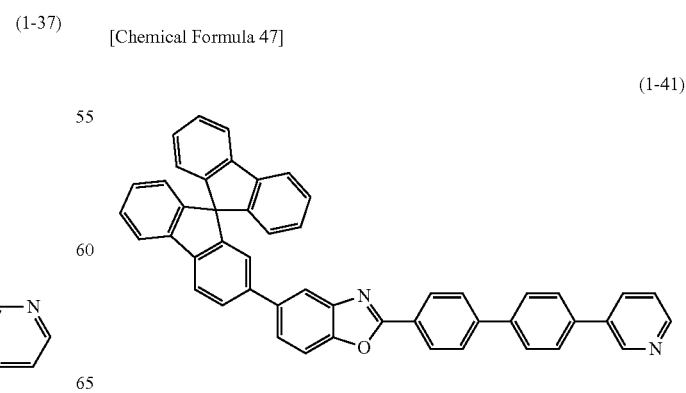

[Chemical Formula 48]
(1-42)
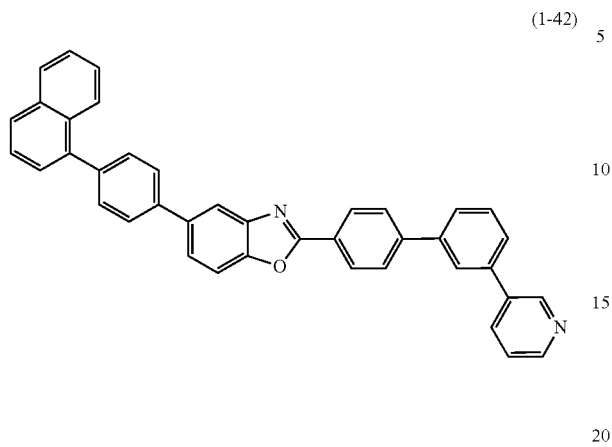
[Chemical Formula 49]
(1-43)
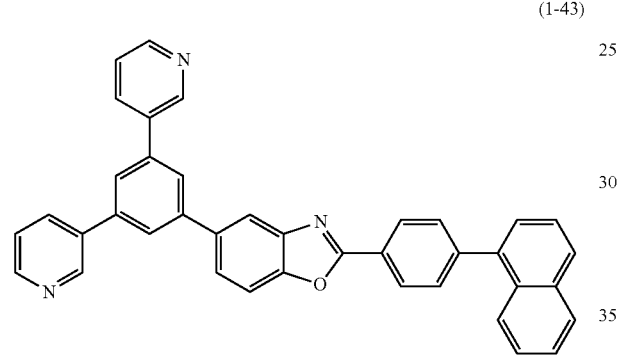
[Chemical Formula 50]
(1-44)
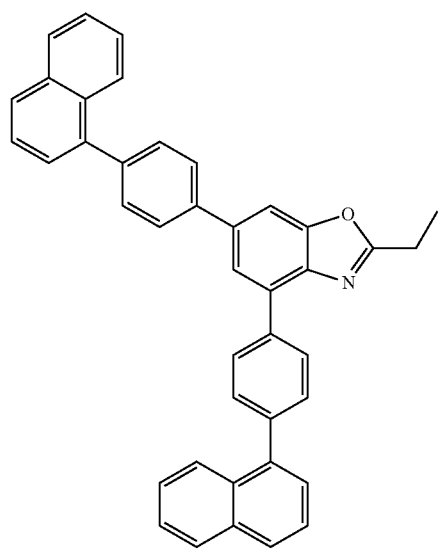
[Chemical Formula 51]
(1-45)
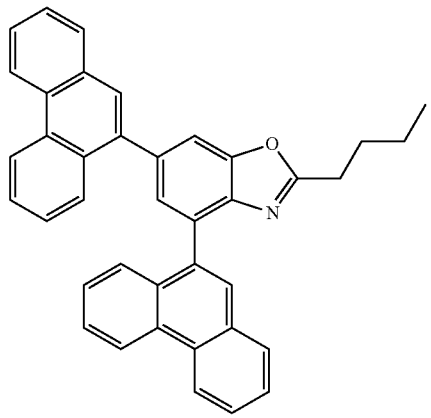
[Chemical Formula 52]
(1-46)
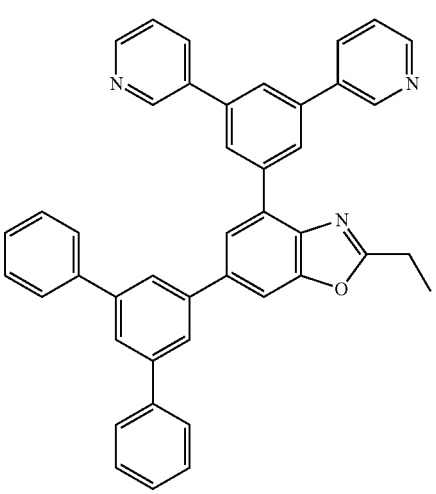

[Chemical Formula 53]
(1-47)
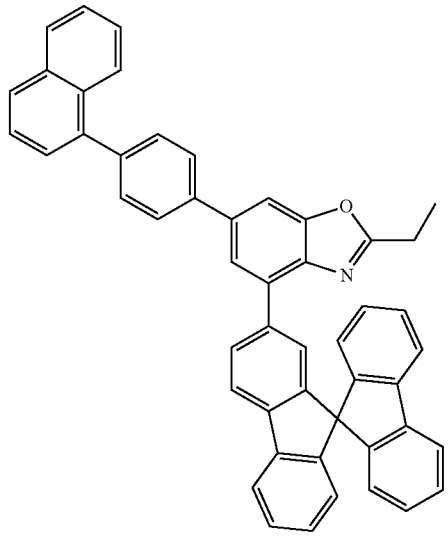
[Chemical Formula 54]
(1-48)
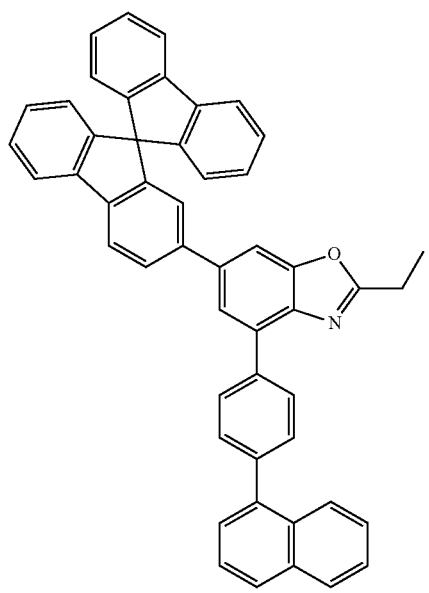
[Chemical Formula 55]
(1-49)
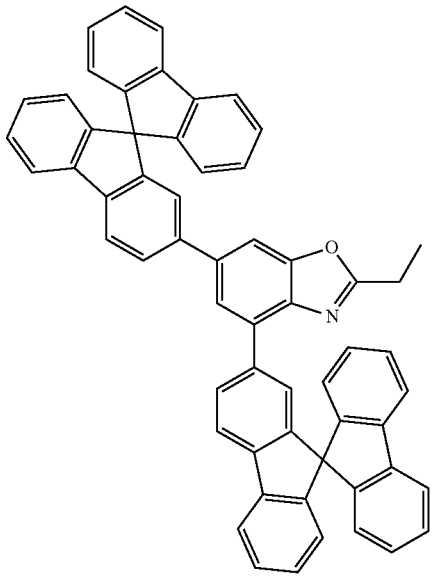
[Chemical Formula 56]
(1-50)
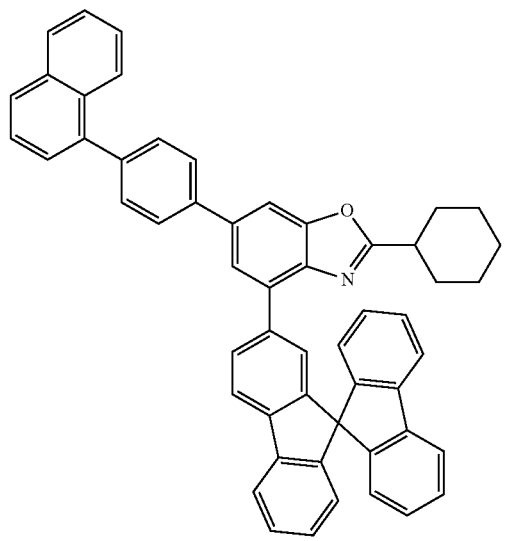

[Chemical Formula 57]
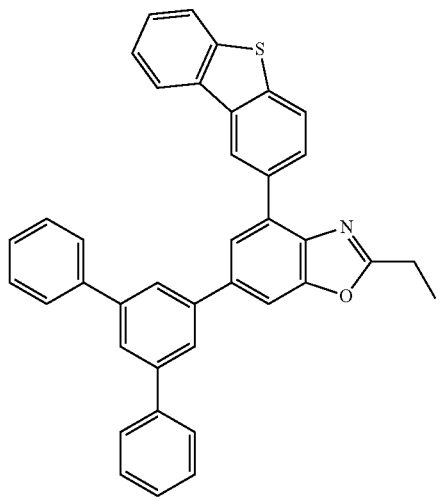
(1-51)
[Chemical Formula 58]
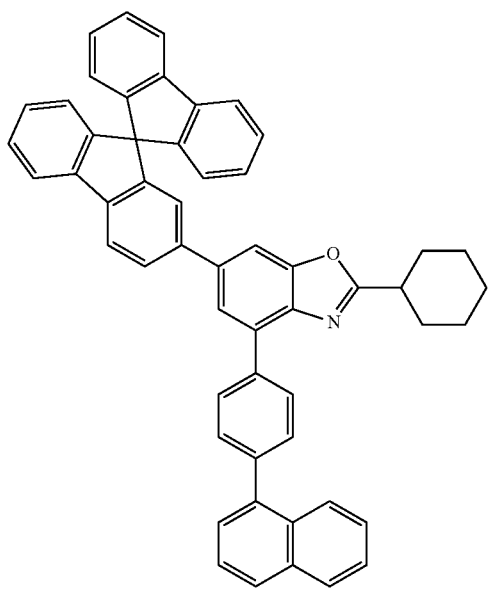
(1-52)
[Chemical Formula 59]
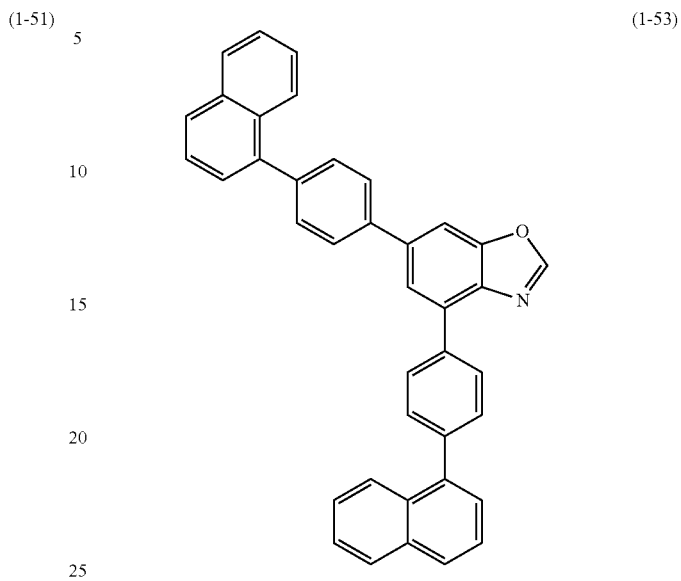
(1-53)
[Chemical Formula 60]
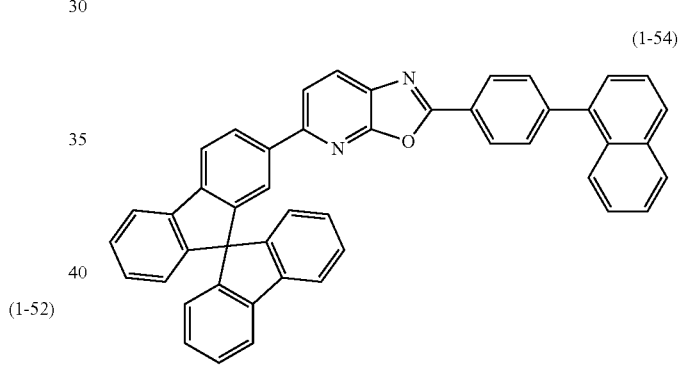
(1-54)
[Chemical Formula 61]
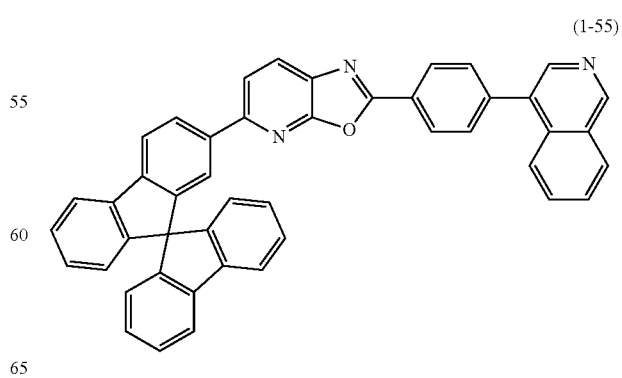
(1-55)

[Chemical Formula 62]
(1-56)
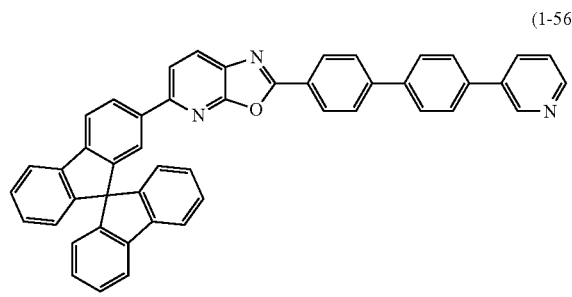
[Chemical Formula 63]
(1-57)
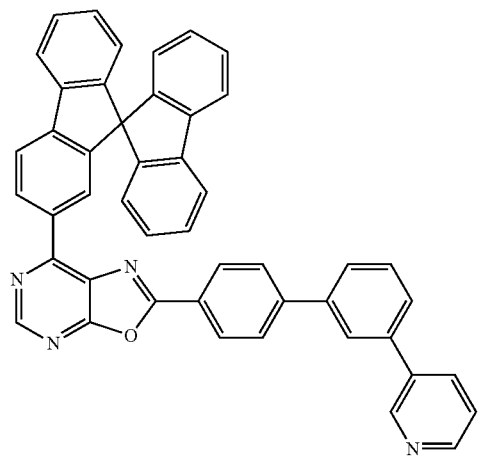
[Chemical Formula 64]
(1-58)
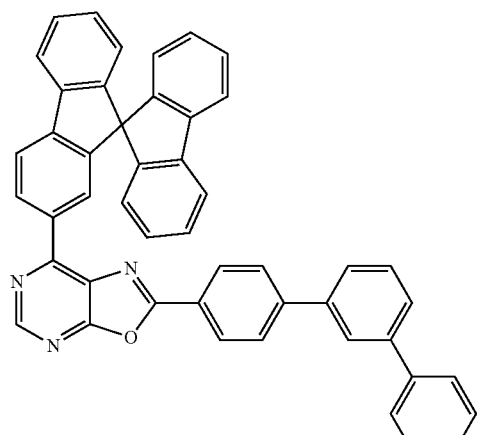
[Chemical Formula 65]
(1-59)
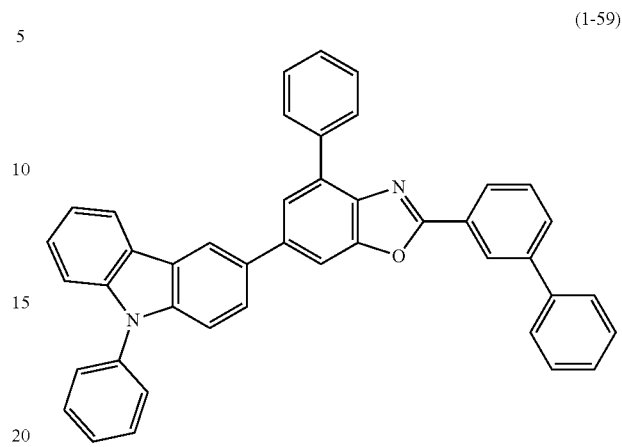
[Chemical Formula 66]
(1-60)
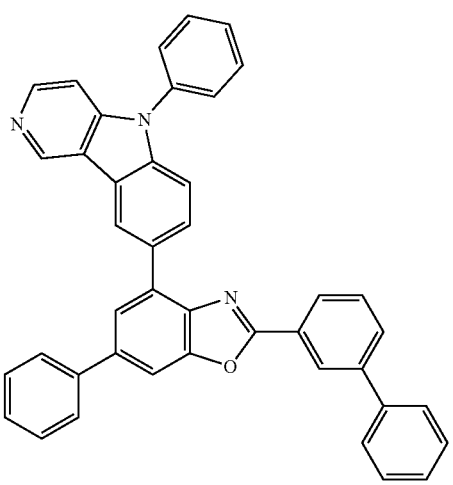

[Chemical Formula 67]
(1-61)
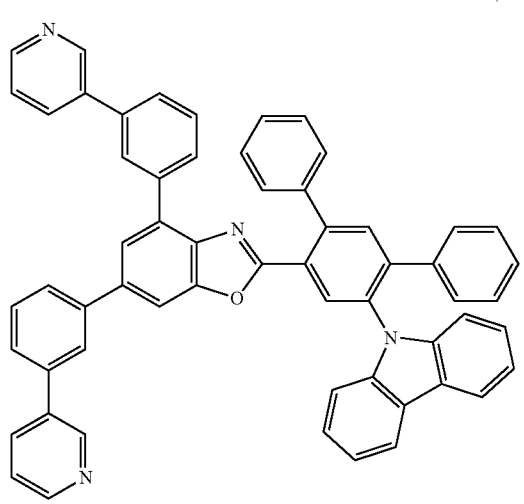
[Chemical Formula 68]
(1-62)
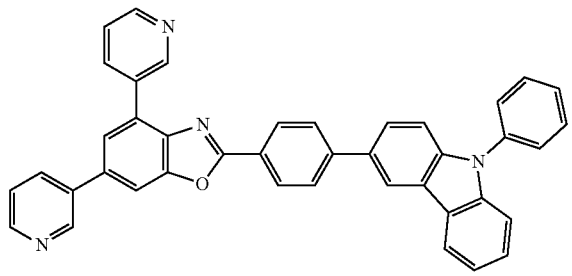
[Chemical Formula 69]
(1-63)
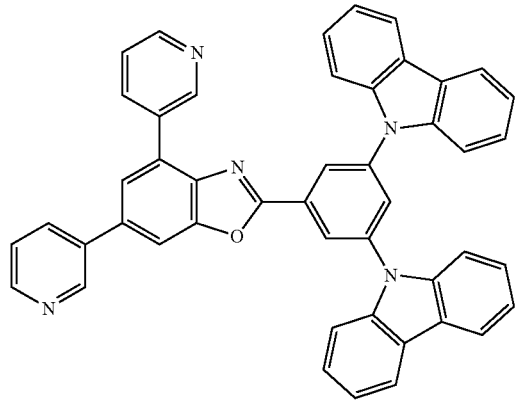
[Chemical Formula 70]
(1-64)
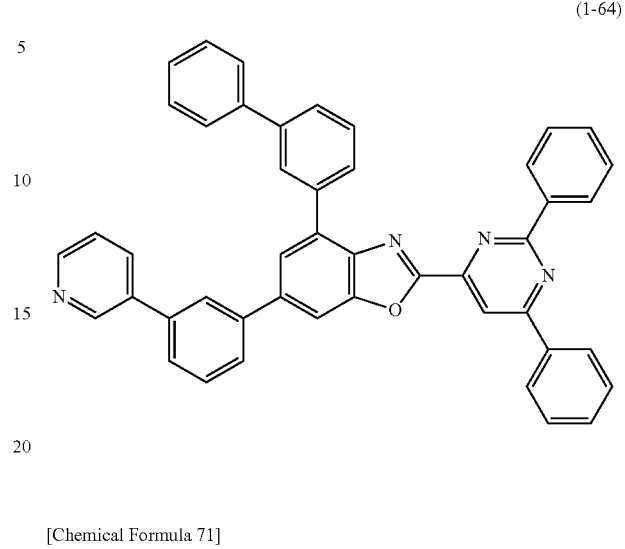
[Chemical Formula 71]
(1-65)
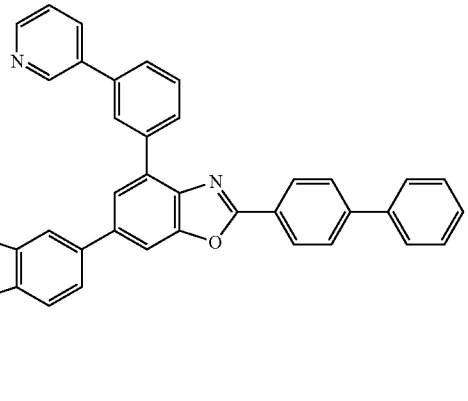
[Chemical Formula 72]
(1-66)

[Chemical Formula 73]
(1-67)
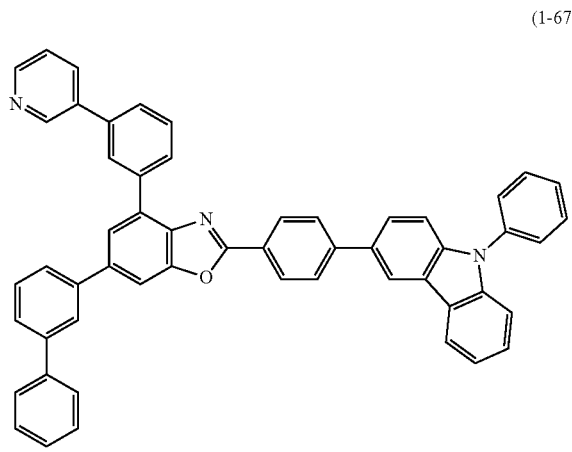
[Chemical Formula 74]
(1-68)
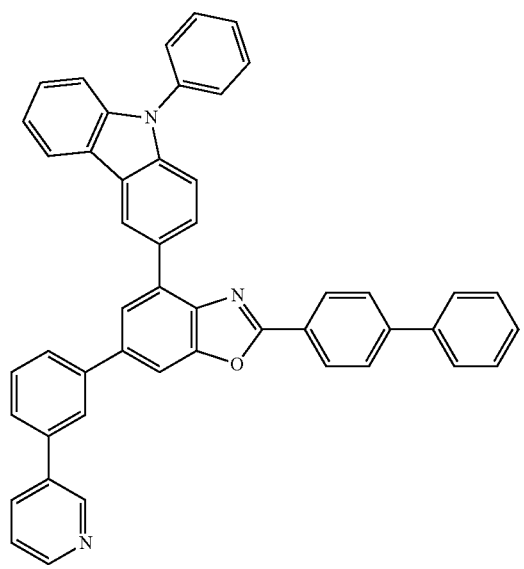
[Chemical Formula 75]
(1-69)
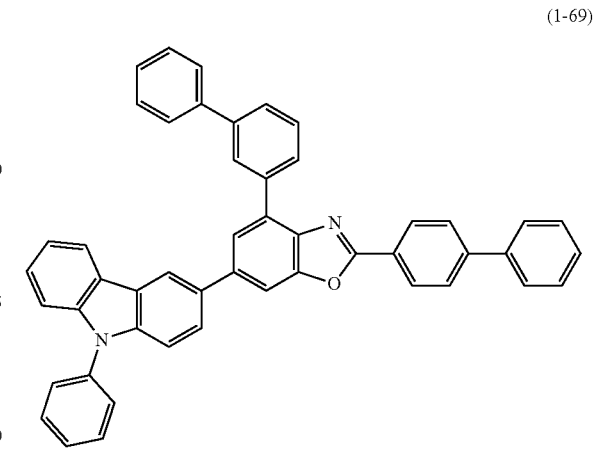
[Chemical Formula 76]
(1-70)
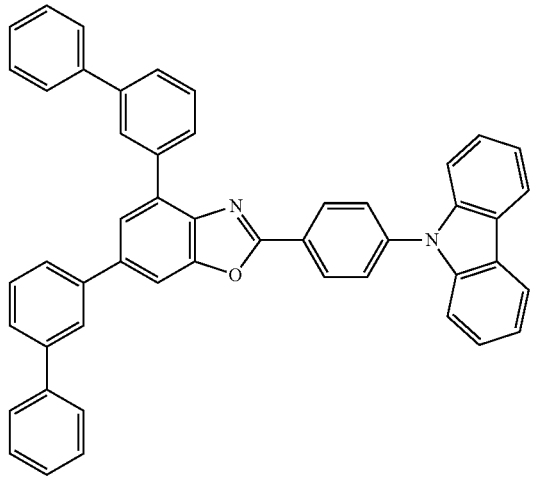

[Chemical Formula 77]
(1-71)
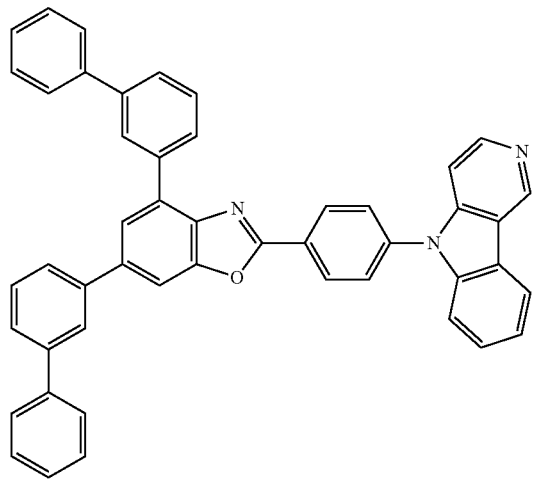
[Chemical Formula 78]
(1-72)
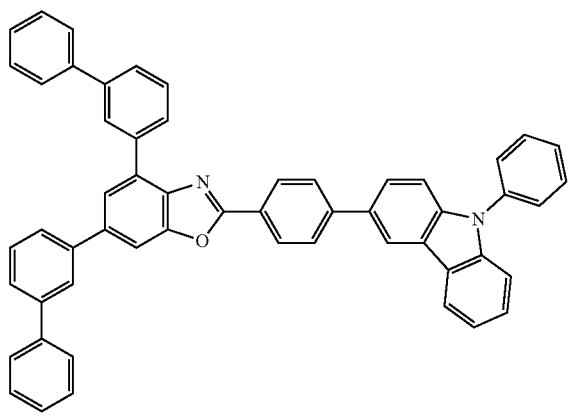
[Chemical Formula 79]
(1-73)
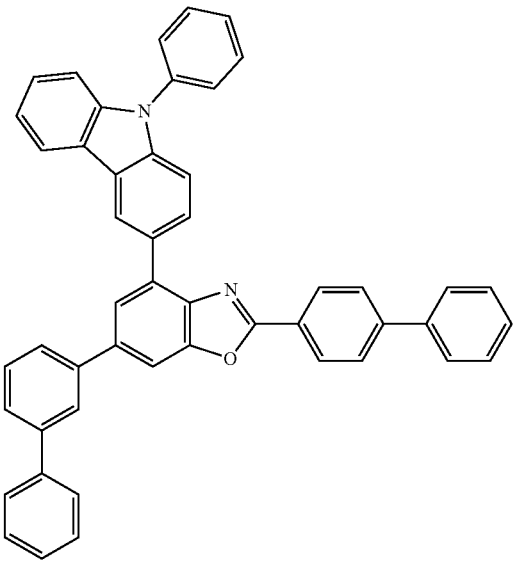
[Chemical Formula 80]
(1-74)
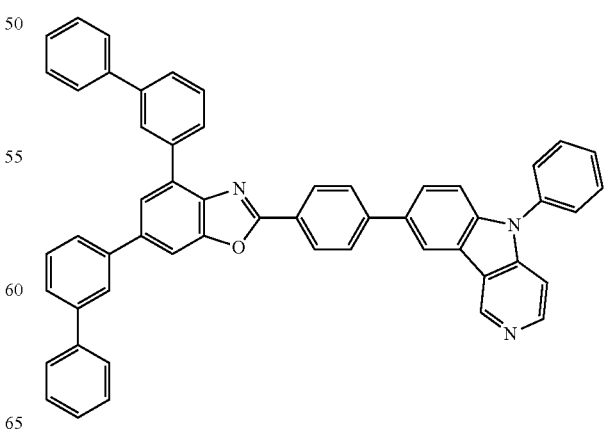

[Chemical Formula 81]
(1-75)
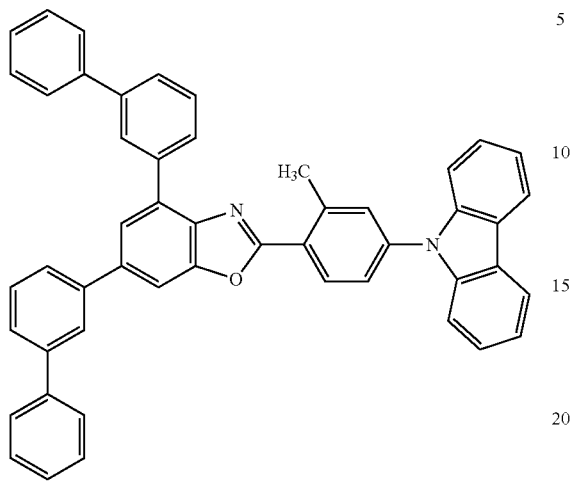
[Chemical Formula 82]
(1-76)
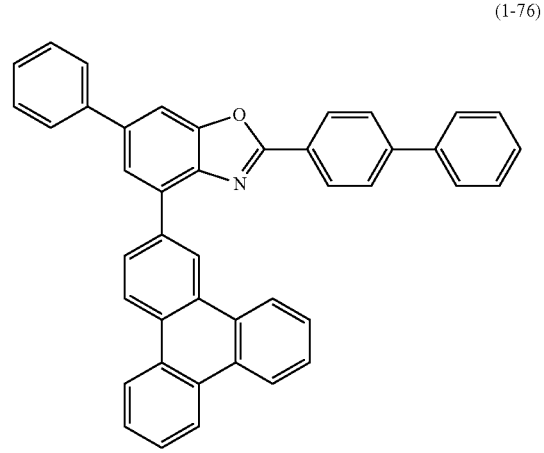
[Chemical Formula 83]
(1-77)
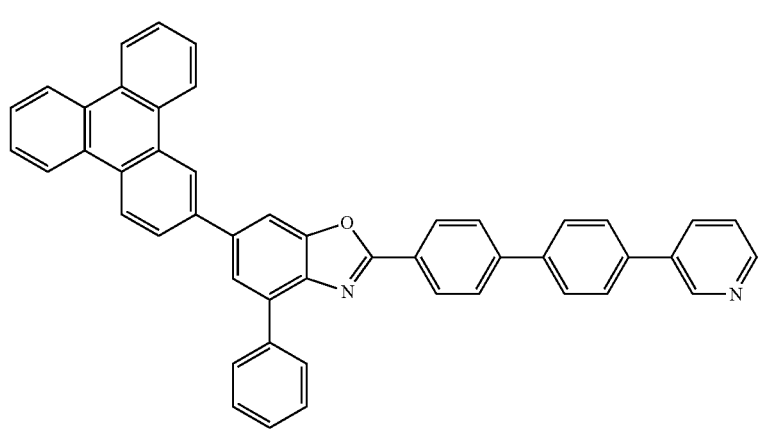
[Chemical Formula 84]
(1-78)
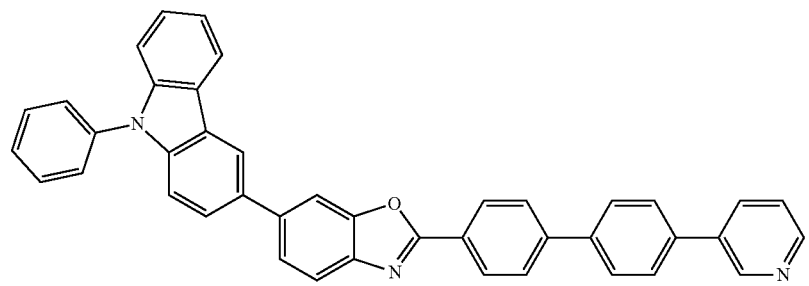

[Chemical Formula 85]
(1-79)
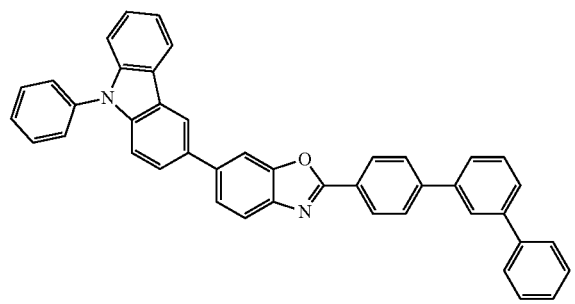
[Chemical Formula 86]
(1-80)
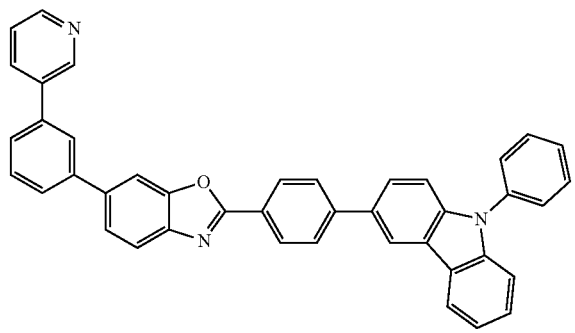
[Chemical Formula 87]
(1-81)
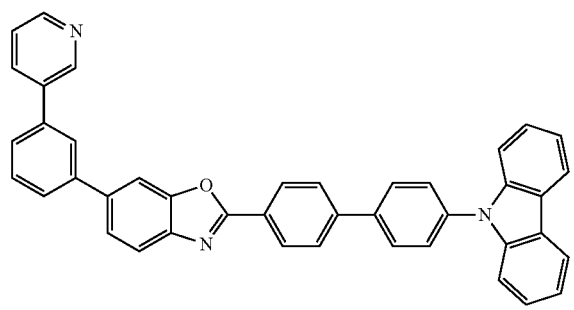
[Chemical Formula 88]
(1-82)
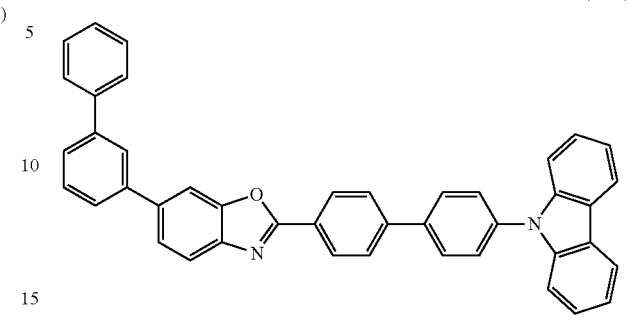
[Chemical Formula 89]
(1-83)
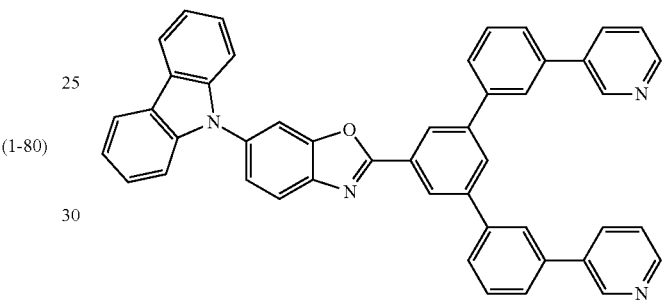
[Chemical Formula 90]
(1-84)
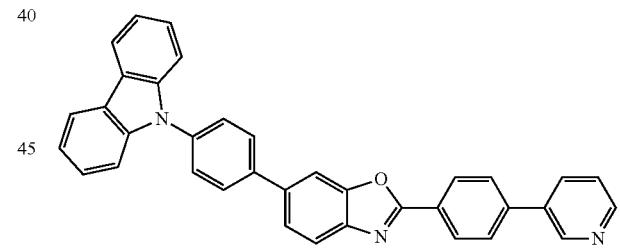
[Chemical Formula 91]
(1-85)
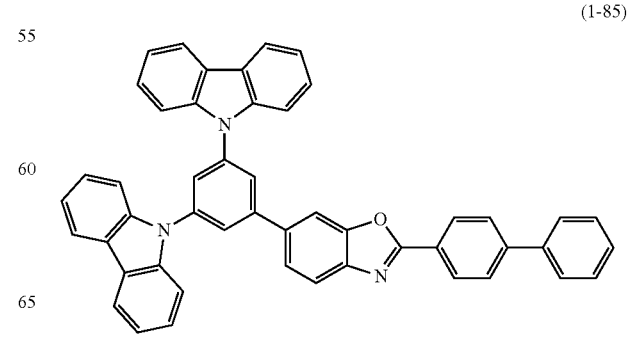

[Chemical Formula 92]
(1-86)
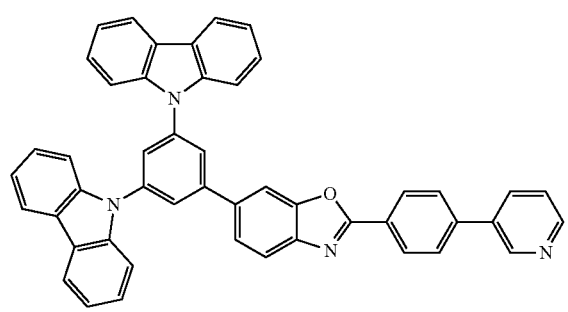
[Chemical Formula 93]
(1-87)
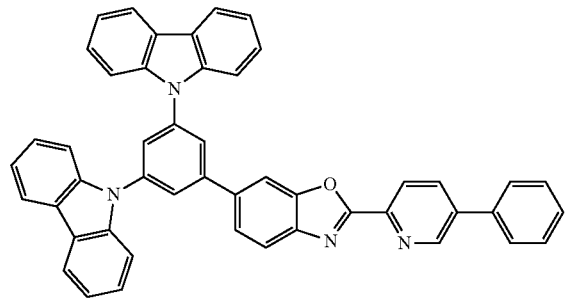
[Chemical Formula 94]
(1-88)
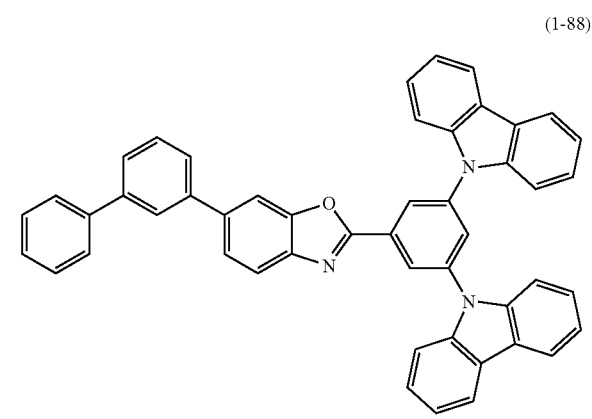
[Chemical Formula 95]
(1-89)
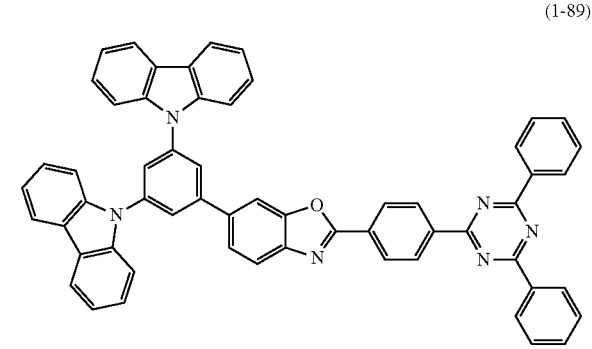
[Chemical Formula 96]
(1-90)
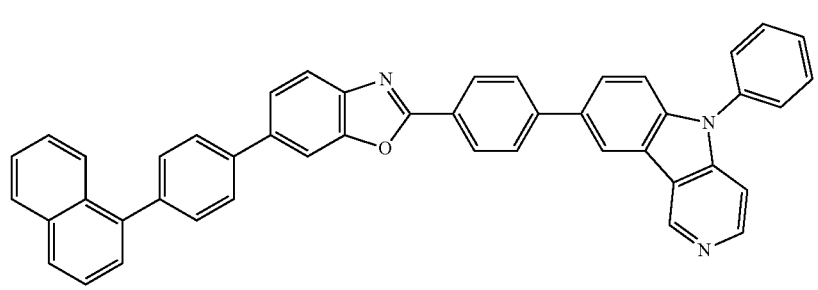

[Chemical Formula 97]
(1-91)
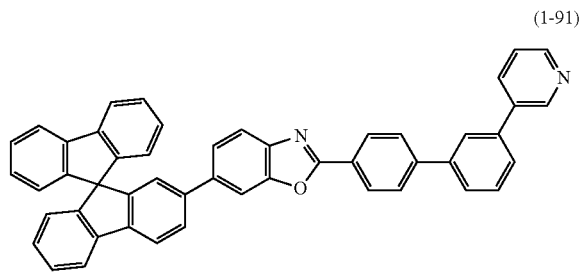
[Chemical Formula 98]
(1-92)
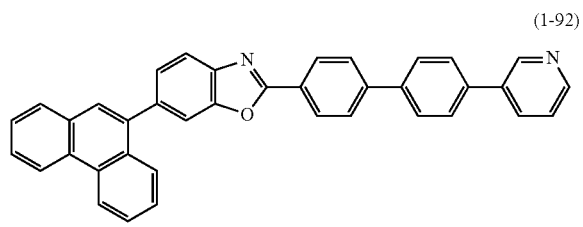
[Chemical Formula 99]
(1-93)
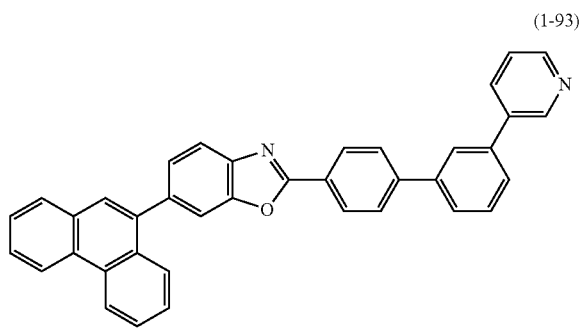
[Chemical Formula 100]
(1-94)
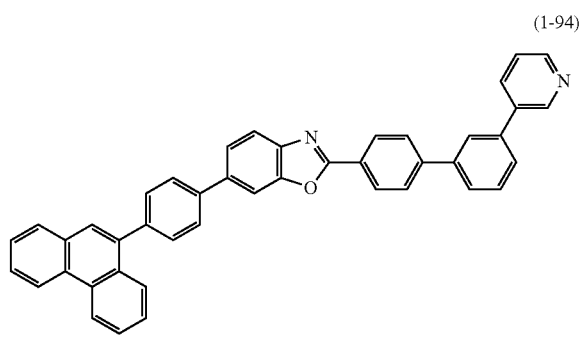
[Chemical Formula 101]
(1-95)
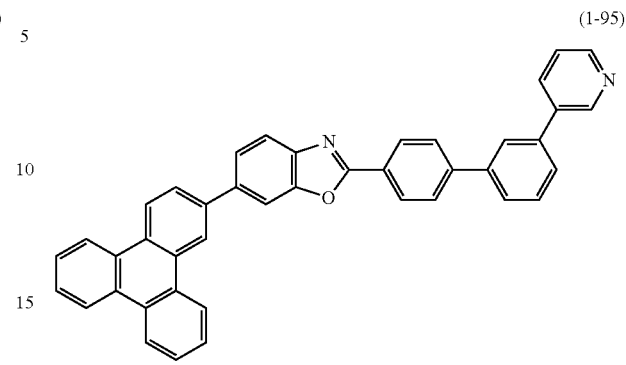
[Chemical Formula 102]
(1-96)
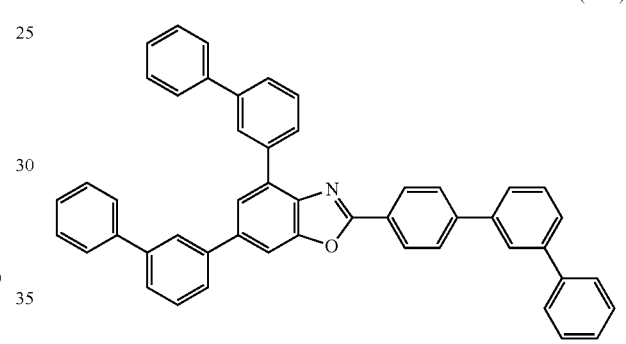
[Chemical Formula 103]
(1-97)
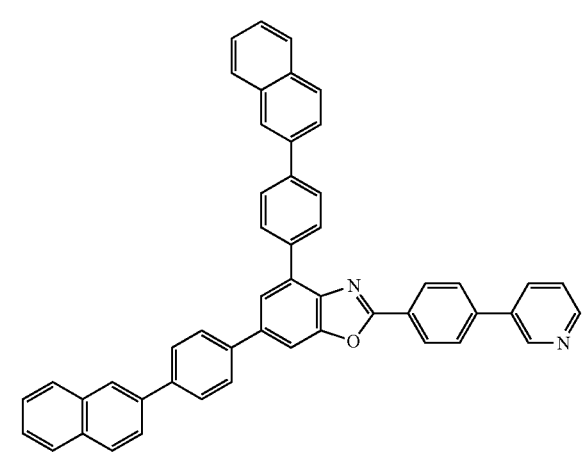

[Chemical Formula 104]
(1-98)
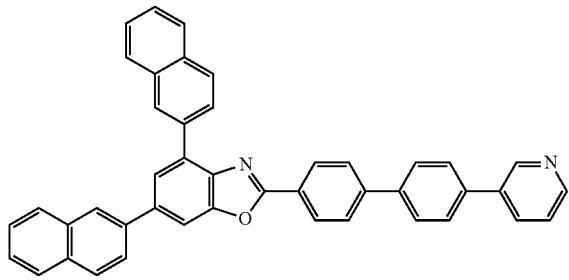
[Chemical Formula 105]
(1-99)
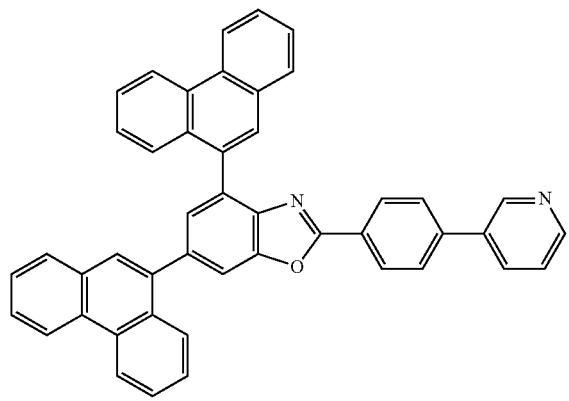
[Chemical Formula 106]
(1-100)
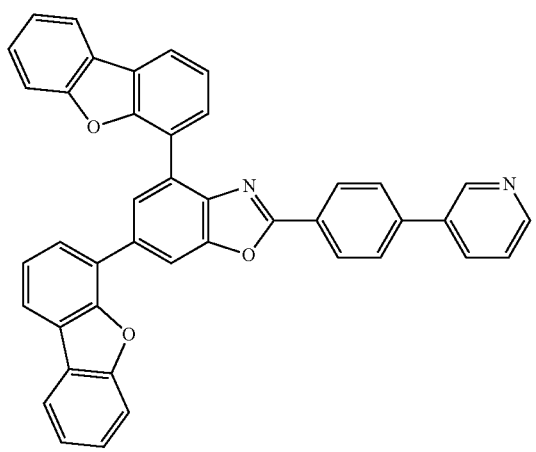
[Chemical Formula 107]
(1-101)
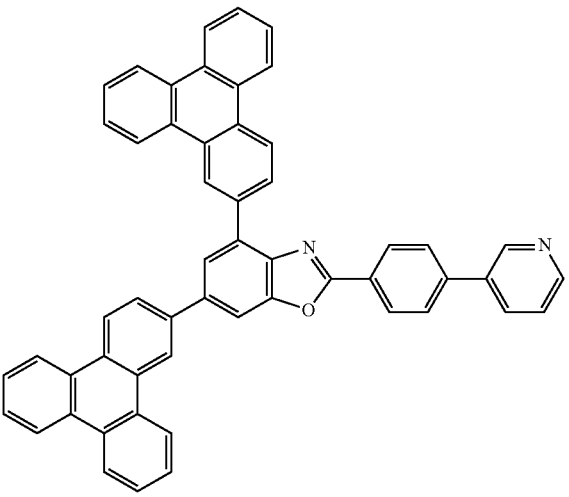
[Chemical Formula 108]
(1-102)
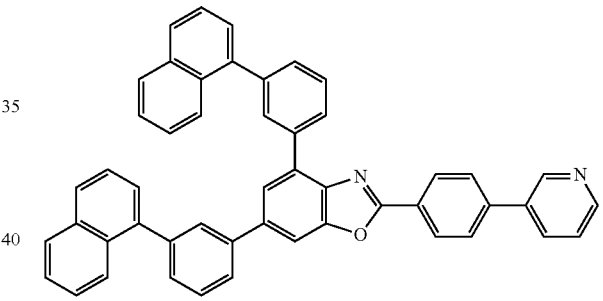
[Chemical Formula 109]
(1-103)
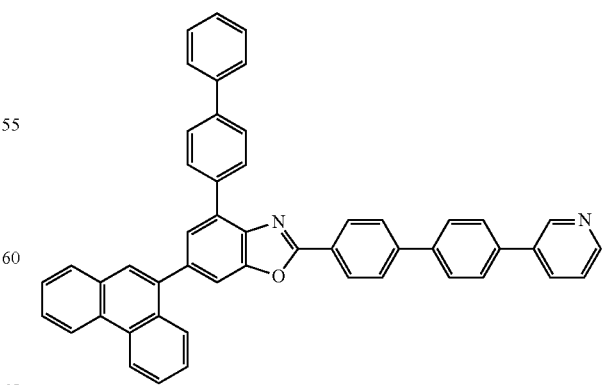

[Chemical Formula 110]
(1-104)
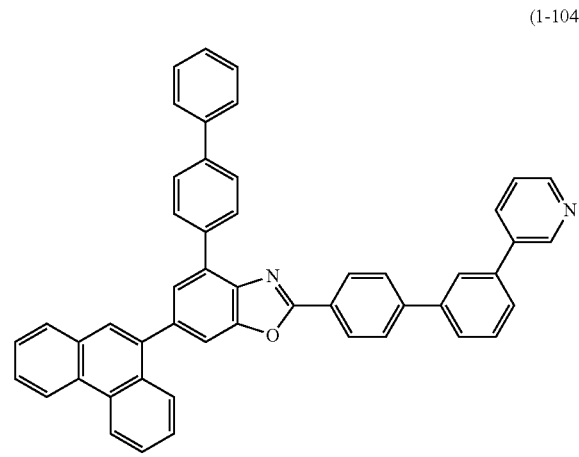
[Chemical Formula 111]
(1-105)
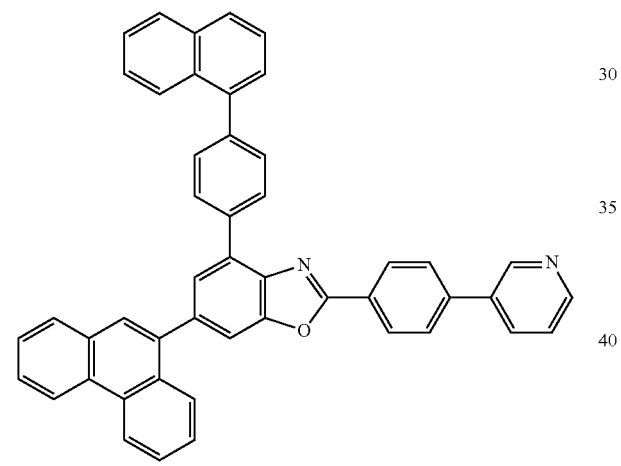
[Chemical Formula 112]
(1-106)
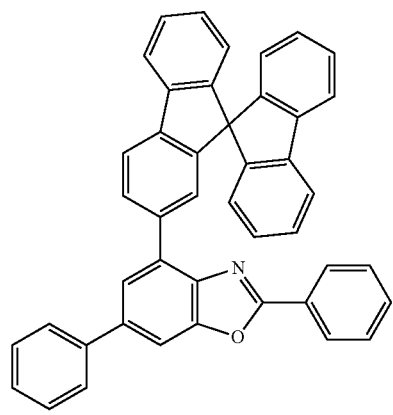
[Chemical Formula 113]
(1-107)
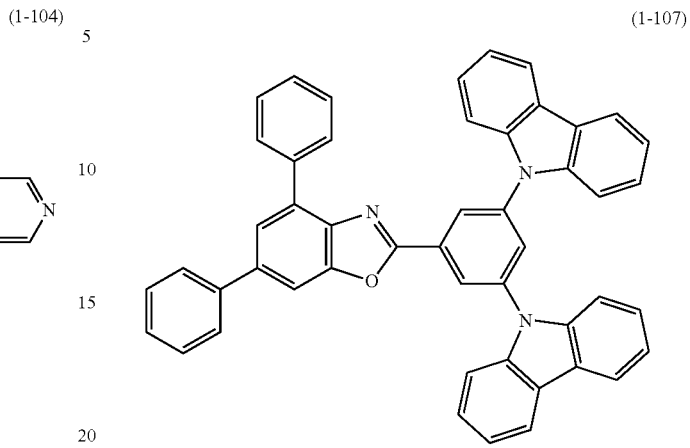
[Chemical Formula 114]
(1-108)
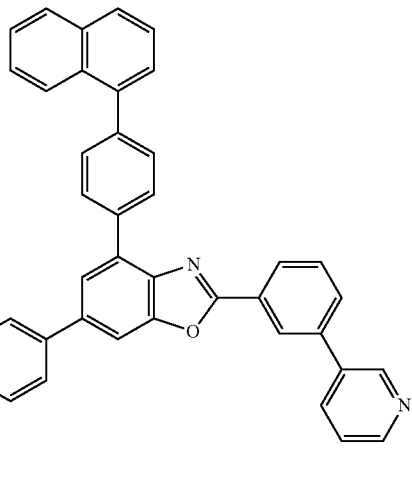

[Chemical Formula 115]
(1-109)
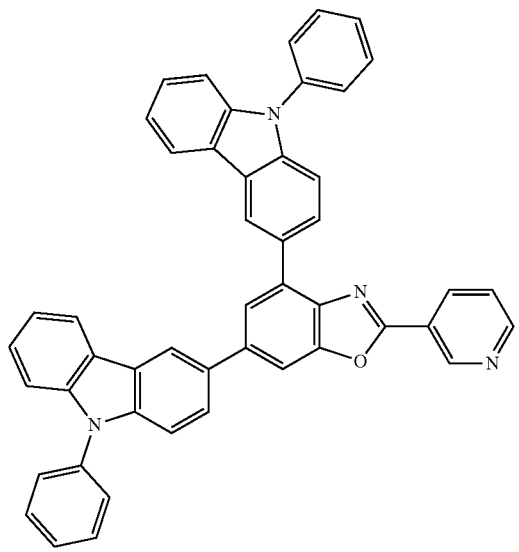
[Chemical Formula 116]
(1-110)
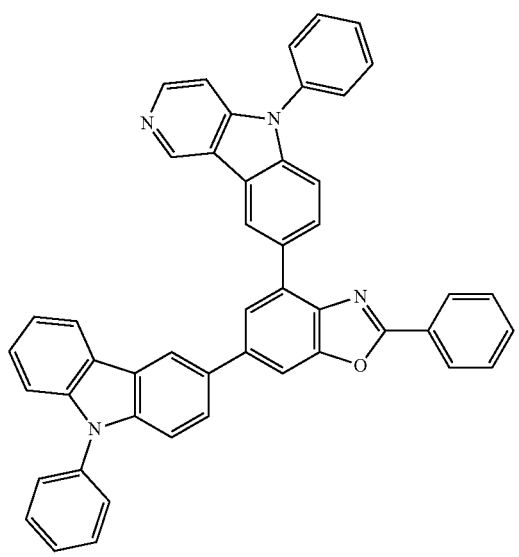
[Chemical Formula 117]
(1-111)
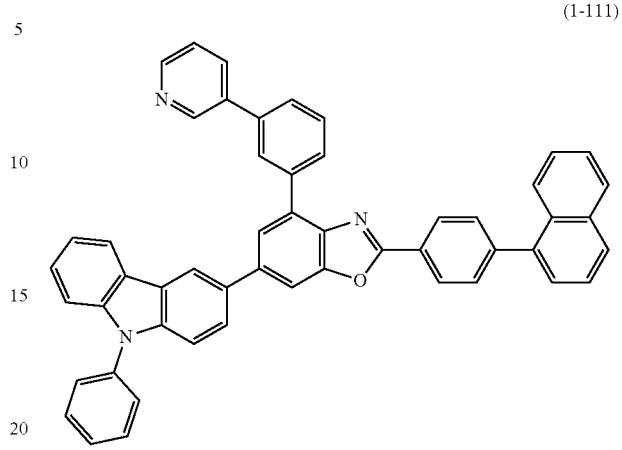
[Chemical Formula 118]
(1-112)
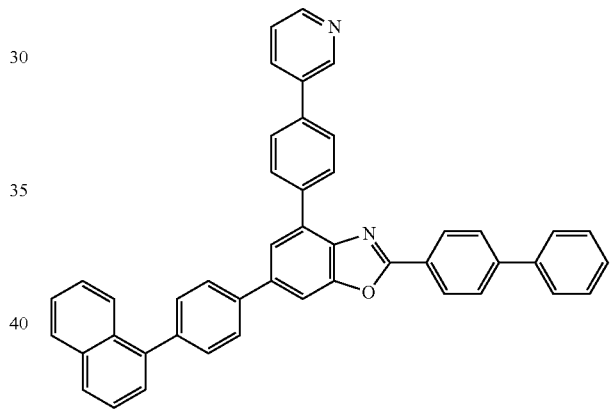
[Chemical Formula 119]
(1-113)
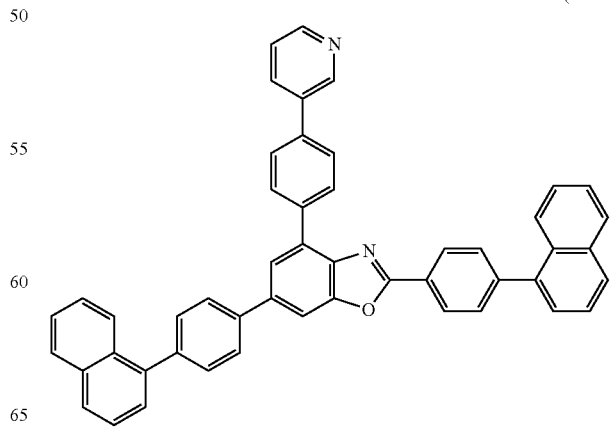

[Chemical Formula 120]
(1-114)
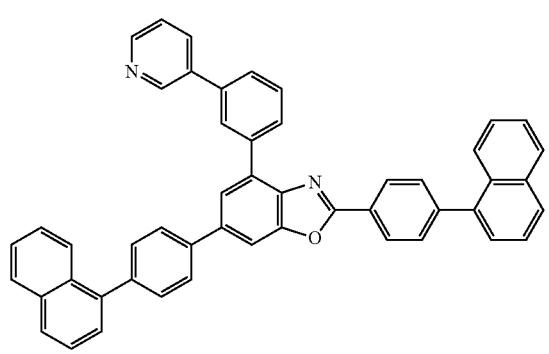
[Chemical Formula 121]
(1-115)
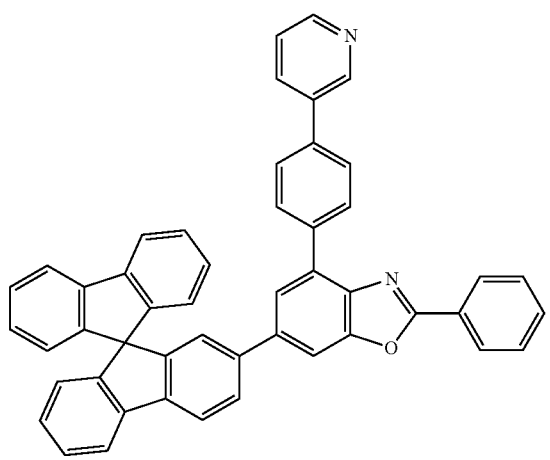
[Chemical Formula 122]
(1-116)
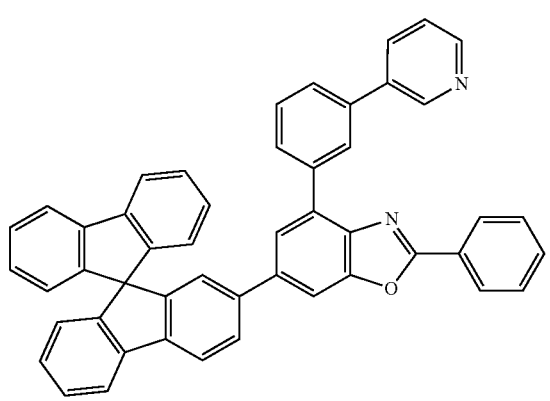
[Chemical Formula 123]
(1-117)
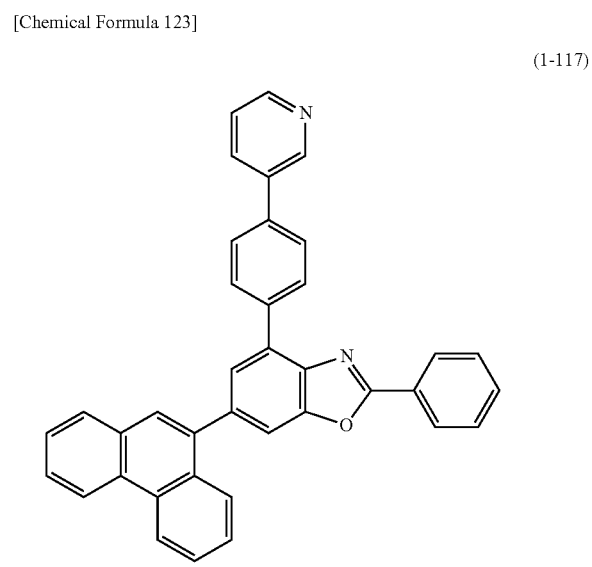
[Chemical Formula 124]
(1-118)
[Chemical Formula 125]
(1-119)
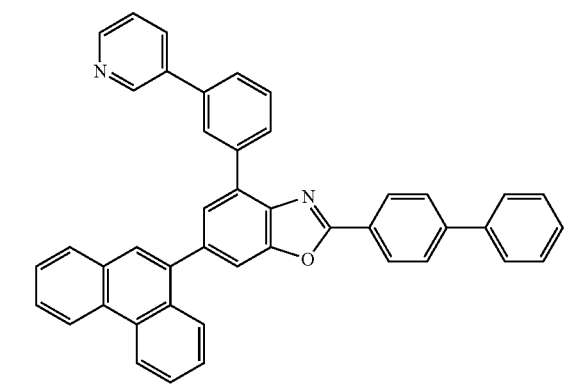

[Chemical Formula 126]
(1-120)
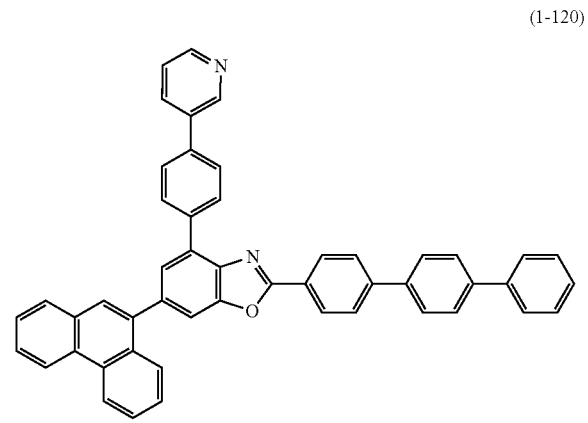
[Chemical Formula 127]
(1-121)
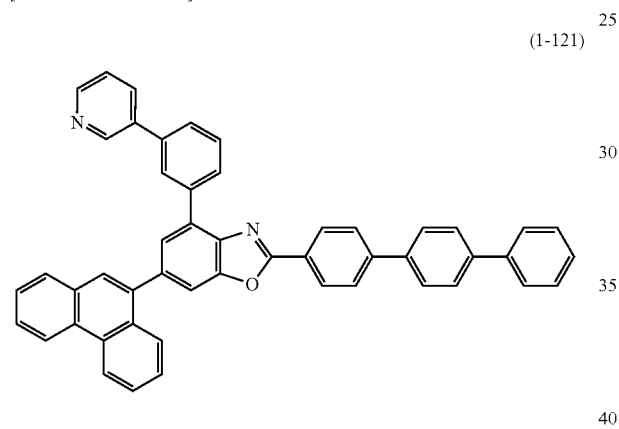
[Chemical Formula 128]
(1-122)
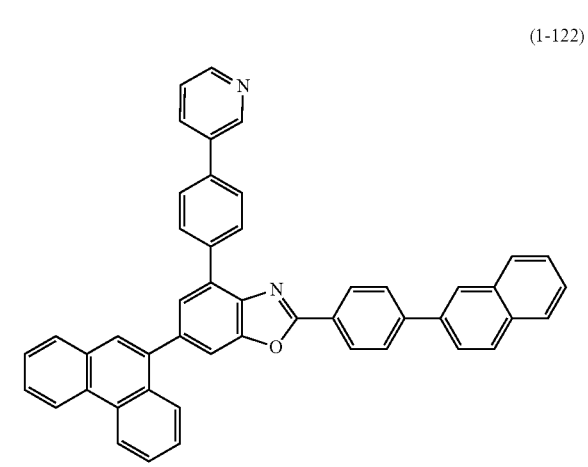
[Chemical Formula 129]
(1-123)
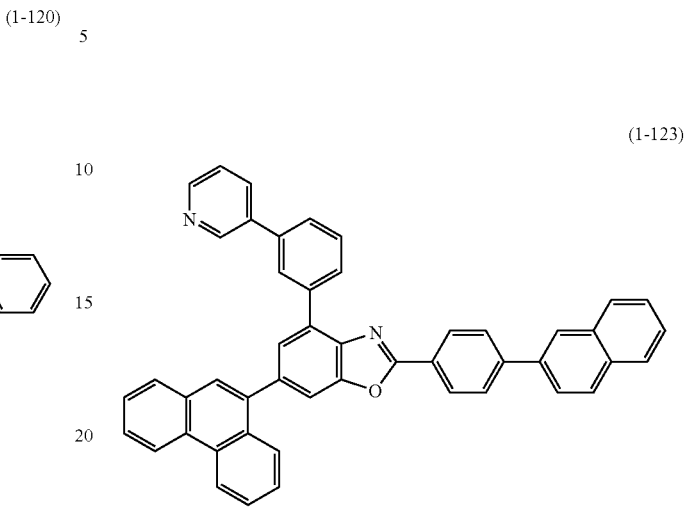
[Chemical Formula 130]
(1-124)
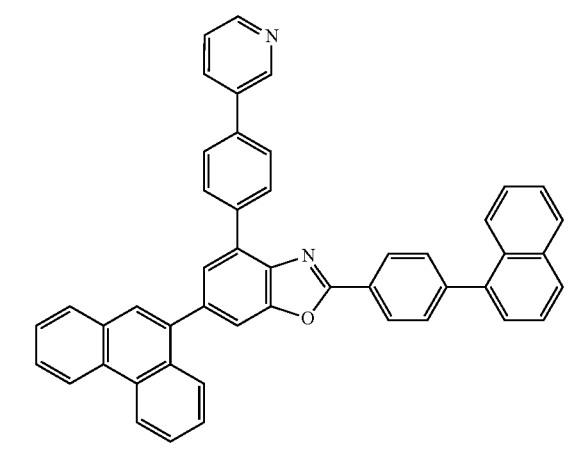

[Chemical Formula 131]
[Chemical Formula 132]
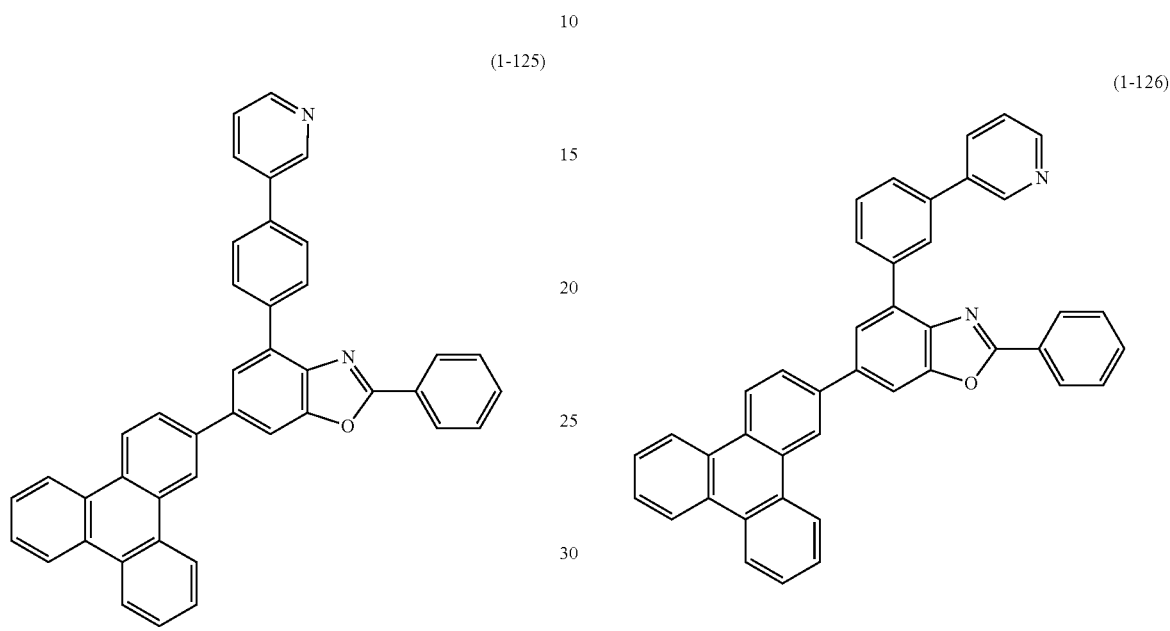
(1-125)
(1-126)
[Chemical Formula 133]
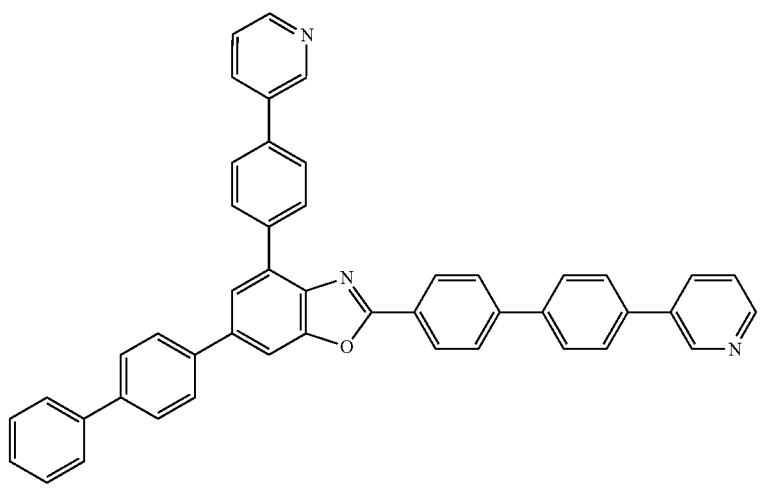
(1-127)

[Chemical Formula 134]
(1-128)
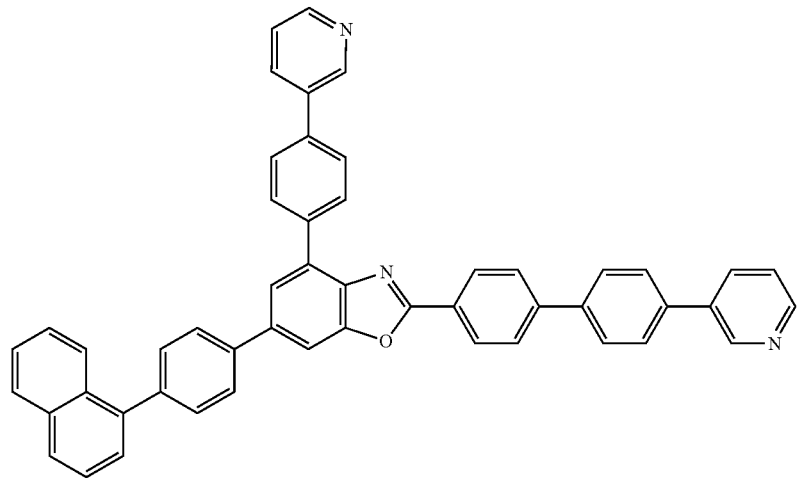
[Chemical Formula 135]
(1-129)
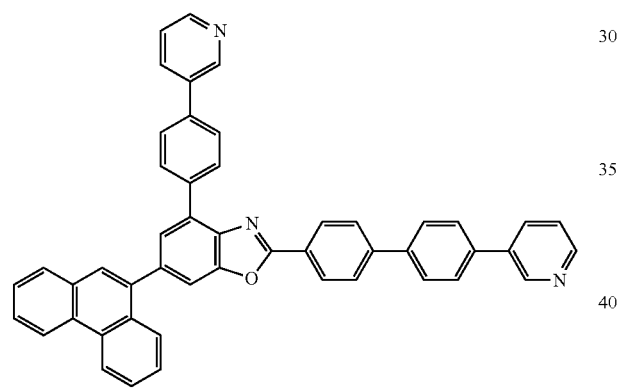
[Chemical Formula 136]
(1-130)
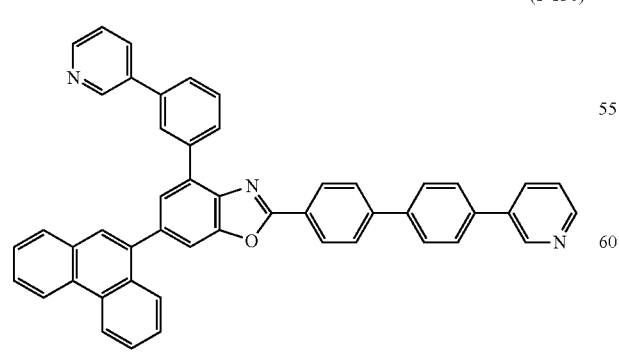

[Chemical Formula 137]
(1-131)
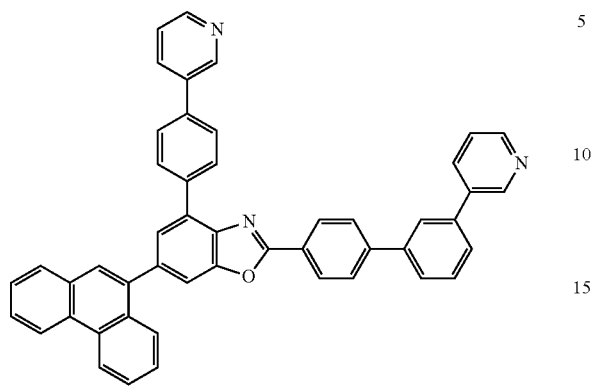
[Chemical Formula 138]
(1-132)
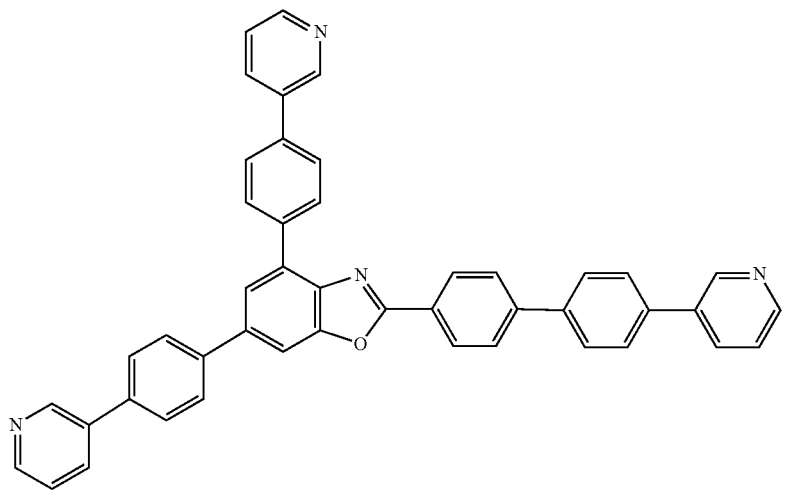
[Chemical Formula 139]
(1-133)
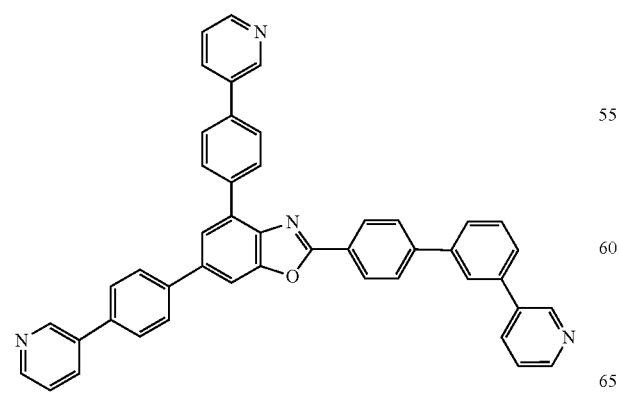

The following presents specific examples of preferred compounds among the benzothiazole compounds of the general formula (1) preferably used in the organic EL device of the present invention. The present invention, however, is not restricted to these compounds.
[Chemical Formula 140]
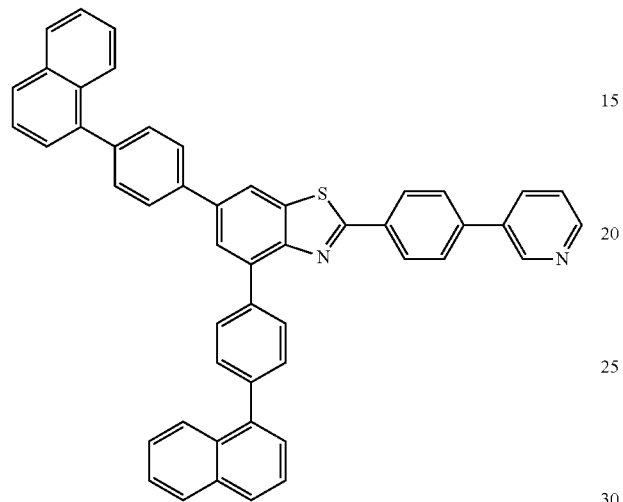
(2-1)
[Chemical Formula 141]
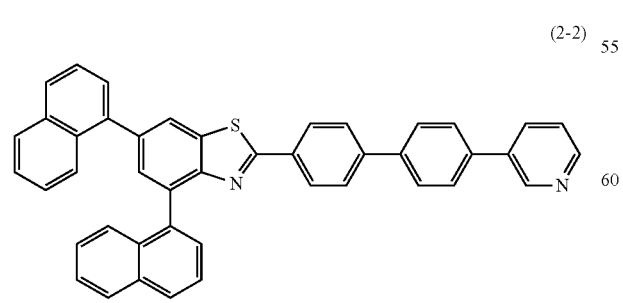
(2-2)
[Chemical Formula 142]
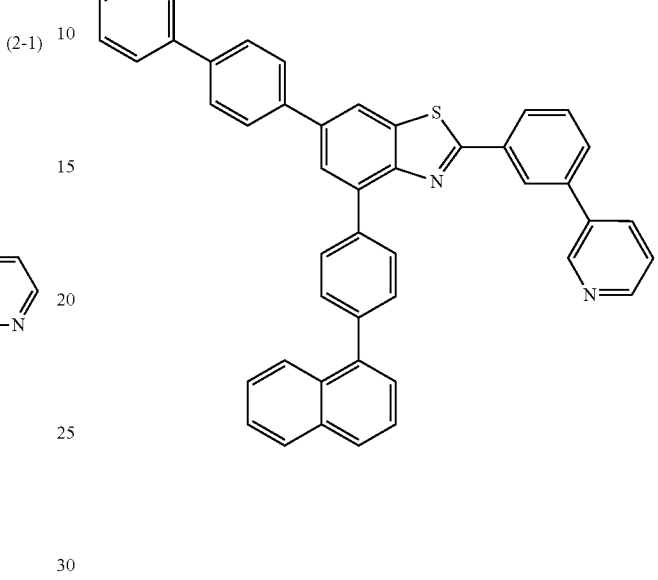
(2-3)
[Chemical Formula 143]
(2-4)

[Chemical Formula 144]
(2-5)
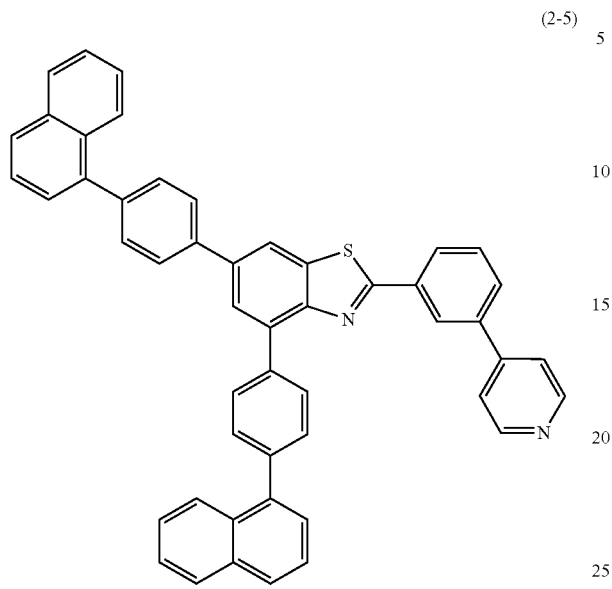
[Chemical Formula 145]
(2-6)
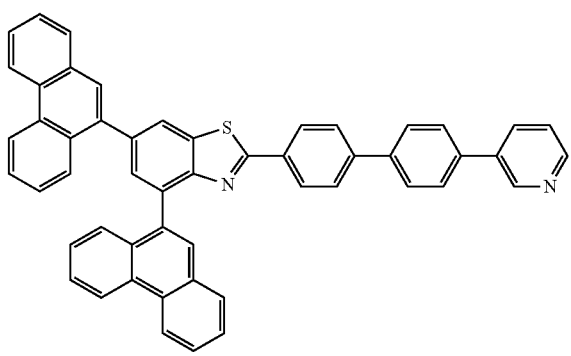
[Chemical Formula 146]
(2-7)
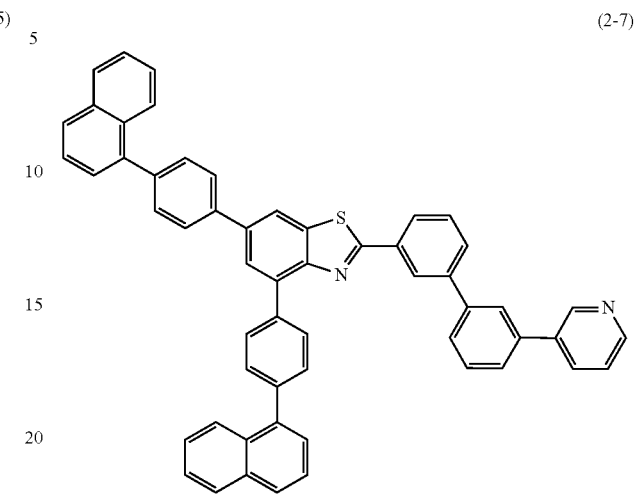
[Chemical Formula 147]
(2-8)
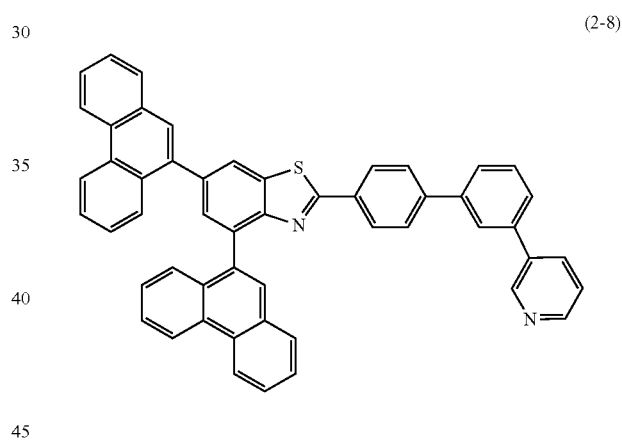
[Chemical Formula 148]
(2-9)
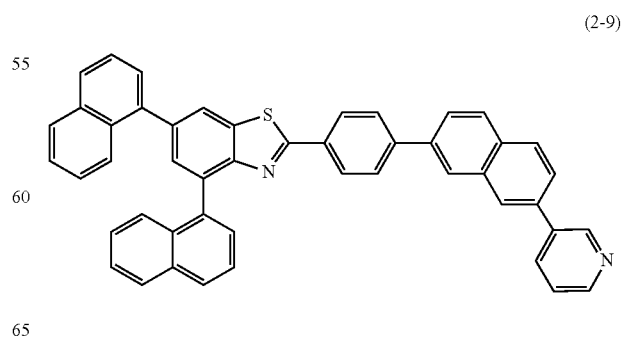

[Chemical Formula 149]
(2-10)
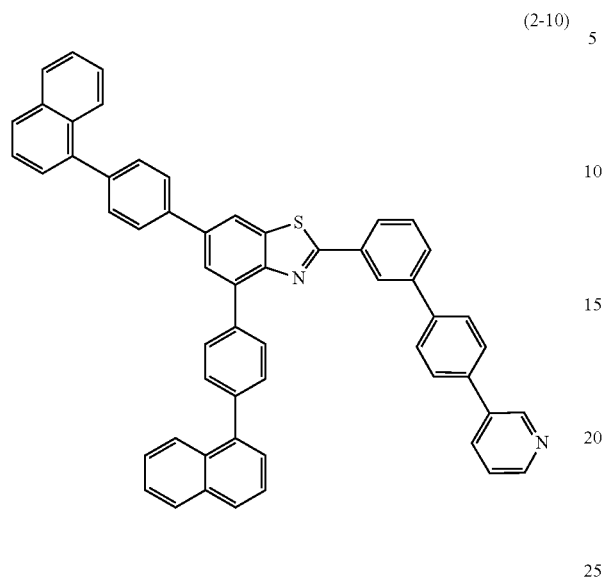
[Chemical Formula 150]
(2-11)
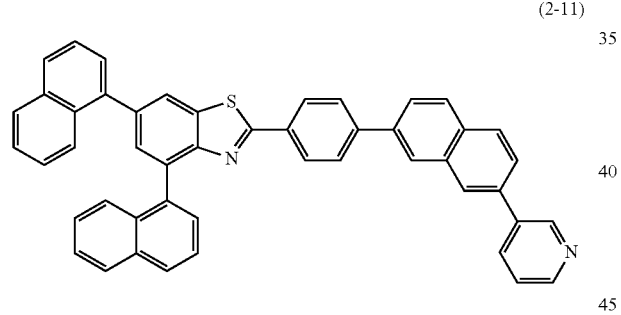
[Chemical Formula 151]
(2-12)
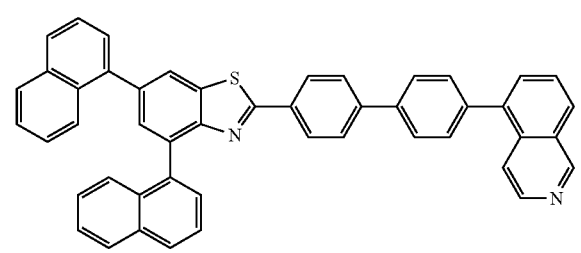
[Chemical Formula 152]
(2-13)
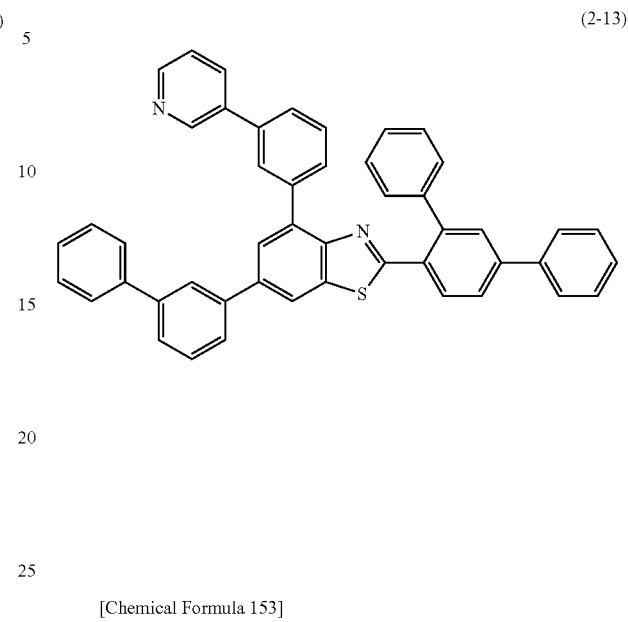
[Chemical Formula 153]
(2-14)
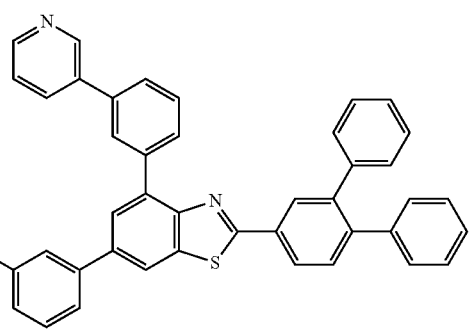
[Chemical Formula 154]
(2-15)

[Chemical Formula 155]
(2-16)
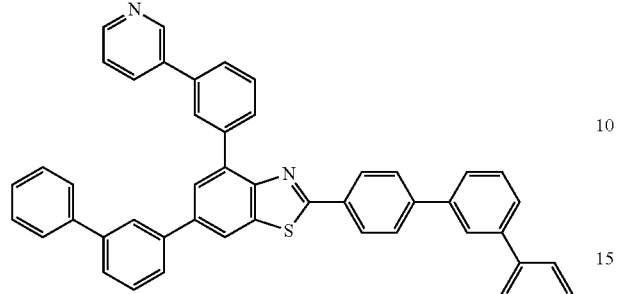
[Chemical Formula 156]
(2-17)
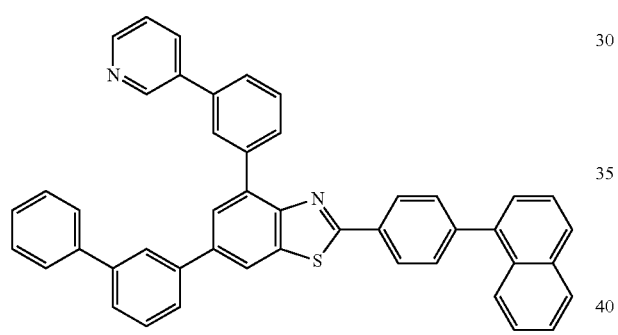
[Chemical Formula 157]
(2-18)
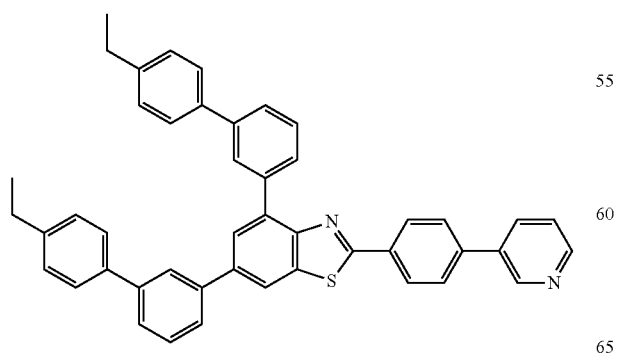
[Chemical Formula 158]
(2-19)
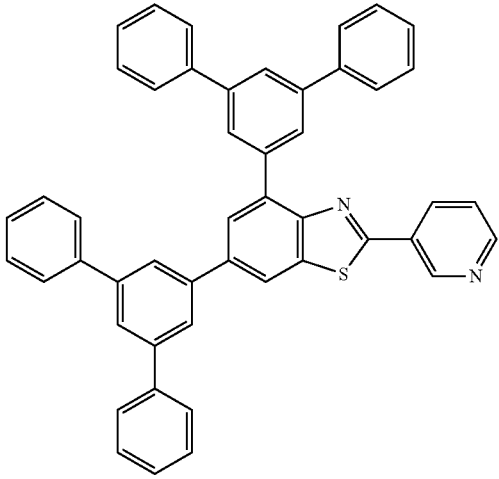
[Chemical Formula 159]
(2-20)
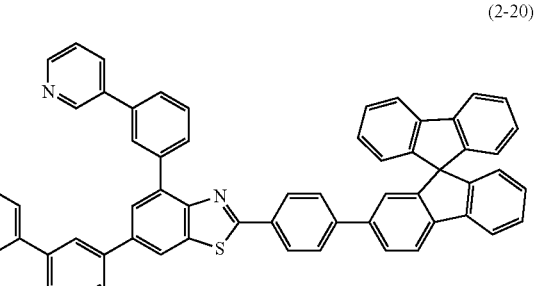
[Chemical Formula 160]
(2-21)
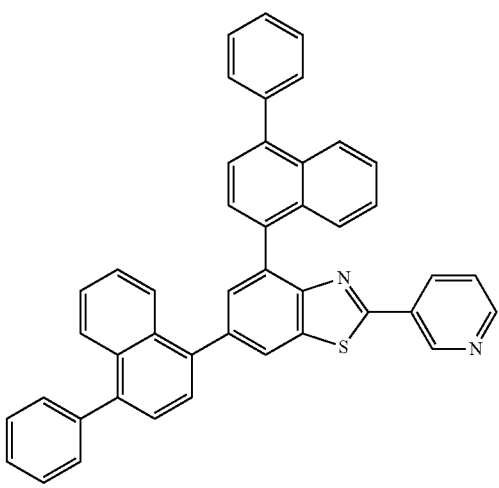

[Chemical Formula 161]
(2-22)
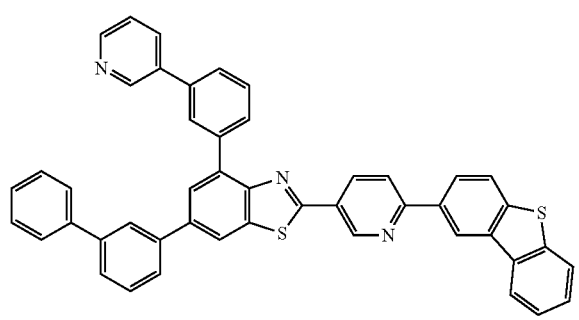
[Chemical Formula 162]
(2-23)
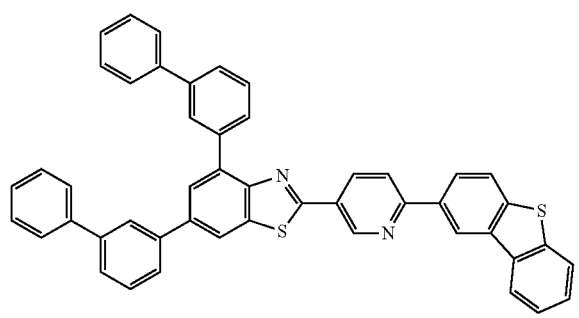
[Chemical Formula 163]
(2-24)
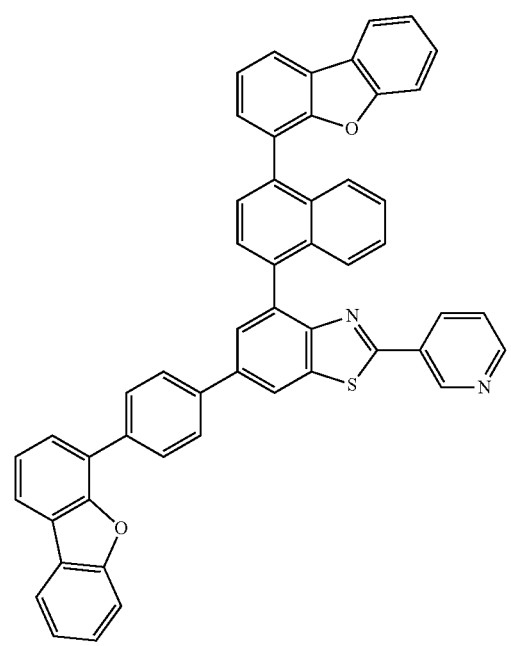
[Chemical Formula 164]
(2-25)
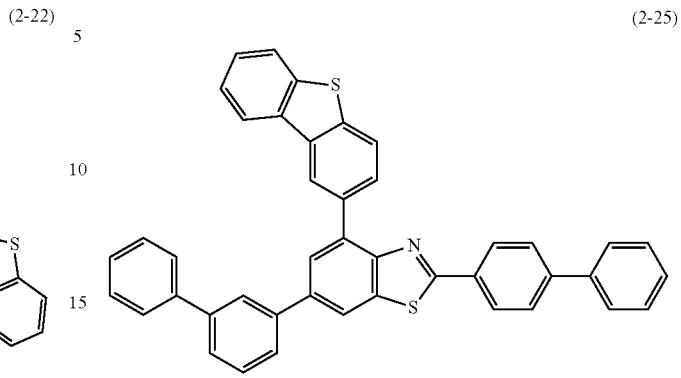
[Chemical Formula 165]
(2-26)
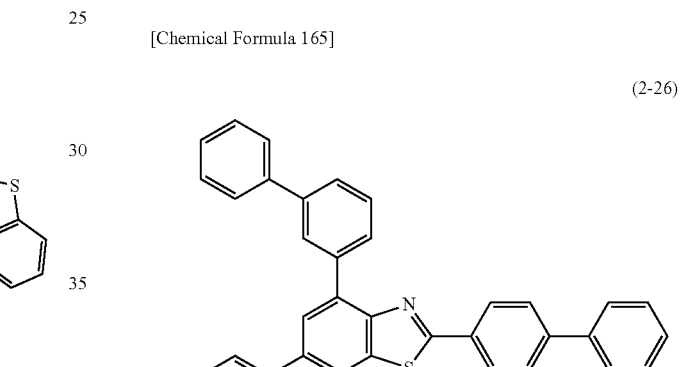
[Chemical Formula 166]
(2-27)
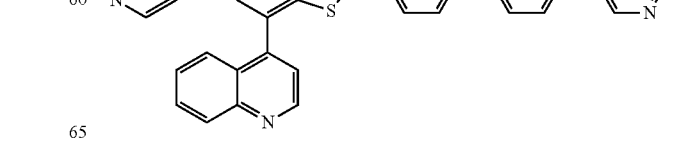

[Chemical Formula 167]
(2-28)
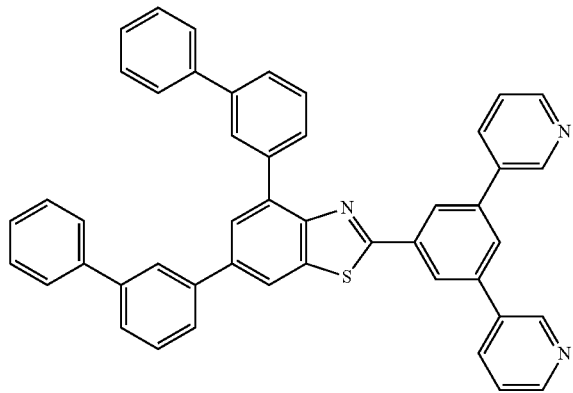
[Chemical Formula 170]
(2-31)
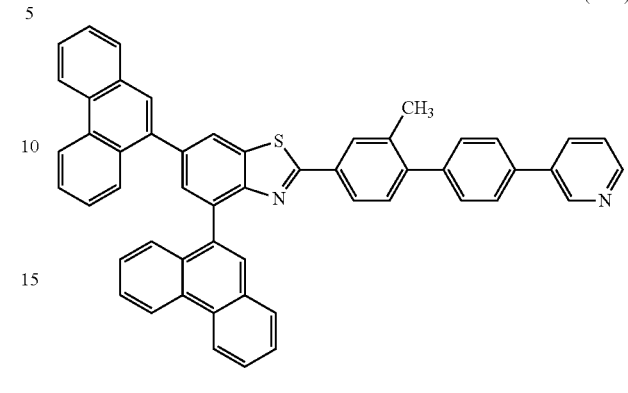
[Chemical Formula 167]
(2-29)
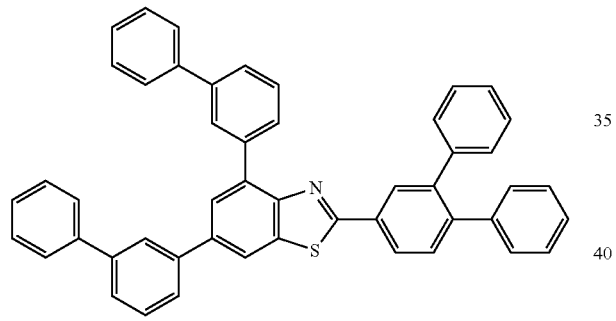
[Chemical Formula 171]
(2-32)
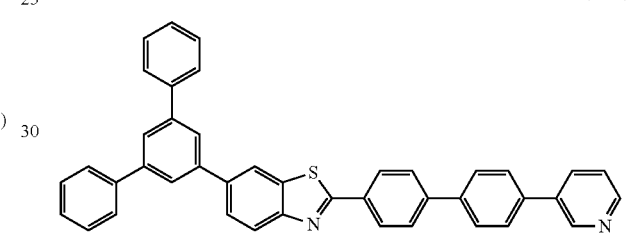
[Chemical Formula 172]
(2-33)
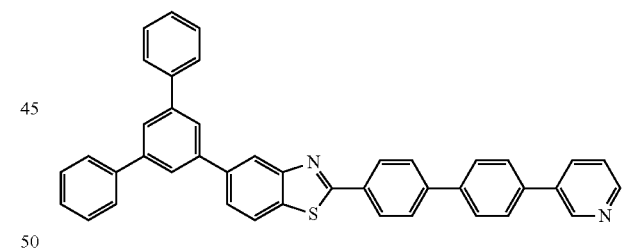
[Chemical Formula 169]
(2-30)
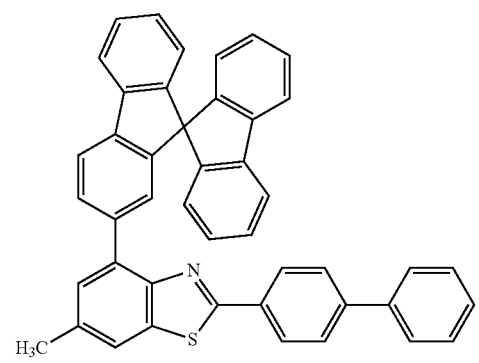
[Chemical Formula 173]
(2-34)
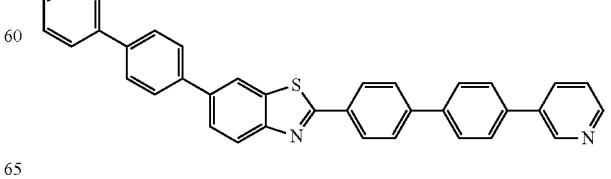

[Chemical Formula 174]
(2-35)
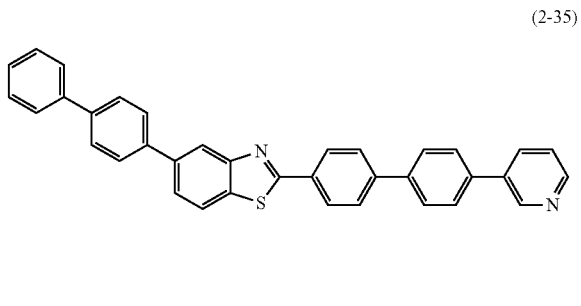
[Chemical Formula 175]
(2-36)
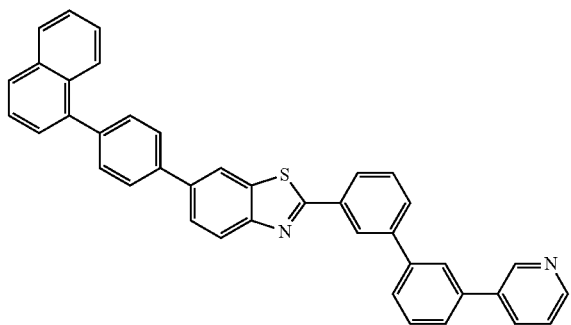
[Chemical Formula 176]
(2-37)
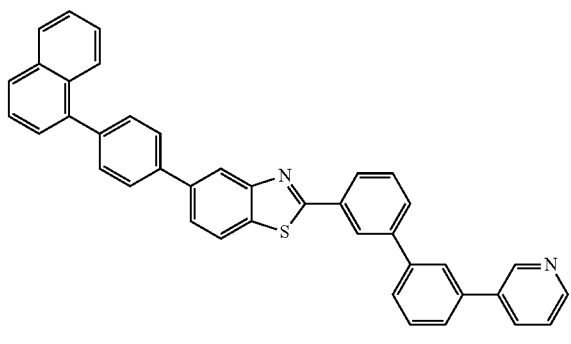
[Chemical Formula 177]
(2-38)
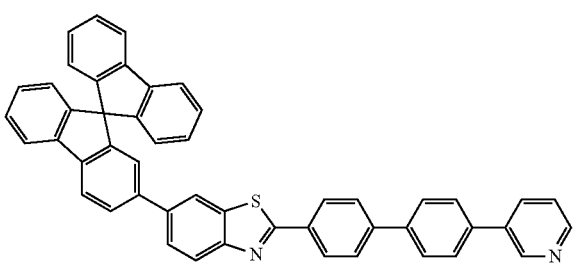
[Chemical Formula 178]
(2-39)
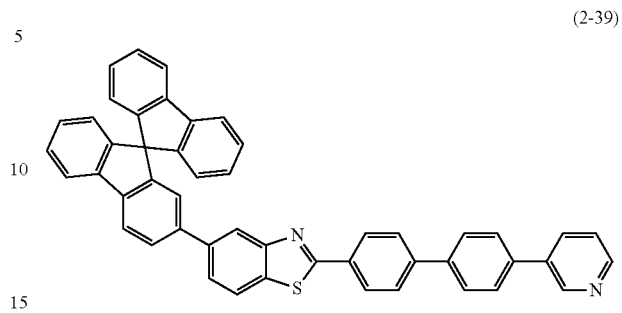
[Chemical Formula 179]
(2-40)
[Chemical Formula 180]
(2-41)
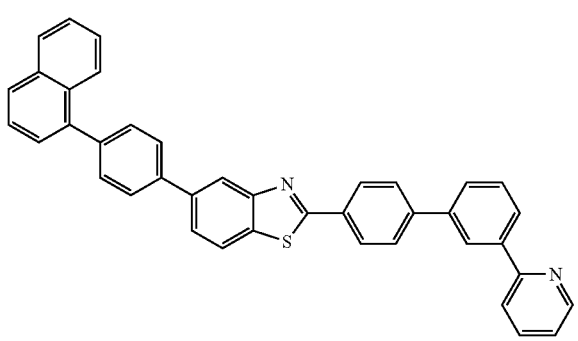

[Chemical Formula 181]
(2-42)
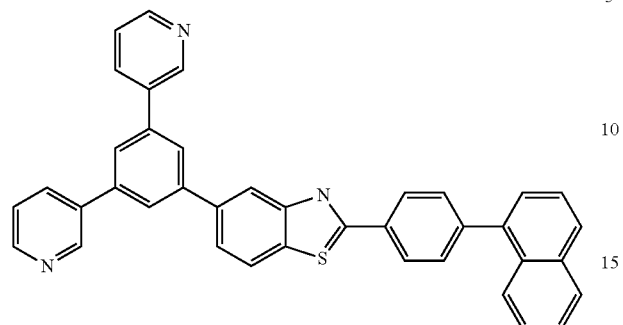
[Chemical Formula 182]
(2-43)
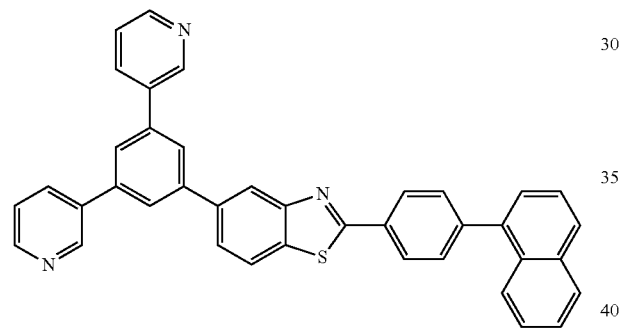
[Chemical Formula 183]
(2-44)
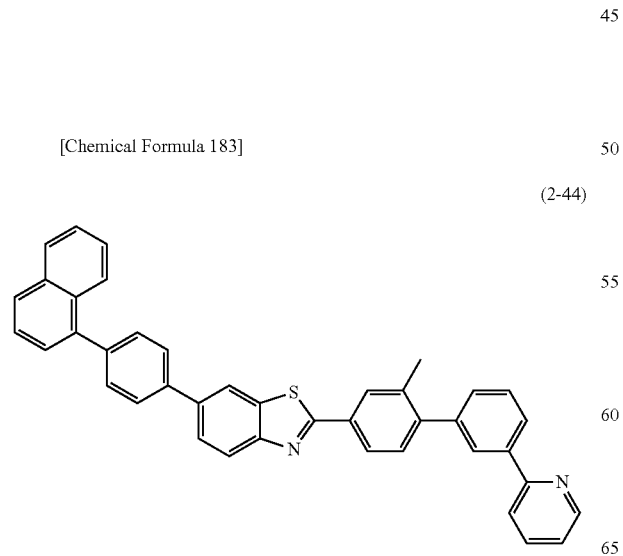
[Chemical Formula 184]
(2-45)
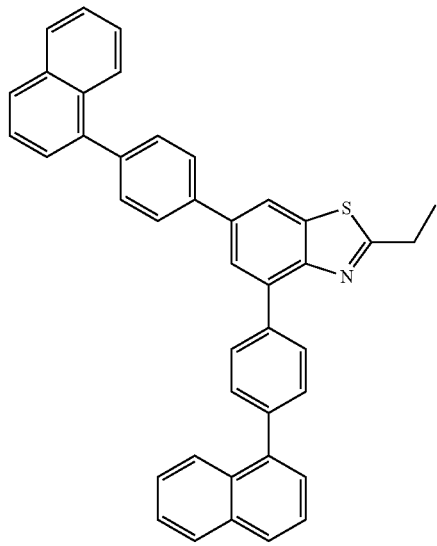
[Chemical Formula 185]
(2-46)
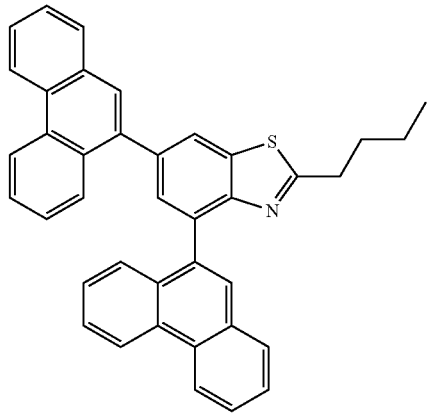

[Chemical Formula 186]
(2-47)
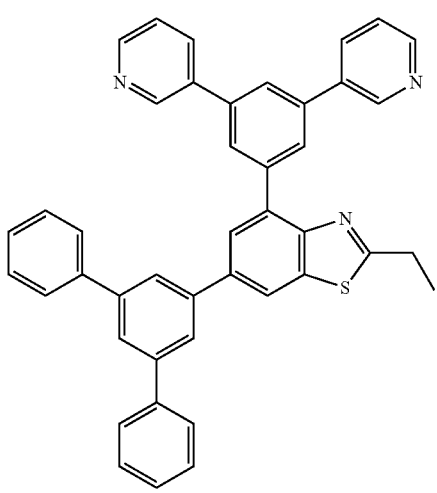
[Chemical Formula 187]
(2-48)
[Chemical Formula 188]
(2-49)
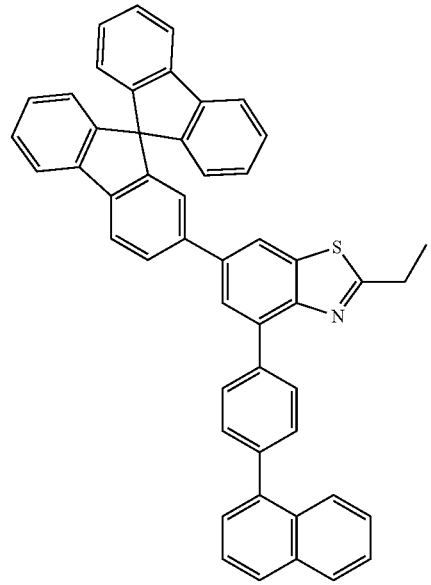
[Chemical Formula 189]
(2-50)
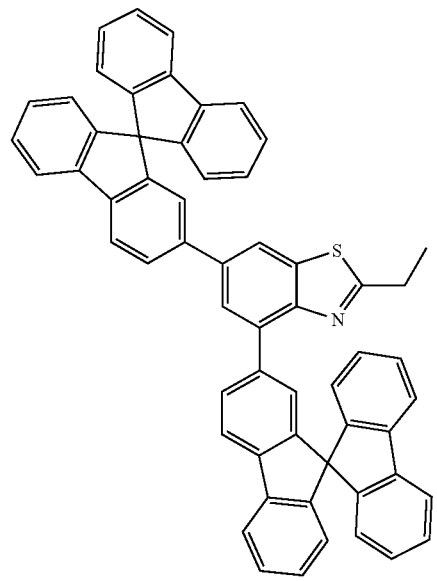

[Chemical Formula 190]
(2-51)
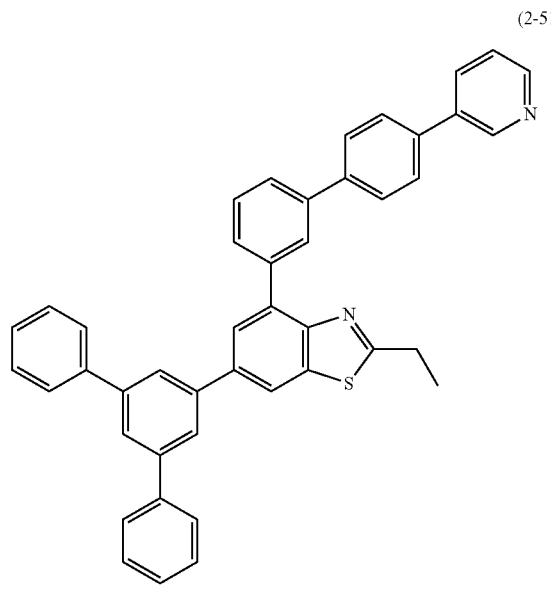
[Chemical Formula 192]
(2-53)
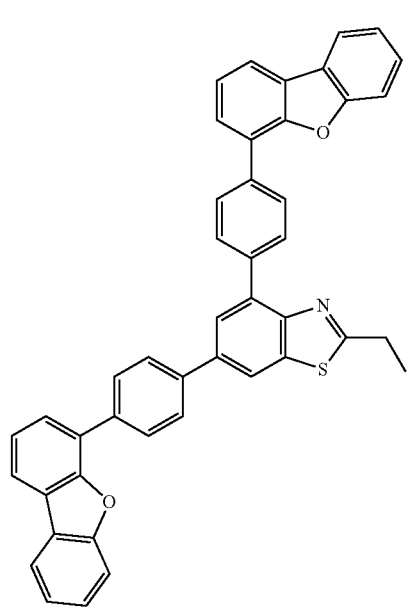
[Chemical Formula 191]
(2-52)
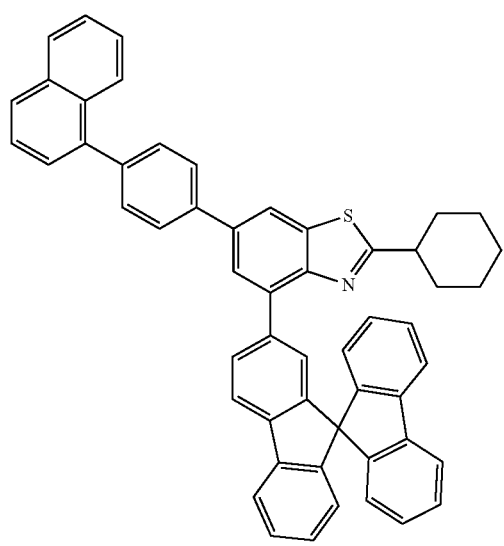
[Chemical Formula 193]
(2-54)
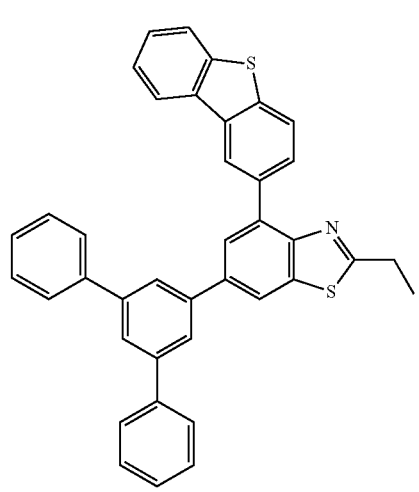

[Chemical Formula 194]
(2-55)
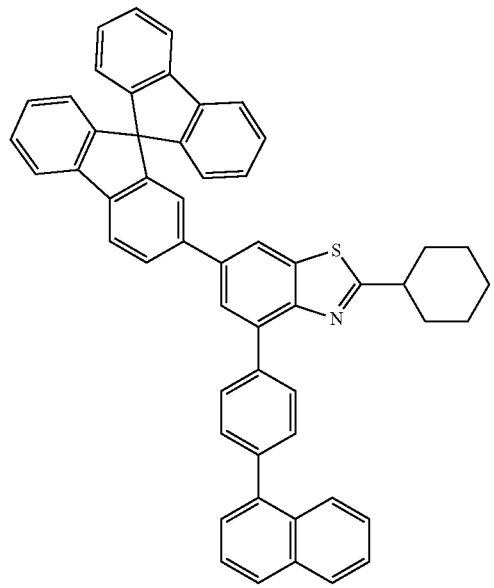
[Chemical Formula 195]
(2-56)
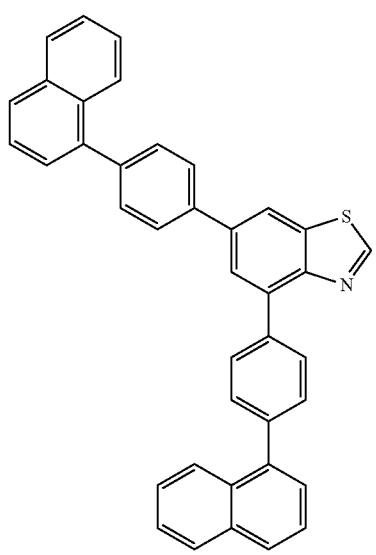
[Chemical Formula 196]
(2-57)
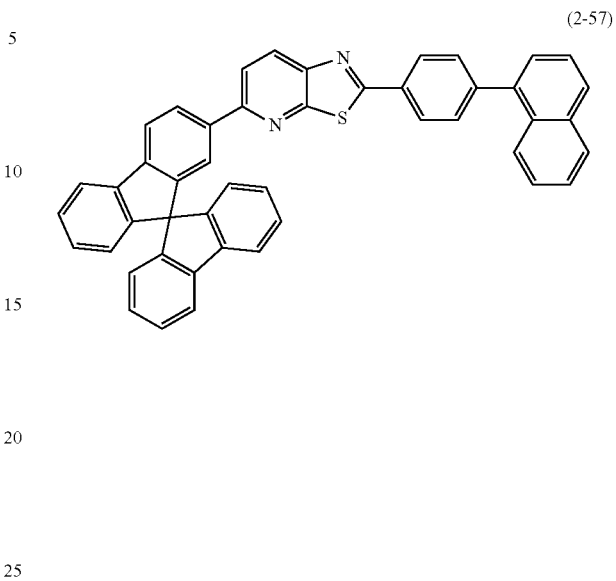
[Chemical Formula 197]
(2-58)
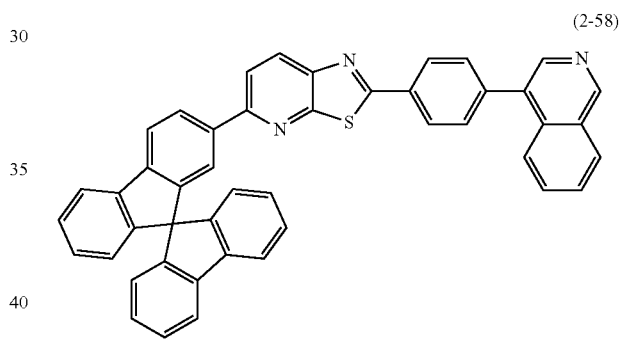
[Chemical Formula 198]
(2-59)
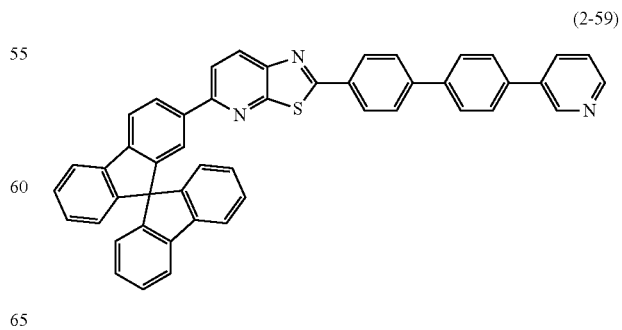

[Chemical Formula 199]

(2-60)

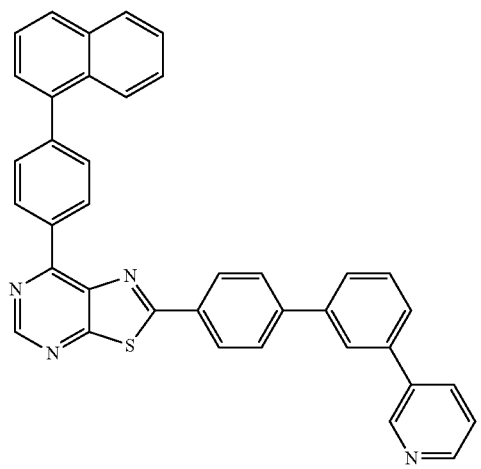

[Chemical Formula 200]

(2-61)

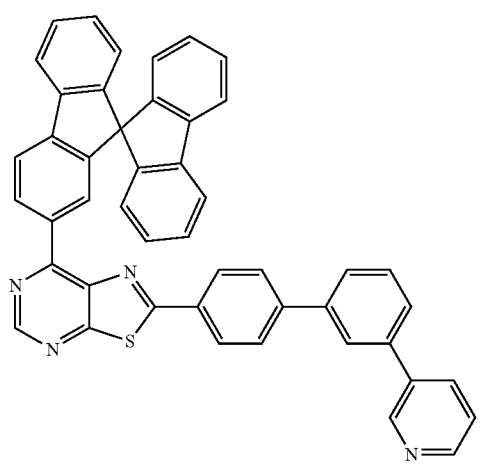

[Chemical Formula 201]

(2-62)

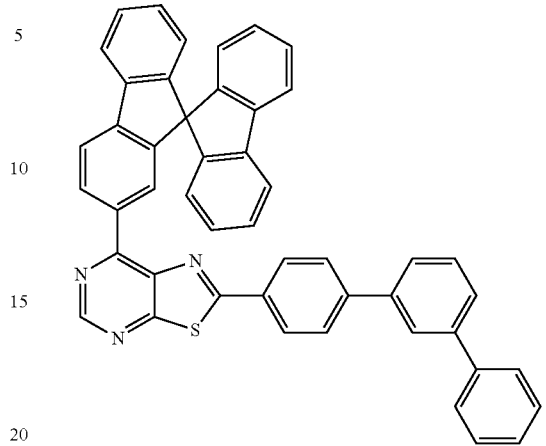

[Chemical Formula 202]

(2-63)

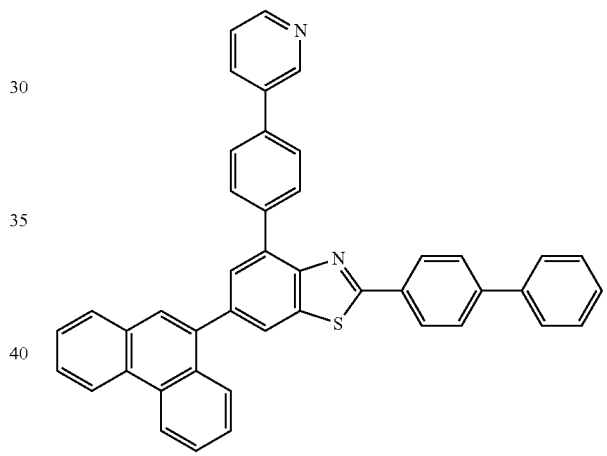

The compounds described above having an fused-azole ring structure can be synthesized by a known method (refer to PTLs 5 and 6, NPLs 6 and 7, for example).

The compounds having a fused-azole ring structure of the general formula (1) were purified by methods such as column chromatography, adsorption using, for example, a silica gel, activated carbon, or activated clay, recrystallization or crystallization using a solvent, and a sublimation purification method. The compounds were identified by an NMR analysis. A melting point, a glass transition point (Tg), and a work function were measured as material property values. The melting point can be used as an index of vapor deposition, the glass transition point (Tg) can be used as an index of stability in a thin-film state, and the work function can be used as an index of hole transportability and hole blocking performance.

Other compounds used for the organic EL device of the present invention were purified by methods such as column chromatography, adsorption using, for example, a silica gel, activated carbon, or activated clay, recrystallization or crystallization using a solvent, and a sublimation purification method, and finally purified by a sublimation purification method.

The melting point and the glass transition point (Tg) were measured by a high-sensitive differential scanning calorimeter (DSC3100SA produced by Bruker AXS) using powder.

For the measurement of the work function, a 100 nm-thick thin film was fabricated on an ITO substrate, and an ionization potential measuring device (PYS-202 produced by Sumitomo Heavy Industries, Ltd.) was used.

The organic EL device of the present invention may have a structure including an anode, a hole injection layer, a hole transport layer, a light emitting layer, an electron transport layer, an electron injection layer, and a cathode successively formed on a substrate, optionally with an electron blocking layer between the hole transport layer and the light emitting layer, and a hole blocking layer between the light emitting layer and the electron transport layer. Some of the organic layers in the multilayer structure may be omitted, or may serve more than one function. For example, a single organic layer may serve as the hole injection layer and the hole transport layer, or as the electron injection layer and the electron transport layer, and so on. Further, any of the layers may be configured to laminate two or more organic layers having the same function, and the hole transport layer may have a two-layer laminated structure, the light emitting layer may have a two-layer laminated structure, the electron transport layer may have a two-layer laminated structure, and so on.

An electrode material having a high work function, such as ITO and gold, may be used as the anode of the organic EL device of the present invention. The hole injection layer used of the organic EL device of the present invention may be a porphyrin compound, represented by copper phthalocyanine, and also may be a starburst type triphenylamine derivative, a triphenylamine trimer or tetramer, such as an arylamine compound having a structure containing in the molecule thereof three or more triphenylamine structures binding via a single bond or a divalent group containing no hetero atom, a heterocyclic compound having acceptor property, such as hexacyanoazatriphenylene, or a coating type polymer compound. These materials may be formed into a thin film by a vapor deposition method or other known methods such as a spin coating method and an inkjet method.

Examples of material used for the hole transport layer of the organic EL device of the present invention can be benzidine derivatives such as N,N'-diphenyl-N,N'-di(m-tolyl)-benzidine (hereinafter referred to as TPD), N,N'-diphenyl-N,N'-di(a-naphthyl)-benzidine (hereinafter referred to as NPD), and N,N,N',N'-tetrabiphenylylbenzidine; 1,1-bis[(di-4-tolylamino)phenyl]cyclohexane (TAPC); various triphenylamine trimers and tetramers. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. Examples of material used for the hole injection/transport layer can be coating-type polymer materials such as poly(3,4-ethylenedioxythiophene) (PEDOT)/poly(styrene sulfonate) (PSS). These materials may be formed into a thin-film by a vapor deposition method or other known methods such as a spin coating method and an inkjet method.

In the hole injection layer or the hole transport layer, a material that is ordinarily used in the layer p-doped with trisbromophenylamine hexachloro antimony, or the like, a polymer compound having a structure of a benzidine derivative, such as TPD, as a partial structure thereof, or the like may be used.

The electron blocking layer used of the organic EL device of the present invention may be a compound having an electron blocking capability, such as a carbazole derivative, such as 4,4',4''-tri(N-carbazolyl)triphenylamine (hereinafter referred to as TCTA), 9,9-bis[4-(carbazol-9-yl)phenyl]fluorene, 1,3-bis(carbazol-9-yl)benzene (hereinafter referred to as mCP), and 2,2-bis(4-carbazol-9-ylphenyl)adamantane (Ad-Cz), a compound having a triphenylsilyl group and a triarylamine structure, represented by 9-[4-(carbazol-9-yl)phenyl]-9-[4-(triphenylsilyl)phenyl]-9H-fluorene. These compounds each may be individually formed into a film, may be used as a single layer formed with another material mixed, or may be formed into a laminated structure containing the individually formed layers, a laminated structure containing the layers with another material mixed, or a laminated structure containing the individually formed layer and the layer with another material mixed. These materials may be formed into a thin film by a vapor deposition method or other known methods such as a spin coating method and an inkjet method.

Examples of material used for the light emitting layer of the organic EL device of the present invention can be various metal complexes including, for example, quinolinol derivative metal complexes such as $Alq_3$; anthracene derivatives; bis(styryl)benzene derivatives; pyrene derivatives; oxazole derivatives; and polyparaphenylene vinylene derivatives; in addition to the compounds having a fused-azole ring structure of the present invention. Further, the light emitting layer may be made of a host material and a dopant material. Examples of the host material can be the above light-emitting materials, thiazole derivatives, benzimidazole derivatives, and polydialkyl fluorene derivatives, in addition to the compounds having a fused-azole ring structure of the present invention and the compounds having a pyridoindole ring structure. Examples of the dopant material can be quinacridone, coumarin, rubrene, perylene, derivatives thereof, benzopyran derivatives, rhodamine derivatives, and aminostyryl derivatives. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer.

Further, the light-emitting material may be a phosphorescent material. Phosphorescent materials as metal complexes such as iridium and platinum may be used. Examples of the phosphorescent materials include green phosphorescent materials such as Ir(ppy)3, blue phosphorescent materials such as FIrpic and FIr6, and red phosphorescent materials such as $Btp_2Ir(acac)$. Here, carbazole derivatives such as 4,4'-di(N-carbazolyl)biphenyl (CBP), TCTA, and mCP may be used as the hole injecting and transporting host material, in addition to the compounds having a fused-azole ring structure of the present invention and the compounds having a pyridoindole ring structure. Compounds such as p-bis(triphenylsilyl)benzene (UGH2) and 2,2',2''-(1,3,5-phenylene)-tris(1-phenyl-1H-benzimidazole) (TPBI) may be used as the electron transporting host material. In this way, a high-performance organic EL device can be produced.

In order to avoid concentration quenching, the doping of the host material with the phosphorescent light emitting material is preferably made by co-evaporation in a range of 1 to 30% by weight with respect to the total light emitting layer.

Further, Examples of the light emitting material may be delayed fluorescent-emitting material such as a CDCB derivative of PIC-TRZ, CC2TA, PXZ-TRZ, 4CzIPN or the like (refer to NPL 3, for example).

These materials may be formed into a thin film by using a vapor deposition method or other known methods such as a spin coating method and an inkjet method.

The hole blocking layer of the organic EL device of the present invention may be formed by using hole blocking compounds such as the metal complexes of phenanthroline derivatives such as bathocuproin (hereinafter referred to as BCP), the metal complexes of quinolinol derivatives such as BAlq, various rare earth complexes, oxazole derivatives, triazole derivatives, and triazine derivatives, in addition to the compounds having a fused-azole ring structure of the present invention. These materials may also serve as the material of the electron transport layer. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. These materials may be formed into a thin-film by using a vapor deposition method or other known methods such as a spin coating method and an inkjet method.

The electron transport layer of the organic EL device of the present invention may be formed by using metal complexes of quinolinol derivatives such as $Alq_3$ and BAlq, various metal complexes, triazole derivatives, triazine derivatives, oxadiazole derivatives, pyridine derivatives, benzimidazole derivatives, thiadiazole derivatives, anthracene derivatives, carbodiimide derivatives, quinoxaline derivatives, Pyridoindole derivatives, phenanthroline derivatives, and silole derivatives, in addition to the compounds of having a fused-azole ring structure of the present invention. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. These materials may be formed into a thin-film by using a vapor deposition method or other known methods such as a spin coating method and an inkjet method.

Examples of material used for the electron injection layer of the organic EL device of the present invention can be alkali metal salts such as lithium fluoride and cesium fluoride; alkaline earth metal salts such as magnesium fluoride; a metal complex of a quinolinol derivative such as lithium quinolinol; and metal oxides such as aluminum oxide; in addition to the compounds having a fused-azole ring structure of the present invention. However, the electron injection layer may be omitted in the preferred selection of the electron transport layer and the cathode.

Further, in the electron injection layer or the electron transport layer, a material obtained by further N-doping a material which is commonly used for the layer with a metal such as cecium, or the like can be used.

The cathode of the organic EL device of the present invention may be made of an electrode material with a low work function such as aluminum, or an alloy of an electrode material with an even lower work function such as a magnesium-silver alloy, a magnesium-indium alloy, or an aluminum-magnesium alloy.

The following describes an embodiment of the present invention in more detail based on Examples. The present invention, however, is not restricted to the following Examples, as long as such departures are within the scope of the invention.

Example 1

Synthesis of 4,6-bis(4-naphthalene-1-yl-phenyl)-2-(4-pyridine-3-yl-phenyl)-benzoxazole (Compound 1-1)

2-(4-chlorophenyl)-4,6-bis(4-naphthalene-1-yl-phenyl)-benzoxazole (4.5 g), 3-pyridylboronic acid (1.0 g), bis(dibenzylideneacetone)palladium(0) (0.32 g), tricyclohexylphosphine (0.4 g), and tripotassium phosphate (4.7 g) were added into reaction vessel. The mixture was refluxed for overnight while stirring. After cooling, an organic layer was collected by liquid separation, and ethyl acetate were added to the aqueous layer for extraction. The collected organic layer was concentrated, and then the resulting crude product was purified by column chromatography (support: silica gel, eluent: dichloromethane/ethyl acetate), and the crystallization with a dichloromethane/methanol mixed solvent whereby a white powder of 4,6-bis(4-naphthalene-1-yl-phenyl)-2-(4-pyridine-3-yl-phenyl)-benzoxazole (Compound 1-1; 1.8 g; yield: 38%) was obtained.

[Chemical Formula 203]

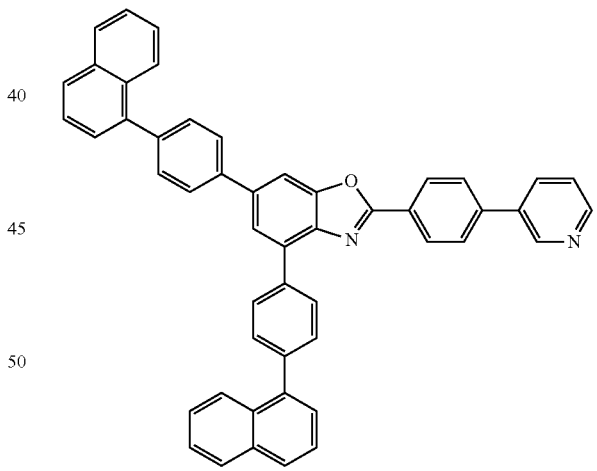

(1-1)

The structure of the obtained white powder was identified by NMR.

$^1$H-NMR ($CDCl_3$) detected 32 hydrogen signals, as follows.

δ(ppm)=8.98 (1H), 8.68 (1H), 8.52 (2H), 8.34 (2H), 8.12 (1H), 8.07-7.89 (10H), 7.82 (2H), 7.76 (2H), 7.69 (2H), 7.64 (9H).

Example 2

Synthesis of 2-{4'-(pyridine-3-yl)-1,1'-biphenyl-4-yl}-4,6-di(naphthalene-1-yl)-benzoxazole (Compound 1-2)

The reaction was carried out under the same conditions as those of Example 1, except that 2-(4-chlorophenyl)-4,6-bis(4-naphthalene-1-yl-phenyl)-benzoxazole was replaced with 2-(4-chlorophenyl)-4,6-di(naphthalene-1-yl)-benzoxazole, and 3-pyridylboronic acid was replaced with 4-(pyridine-3-yl)-phenylboronic acid, whereby a white powder of 2-{4'-(pyridine-3-yl)-1,1'-biphenyl-4-yl}-4,6-di(naphthalene-1-yl)-benzoxazole (Compound 1-2; 2.1 g; yield: 34%) was obtained.

[Chemical Formula 204]

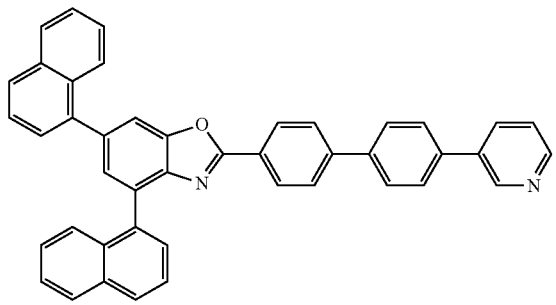

(1-2)

The structure of the obtained white powder was identified by NMR.

$^1$H-NMR (CDCl$_3$) detected 28 hydrogen signals, as follows.

δ(ppm)=8.94 (1H), 8.64 (1H), 8.35 (2H), 8.13 (1H), 8.05-7.91 (6H), 7.85 (1H), 7.82-7.76 (5H), 7.72 (2H), 7.68 (2H), 7.64-7.38 (7H).

Example 3

Synthesis of 4,6-bis(4-naphthalene-1-yl-phenyl)-2-(3-pyridine-3-yl-phenyl)-benzoxazole (Compound 1-3)

The reaction was carried out under the same conditions as those of Example 1, except that 2-(4-chlorophenyl)-4,6-bis(4-naphthalene-1-yl-phenyl)-benzoxazole was replaced with 2-(3-chlorophenyl)-4,6-bis(4-naphthalene-1-yl-phenyl)-benzoxazole, and bis(dibenzylideneacetone)palladium(0) was replaced with tris(dibenzylideneacetone)palladium(0), whereby a white powder of 4,6-bis(4-naphthalene-1-yl-phenyl)-2-(3-pyridine-3-yl-phenyl)-benzoxazole (Compound 1-3; 3.6 g; yield: 48%) was obtained.

[Chemical Formula 205]

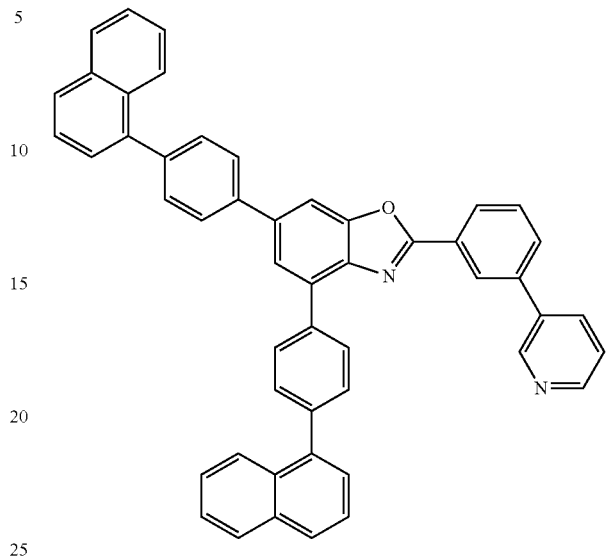

(1-3)

The structure of the obtained white powder was identified by NMR.

$^1$H-NMR (CDCl$_3$) detected 32 hydrogen signals, as follows.

δ(ppm)=9.01 (1H), 8.69 (1H), 8.60 (1H), 8.43 (1H), 8.32 (2H), 8.11 (1H), 8.07-8.01 (3H), 7.98-7.88 (7H), 7.83-7.67 (6H), 7.62-7.42 (9H).

Example 4

Synthesis of 2-{3'-(pyridine-3-yl)-1,1'-biphenyl-4-yl}-4,6-di(naphthalene-1-yl)-benzoxazole (Compound 1-4)

The reaction was carried out under the same conditions as those of Example 1, except that 2-(4-chlorophenyl)-4,6-bis(4-naphthalene-1-yl-phenyl)-benzoxazole was replaced with 2-(4-chlorophenyl)-4,6-di(naphthalene-1-yl)-benzoxazole, and 3-pyridylboronic acid was replaced with 3-(pyridine-3-yl)-phenylboronic acid, and bis(dibenzylideneacetone)palladium(0) was replaced with tris(dibenzylideneacetone)palladium(0), whereby a white powder of 2-{3'-(pyridine-3-yl)-1,1'-biphenyl-4-yl}-4,6-di(naphthalene-1-yl)-benzoxazole (Compound 1-4; 4.4 g; yield: 71%) was obtained.

[Chemical Formula 206]

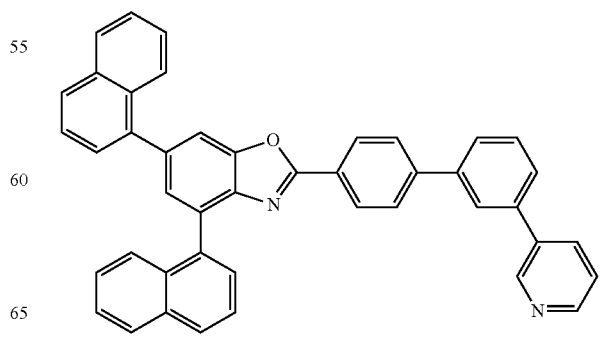

(1-4)

The structure of the obtained white powder was identified by NMR.

¹H-NMR (CDCl₃) detected 28 hydrogen signals, as follows.

δ(ppm)=8.94 (1H), 8.65 (1H), 8.36 (2H), 8.21 (1H), 8.05-7.92 (6H), 7.85 (2H), 7.83-7.76 (3H), 7.75-7.74 (12H).

Example 5

Synthesis of 2-(3-pyridine-4-yl-phenyl)-4,6-bis(4-naphthalene-1-yl-phenyl)-benzoxazole (Compound 1-5)

The reaction was carried out under the same conditions as those of Example 1, except that 2-(4-chlorophenyl)-4,6-bis(4-naphthalene-1-yl-phenyl)-benzoxazole was replaced with 2-(3-chlorophenyl)-4,6-bis(4-naphthalene-1-yl-phenyl)-benzoxazole, and 3-pyridylboronic acid was replaced with 4-pyridylboronic acid, and bis(dibenzylideneacetone)palladium(0) was replaced with tris(dibenzylideneacetone)palladium(0), whereby a white powder of 2-(3-pyridine-4-yl-phenyl)-4,6-bis(4-naphthalene-1-yl-phenyl)-benzoxazole (Compound 1-5; 3.0 g; yield: 40%) was obtained.

[Chemical Formula 207]

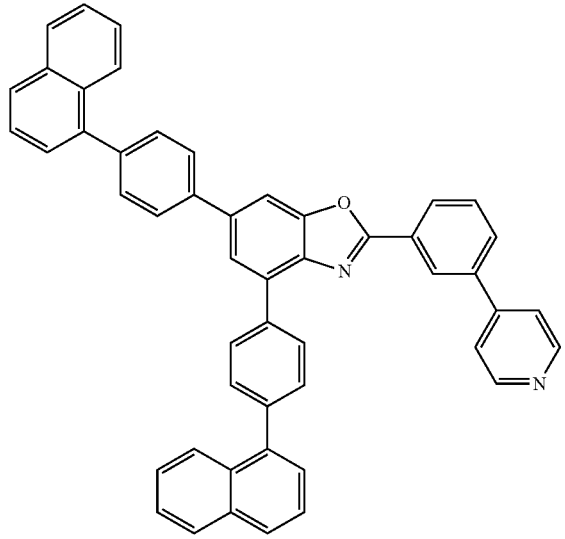

(1-5)

The structure of the obtained white powder was identified by NMR.

¹H-NMR (CDCl₃) detected 32 hydrogen signals, as follows.

δ(ppm)=8.76 (2H), 8.66 (1H), 8.47 (1H), 8.32 (2H), 8.11 (1H), 8.07-8.02 (2H), 7.99-7.89 (7H), 7.85 (1H), 7.78-7.48 (15H).

Example 6

Synthesis of 2-{4'-(pyridine-3-yl)-1,1'-biphenyl-4-yl}-4,6-di(phenanthrene-9-yl)-benzoxazole (Compound 1-6)

The reaction was carried out under the same conditions as those of Example 1, except that 2-(4-chlorophenyl)-4,6-bis(4-naphthalene-1-yl-phenyl)-benzoxazole was replaced with 2-(4-chlorophenyl)-4,6-di(phenanthrene-9-yl)-benzoxazole, and 3-pyridylboronic acid was replaced with 4-(pyridine-3-yl)phenylboronic acid, and bis(dibenzylideneacetone)palladium(0) was replaced with tris(dibenzylideneacetone)palladium(0), whereby a white powder of 2-{4'-(pyridine-3-yl)-1,1'-biphenyl-4-yl}-4,6-di(phenanthrene-9-yl)-benzoxazole (Compound 1-6; 2.1 g; yield: 17%) was obtained.

[Chemical Formula 208]

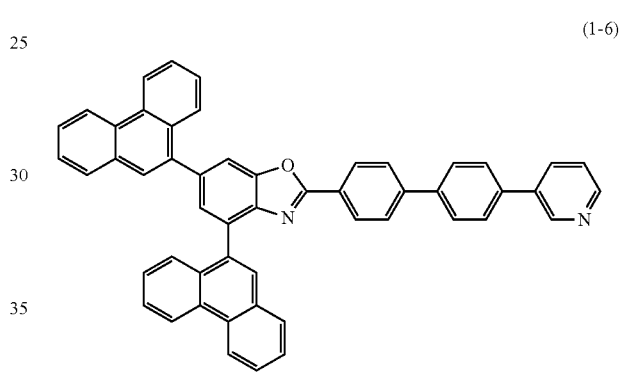

(1-6)

The structure of the obtained white powder was identified by NMR.

¹H-NMR (CDCl₃) detected 32 hydrogen signals, as follows.

δ(ppm)=8.93 (1H), 8.87-8.63 (4H), 8.62 (1H), 8.33 (2H), 8.18 (1H), 8.08-7.88 (7H), 7.80-7.55 (15H), 7.40 (1H).

Example 7

Synthesis of 2-{3'-(pyridine-3-yl)-1,1'-biphenyl-3-yl}-4,6-bis(4-naphthalene-1-yl-phenyl)-benzoxazole (Compound 1-7)

The reaction was carried out under the same conditions as those of Example 1, except that 2-(4-chlorophenyl)-4,6-bis(4-naphthalene-1-yl-phenyl)-benzoxazole was replaced with 2-(3-chlorophenyl)-4,6-bis(4-naphthalene-1-yl-phenyl)-benzoxazole, and 3-pyridylboronic acid was replaced with 3-(pyridine-3-yl)phenylboronic acid, and bis(dibenzylideneacetone)palladium(0) was replaced with tris(dibenzylideneacetone)palladium(0), whereby a white powder of 2-{3'-(pyridine-3-yl)-1,1'-biphenyl-3-yl}-4,6-bis(4-naphthalene-1-yl-phenyl)-benzoxazole (Compound 1-7; 2.0 g; yield: 27%) was obtained.

[Chemical Formula 209]

(1-7)

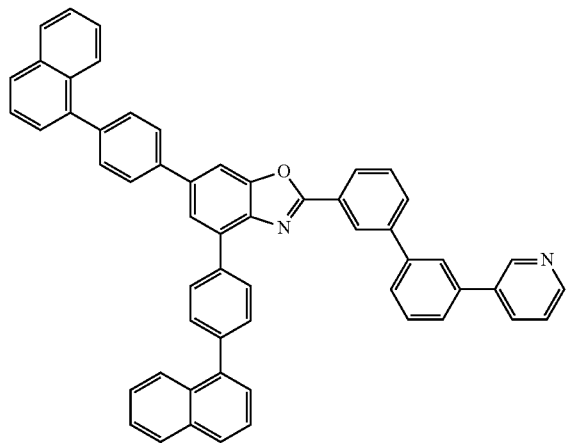

The structure of the obtained white powder was identified by NMR.

¹H-NMR (CDCl₃) detected 36 hydrogen signals, as follows.

δ(ppm)=8.98 (1H), 8.68-8.61 (2H), 8.42 (1H), 8.32 (2H), 8.15-7.40 (30H).

Example 8

Synthesis of 2-{3'-(pyridine-3-yl)-1,1'-biphenyl-4-yl}-4,6-di(phenanthrene-9-yl)-benzoxazole (Compound 1-8)

The reaction was carried out under the same conditions as those of Example 1, except that 2-(4-chlorophenyl)-4,6-bis(4-naphthalene-1-yl-phenyl)-benzoxazole was replaced with 2-(4-chlorophenyl)-4,6-di(phenanthrene-9-yl)-benzoxazole, and 3-pyridylboronic acid was replaced with 3-(pyridine-3-yl)phenylboronic acid, and bis(dibenzylideneacetone)palladium(0) was replaced with tris(dibenzylideneacetone)palladium(0), whereby a white powder of 2-{3'-(pyridine-3-yl)-1,1'-biphenyl-4-yl}-4,6-di(phenanthrene-9-yl)-benzoxazole (Compound 1-8; 4.0 g; yield: 33%) was obtained.

[Chemical Formula 210]

(1-8)

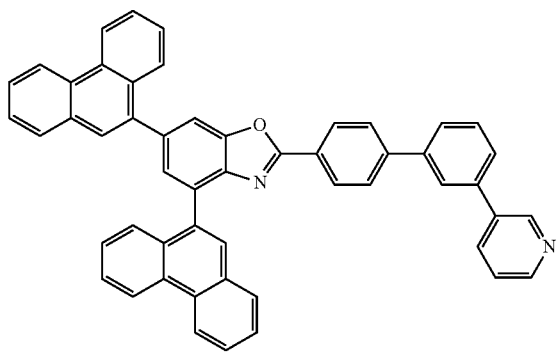

The structure of the obtained white powder was identified by NMR.

¹H-NMR (CDCl₃) detected 32 hydrogen signals, as follows.

δ(ppm)=8.93 (1H), 8.87-8.73 (4H), 8.65 (1H), 8.36 (2H), 8.18 (1H), 8.08-7.83 (8H), 7.79-7.54 (14H), 7.42 (1H).

Example 9

Synthesis of 6-(biphenyl-3-yl)-2-(biphenyl-4-yl)-4-(9-phenyl-[9H]-carbazol-3-yl)-benzoxazole (Compound 1-73)

The reaction was carried out under the same conditions as those of Example 1, except that 2-(4-chlorophenyl)-4,6-bis(4-naphthalene-1-yl-phenyl)-benzoxazole was replaced with 6-(biphenyl-3-yl)-2-(4-chlorophenyl)-4-(9-phenyl-[9H]-carbazol-3-yl)-benzoxazole, and 3-pyridylboronic acid was replaced with phenylboronic acid, whereby a white powder of 6-(biphenyl-3-yl)-2-(biphenyl-4-yl)-4-(9-phenyl-[9H]-carbazol-3-yl)-benzoxazole (Compound 1-73; 3.0 g; yield: 44%) was obtained.

[Chemical Formula 211]

(1-73)

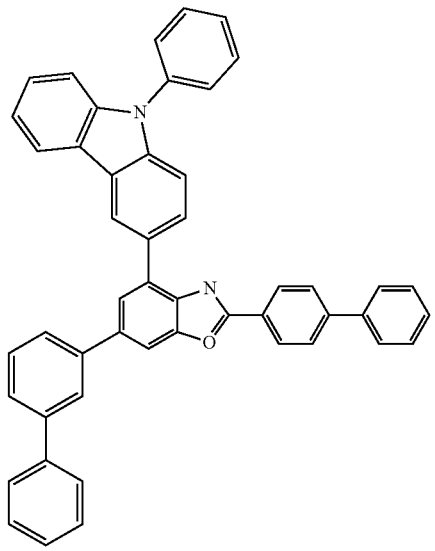

The structure of the obtained white powder was identified by NMR.

¹H-NMR (CDCl₃) detected 32 hydrogen signals, as follows.

δ(ppm)=8.90 (1H), 8.45 (2H), 8.30 (1H), 8.26 (1H), 7.94 (1H), 7.91 (1H), 7.85 (2H), 7.80 (3H), 7.74-7.32 (20H).

Example 10

Synthesis of 2-{3'-(pyridine-3-yl)-biphenyl-4-yl}-6-(9,9'-spirobi[9H]fluorene-2-yl)-benzoxazole (Compound 1-91)

The reaction was carried out under the same conditions as those of Example 1, except that 2-(4-chlorophenyl)-4,6-bis(4-naphthalene-1-yl-phenyl)-benzoxazole was replaced with 2-(4-chlorophenyl)-6-(9,9'-spirobi[9H]fluorene-2-yl)-benzoxazole, and 3-pyridylboronic acid was replaced with 3-(pyridine-3-yl)-phenylboronic acid, and bis(dibenzylideneacetone)palladium(0) was replaced with tris(dibenzylideneacetone)palladium(0), whereby a white powder of 2-{3'-

(pyridine-3-yl)-biphenyl-4-yl}-6-(9,9'-spirobi[9H]fluorene-2-yl)-benzoxazole (Compound 1-91; 10.5 g; yield: 58%) was obtained.

[Chemical Formula 212]

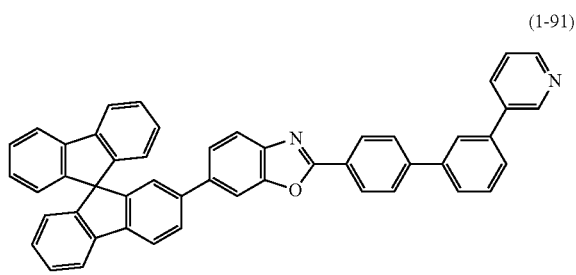

(1-91)

The structure of the obtained white powder was identified by NMR.

$^1$H-NMR (CDCl$_3$) detected 30 hydrogen signals, as follows.

δ(ppm)=8.94 (1H), 8.66 (1H), 8.33 (2H), 8.01-7.77 (8H), 7.77-7.57 (6H), 7.52-7.37 (5H), 7.15 (3H), 7.03 (1H), 6.82 (2H), 6.78 (1H).

Example 11

Synthesis of 4,6-bis(biphenyl-3-yl)-2-([1,1':3',1'']terphenyl-4-yl)-benzoxazole (Compound 1-96)

The reaction was carried out under the same conditions as those of Example 1, except that 2-(4-chlorophenyl)-4,6-bis(4-naphthalene-1-yl-phenyl)-benzoxazole was replaced with 4,6-bis(biphenyl-3-yl)-2-(4-chlorophenyl)-benzoxazole, and 3-pyridylboronic acid was replaced with 3-biphenylboronic acid, whereby a white powder of 4,6-bis(biphenyl-3-yl)-2-([1,1':3',1'']terphenyl-4-yl)-benzoxazole (Compound 1-96; 8.3 g; yield: 68.0%) was obtained.

[Chemical Formula 213]

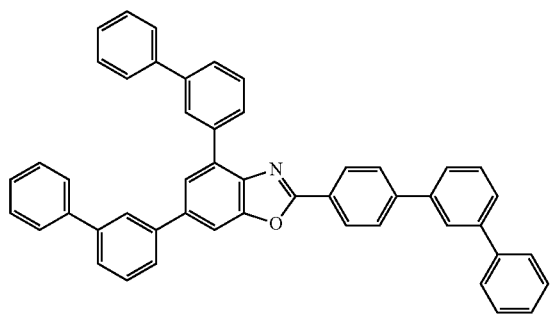

(1-96)

The structure of the obtained white powder was identified by NMR.

$^1$H-NMR (CDCl$_3$) detected 33 hydrogen signals, as follows.

δ(ppm)=8.44 (2H), 8.35 (1H), 8.14 (1H), 8.00-7.82 (6H), 7.80-7.47 (20H), 7.46-7.37 (3H).

Example 12

Synthesis of 4,6-di(dibenzofuran-4-yl)-2-(4-pyridine-3-yl-phenyl)-benzoxazole (Compound 1-100)

The reaction was carried out under the same conditions as those of Example 1, except that 2-(4-chlorophenyl)-4,6-bis(4-naphthalene-1-yl-phenyl)-benzoxazole was replaced with 2-(4-chlorophenyl)-4,6-di(dibenzofuran-4-yl)-benzoxazole, and bis(dibenzylideneacetone)palladium(0) was replaced with tris(dibenzylideneacetone)palladium(0), whereby a yellow powder of 4,6-di(dibenzofuran-4-yl)-2-(4-pyridine-3-yl-phenyl)-benzoxazole (Compound 1-100; 7.3 g; yield: 61%) was obtained.

[Chemical Formula 214]

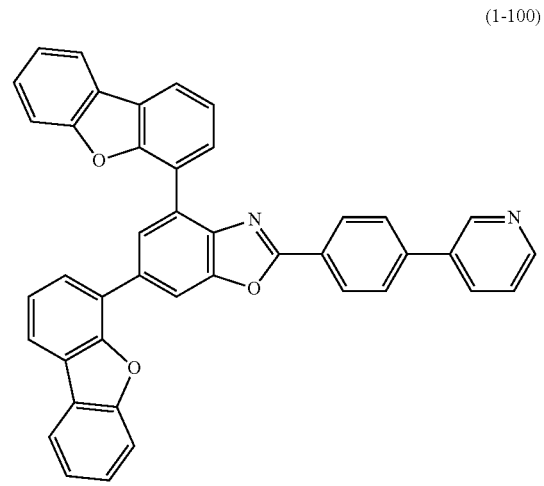

(1-100)

The structure of the obtained yellow powder was identified by NMR.

$^1$H-NMR (CDCl$_3$) detected 24 hydrogen signals, as follows.

δ(ppm)=8.96 (1H), 8.67 (1H), 8.59 (1H), 8.47 (2H), 8.37 (1H), 8.32 (1H), 8.06 (4H), 7.99 (1H), 7.84 (1H), 7.78 (2H), 7.69 (1H), 7.62 (1H), 7.61 (1H), 7.58-7.36 (6H).

Example 13

Synthesis of 2,6-diphenyl-4-(9,9'-spirobi[9H]fluorene-2-yl)-benzoxazole (Compound 1-106)

The reaction was carried out under the same conditions as those of Example 1, except that 2-(4-chlorophenyl)-4,6-bis(4-naphthalene-1-yl-phenyl)-benzoxazole was replaced with 6-chloro-2-phenyl-4-(9,9'-spirobi[9H]fluorene-2-yl)-benzoxazole, and 3-pyridylboronic acid was replaced with phenylboronic acid, whereby a white powder of 2,6-diphenyl-4-(9,9'-spirobi[9H]fluorene-2-yl)-benzoxazole (Compound 1-106; 4.5 g; yield: 41%) was obtained.

[Chemical Formula 215]

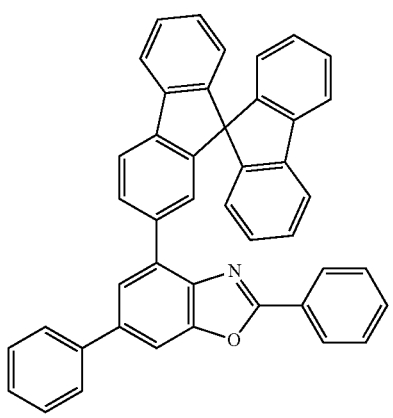

(1-106)

The structure of the obtained white powder was identified by NMR.

¹H-NMR (CDCl₃) detected 27 hydrogen signals, as follows.

δ(ppm)=8.15-7.98 (6H), 7.97-7.85 (4H), 7.60-7.36 (9H), 7.17 (4H), 6.90-6.80 (4H).

Example 14

Synthesis of 2-{3,5-di([9H]-carbazol-9-yl)-phenyl}-4,6-diphenyl-benzoxazole (Compound 1-107)

The reaction was carried out under the same conditions as those of Example 1, except that 2-(4-chlorophenyl)-4,6-bis(4-naphthalene-1-yl-phenyl)-benzoxazole was replaced with 2-(3,5-dichlorophenyl)-4,6-diphenyl-benzoxazole, and 3-pyridylboronic acid was replaced with carbazol, whereby a white powder of 2-{3,5-di([9H]-carbazol-9-yl)-phenyl}-4,6-diphenyl-benzoxazole (Compound 1-107; 4.8 g; yield: 30%) was obtained.

[Chemical Formula 216]

(1-107)

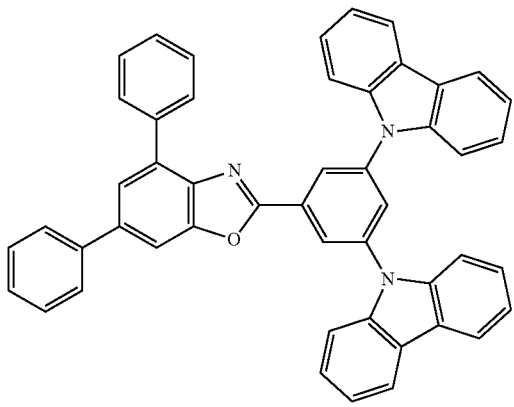

The structure of the obtained white powder was identified by NMR.

¹H-NMR (CDCl₃) detected 31 hydrogen signals, as follows.

δ(ppm)=8.67 (2H), 8.21 (4H), 8.10 (2H), 8.01 (1H), 7.85 (1H), 7.79 (1H), 7.73 (2H), 7.63 (4H), 7.57-7.46 (8H), 7.46-7.33 (6H).

Example 15

Synthesis of 4-(4-naphthalene-1-yl-phenyl)-6-{9-phenyl-[9H]-carbazol-3-yl)-2-(3-pyridine-3-yl-phenyl)-benzoxazole (Compound 1-108)

The reaction was carried out under the same conditions as those of Example 1, except that 2-(4-chlorophenyl)-4,6-bis(4-naphthalene-1-yl-phenyl)-benzoxazole was replaced with 2-(3-chlorophenyl)-4-(4-naphthalene-1-yl-phenyl)-6-(9-phenyl-[9H]-carbazol-3-yl)-benzoxazole, whereby a white powder of 4-(4-naphthalene-1-yl-phenyl)-6-(9-phenyl-[9H]-carbazol-3-yl)-2-(3-pyridine-3-yl-phenyl)-benzoxazole (Compound 1-108; 2.6 g; yield: 47%) was obtained.

[Chemical Formula 217]

(1-108)

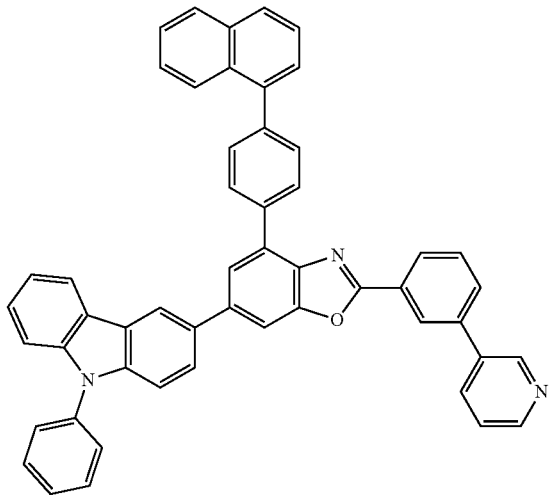

The structure of the obtained white powder was identified by NMR.

¹H-NMR (CDCl₃) detected 33 hydrogen signals, as follows.

δ(ppm)=9.01 (1H), 8.69 (1H), 8.61 (1H), 8.53 (1H), 8.44 (1H), 8.35 (2H), 8.28 (1H), 8.14 (1H), 8.06 (1H), 8.05 (1H), 7.97 (1H), 7.96 (1H), 7.93 (1H), 7.86-7.42 (18H), 7.37 (1H).

Example 16

Synthesis of 2-phenyl-6-(9-phenyl-[9H]-carbazol-3-yl)-4-(5-phenyl-[5H]-pyrido[4,3-b]indole-8-yl)-benzoxazole (Compound 1-110)

The reaction was carried out under the same conditions as those of Example 1, except that 2-(4-chlorophenyl)-4,6-bis(4-naphthalene-1-yl-phenyl)-benzoxazole was replaced with 6-chloro-2-phenyl-4-(5-phenyl-[5H]-pyrido[4,3-b]indole-8-yl)-benzoxazole, and 3-pyridylboronic acid was replaced with 9-phenyl-[9H]-carbazol-3-yl-boronic acid, whereby a yellow powder of 2-phenyl-6-(9-phenyl-[9H]-carbazol-3-yl)-4-(5-phenyl-[5H]-pyrido[4,3-b]indole-8-yl)-benzoxazole (Compound 1-110; 2.9 g; yield: 50%) was obtained.

[Chemical Formula 218]

(1-110)

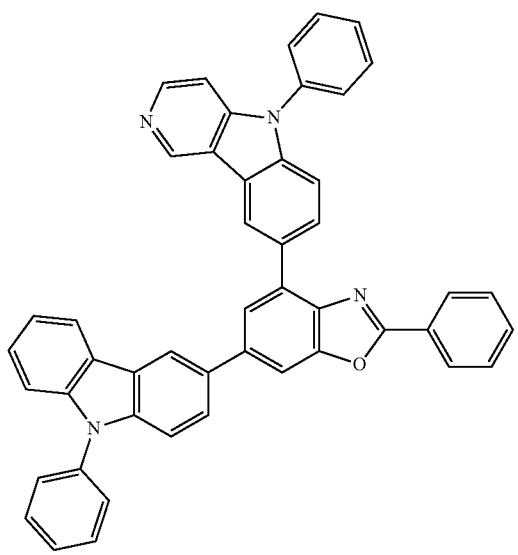

The structure of the obtained yellow powder was identified by NMR.

$^1$H-NMR (CDCl$_3$) detected 30 hydrogen signals, as follows.

δ(ppm)=9.56 (1H), 9.04 (1H), 8.59 (1H), 8.53 (1H), 8.48 (1H), 8.45 (1H), 8.36 (1H), 8.26 (2H), 8.05 (1H), 7.93 (2H), 7.88-7.43 (16H), 7.36 (2H).

Example 17

Synthesis of 6-(4-naphthalene-1-yl-phenyl)-2-(biphenyl-4-yl)-4-(4-pyridine-3-yl-phenyl)-benzoxazole (Compound 1-112)

The reaction was carried out under the same conditions as those of Example 1, except that 2-(4-chlorophenyl)-4,6-bis(4-naphthalene-1-yl-phenyl)-benzoxazole was replaced with 2-(4-chlorophenyl)-6-(4-naphthalene-1-yl-phenyl)-4-(4-pyridine-3-yl-phenyl)-benzoxazole, and 3-pyridylboronic acid was replaced with phenylboronic acid, and bis(dibenzylideneacetone)palladium(0) was replaced with tris(dibenzylideneacetone)palladium(0), whereby a white powder of 6-(4-naphthalene-1-yl-phenyl)-2-(biphenyl-4-yl)-4-(4-pyridine-3-yl-phenyl)-benzoxazole (Compound 1-112; 4.8 g; yield: 56%) was obtained.

[Chemical Formula 219]

(1-112)

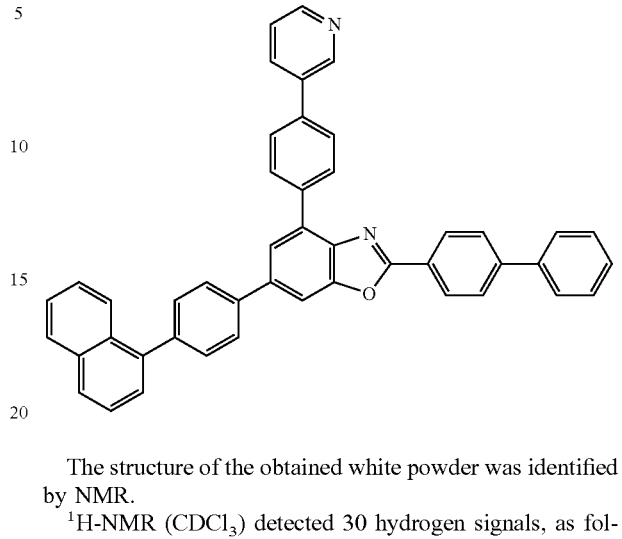

The structure of the obtained white powder was identified by NMR.

$^1$H-NMR (CDCl$_3$) detected 30 hydrogen signals, as follows.

δ(ppm)=9.00 (1H), 8.66 (1H), 8.45 (2H), 8.33 (2H), 8.07-7.78 (12H), 7.70 (4H), 7.63-7.40 (8H).

Example 18

Synthesis of 2,6-bis(4-naphthalene-1-yl-phenyl)-4-(4-pyridine-3-yl-phenyl)-benzoxazole (Compound 1-113)

The reaction was carried out under the same conditions as those of Example 1, except that 2-(4-chlorophenyl)-4,6-bis(4-naphthalene-1-yl-phenyl)-benzoxazole was replaced with 2-(4-chlorophenyl)-6-(4-naphthalene-1-yl-phenyl)-4-(4-pyridine-3-yl-phenyl)-benzoxazole, and 3-pyridylboronic acid was replaced with 1-naphthaleneboronic acid, and bis(dibenzylideneacetone)palladium(0) was replaced with tris(dibenzylideneacetone)palladium(0), whereby a white powder of 2,6-bis(4-naphthalene-1-yl-phenyl)-4-(4-pyridine-3-yl-phenyl)-benzoxazole (Compound 1-113; 6.1 g; yield: 66%) was obtained.

[Chemical Formula 220]

(1-113)

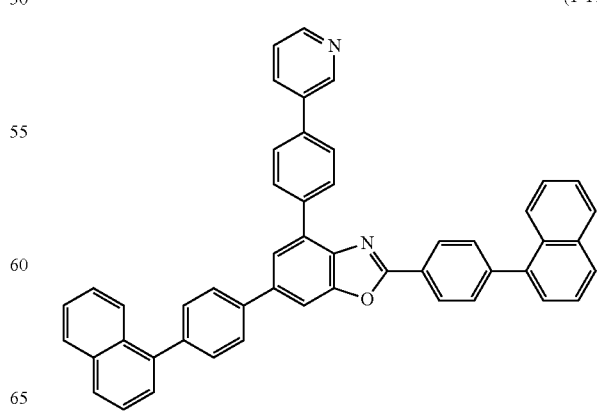

The structure of the obtained white powder was identified by NMR.

¹H-NMR (CDCl₃) detected 32 hydrogen signals, as follows.

δ(ppm)=9.01 (1H), 8.66 (1H), 8.51 (2H), 8.35 (2H), 8.09-7.80 (13H), 7.73 (2H), 7.69 (2H), 7.64-7.40 (9H).

Example 19

Synthesis of 2-(biphenyl-4-yl)-6-(phenanthrene-9-yl)-4-(4-pyridine-3-yl-phenyl)-benzoxazole (Compound 1-118)

The reaction was carried out under the same conditions as those of Example 1, except that 2-(4-chlorophenyl)-4,6-bis(4-naphthalene-1-yl-phenyl)-benzoxazole was replaced with 2-(4-chlorophenyl)-6-(phenanthrene-9-yl)-4-(4-pyridine-3-yl-phenyl)-benzoxazole, and 3-pyridylboronic acid was replaced with phenylboronic acid, and bis(dibenzylideneacetone)palladium(0) was replaced with tris(dibenzylideneacetone)palladium(0), whereby a white powder of 2-(biphenyl-4-yl)-6-(phenanthrene-9-yl)-4-(4-pyridine-3-yl-phenyl)-benzoxazole (Compound 1-118; 4.3 g; yield: 67%) was obtained.

[Chemical Formula 221]

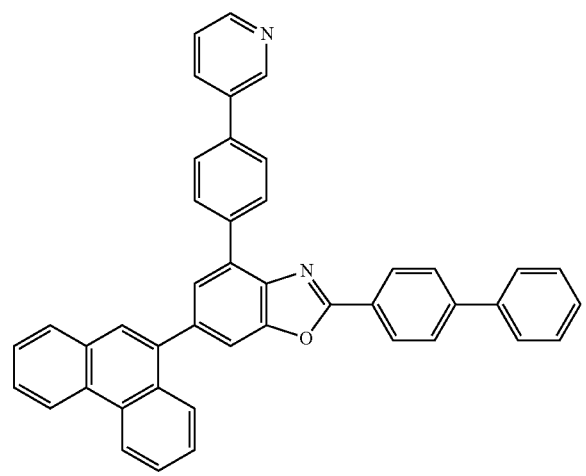

(1-118)

The structure of the obtained white powder was identified by NMR.

¹H-NMR (CDCl₃) detected 28 hydrogen signals, as follows.

δ(ppm)=8.98 (1H), 8.86 (1H), 8.80 (1H), 8.64 (1H), 8.46 (2H), 8.32 (2H), 8.07 (1H), 7.98 (2H), 7.88-7.57 (13H), 7.52 (2H), 7.44 (2H).

Example 20

Synthesis of 2-(biphenyl-4-yl)-6-(phenanthrene-9-yl)-4-(3-pyridine-3-yl-phenyl)-benzoxazole (Compound 1-119)

The reaction was carried out under the same conditions as those of Example 1, except that 2-(4-chlorophenyl)-4,6-bis(4-naphthalene-1-yl-phenyl)-benzoxazole was replaced with 2-(4-chlorophenyl)-6-(phenanthrene-9-yl)-4-(3-pyridine-3-yl-phenyl)-benzoxazole, and 3-pyridylboronic acid was replaced with phenylboronic acid, and bis(dibenzylideneacetone)palladium(0) was replaced with tris(dibenzylideneacetone)palladium(0), whereby a white powder of 2-(biphenyl-4-yl)-6-(phenanthrene-9-yl)-4-(3-pyridine-3-yl-phenyl)-benzoxazole (Compound 1-119; 3.0 g; yield: 35%) was obtained.

[Chemical Formula 222]

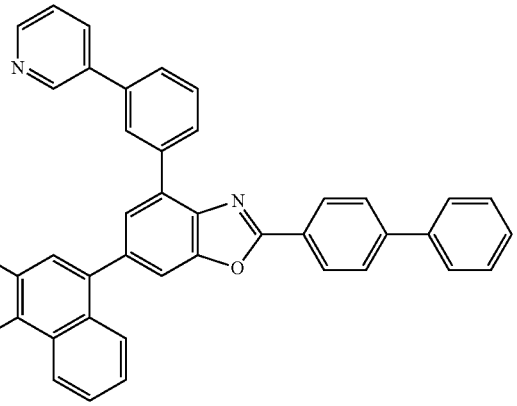

(1-119)

The structure of the obtained white powder was identified by NMR.

¹H-NMR (CDCl₃) detected 28 hydrogen signals, as follows.

δ(ppm)=9.02 (1H), 8.85 (1H), 8.79 (1H), 8.64 (1H), 8.45 (2H), 8.43 (1H), 8.19 (1H), 8.07 (1H), 8.02 (1H), 7.97 (1H), 7.89-7.78 (5H), 7.78-7.39 (12H).

Example 21

Synthesis of 6-(phenanthrene-9-yl)-4-(4-pyridine-3-yl-phenyl)-2-([1,1':4',1"]terphenyl-4-yl)-benzoxazole (Compound 1-120)

The reaction was carried out under the same conditions as those of Example 1, except that 2-(4-chlorophenyl)-4,6-bis(4-naphthalene-1-yl-phenyl)-benzoxazole was replaced with 2-(4-chlorophenyl)-6-(phenanthrene-9-yl)-4-(4-pyridine-3-yl-phenyl)-benzoxazole, and 3-pyridylboronic acid was replaced with 4-biphenylboronic acid, and bis(dibenzylideneacetone)palladium(0) was replaced with tris(dibenzylideneacetone)palladium(0), whereby a white powder of 6-(phenanthrene-9-yl)-4-(4-pyridine-3-yl-phenyl)-2-([1,1':4',1"]terphenyl-4-yl)-benzoxazole (Compound 1-120; 2.8 g; yield: 36%) was obtained.

[Chemical Formula 223]

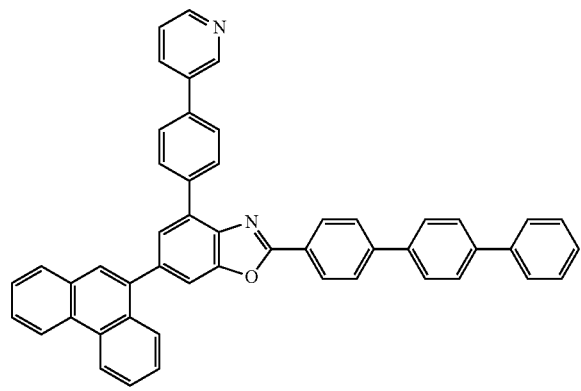

(1-120)

The structure of the obtained white powder was identified by NMR.

¹H-NMR (CDCl₃) detected 32 hydrogen signals, as follows.

δ(ppm)=8.98 (1H), 8.86 (1H), 8.80 (1H), 8.64 (1H), 8.48 (2H), 8.33 (2H), 8.08 (1H), 7.98 (2H), 7.90-7.57 (17H), 7.51 (2H), 7.41 (2H).

Example 22

Synthesis of 2-(4-naphthalene-2-yl-phenyl)-6-(phenanthrene-9-yl)-4-(4-pyridine-3-yl-phenyl)-benzoxazole (Compound 1-122)

The reaction was carried out under the same conditions as those of Example 1, except that 2-(4-chlorophenyl)-4,6-bis(4-naphthalene-1-yl-phenyl)-benzoxazole was replaced with 2-(4-chlorophenyl)-6-(phenanthrene-9-yl)-4-(4-pyridine-3-yl-phenyl)-benzoxazole, and 3-pyridylboronic acid was replaced with 2-naphthaleneboronic acid, and bis(dibenzylideneacetone)palladium(0) was replaced with tris(dibenzylideneacetone)palladium(0), whereby a white powder of 2-(4-naphthalene-2-yl-phenyl)-6-(phenanthrene-9-yl)-4-(4-pyridine-3-yl-phenyl)-benzoxazole (Compound 1-122; 3.0 g; yield: 43%) was obtained.

[Chemical Formula 224]

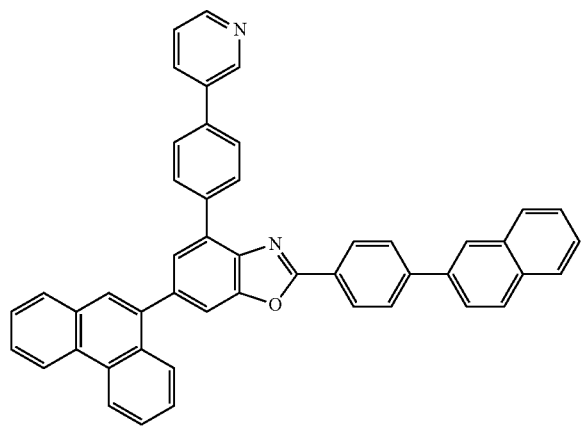

(1-122)

The structure of the obtained white powder was identified by NMR.

¹H-NMR (CDCl₃) detected 30 hydrogen signals, as follows.

δ(ppm)=8.98 (1H), 8.86 (1H), 8.80 (1H), 8.65 (1H), 8.51 (2H), 8.33 (2H), 8.17 (1H), 8.08 (1H), 8.03-7.90 (7H), 7.89-7.51 (12H), 7.42 (1H).

Example 23

Synthesis of 2-phenyl-4-(4-pyridine-3-yl-phenyl)-6-(triphenylene-2-yl)-benzoxazole (Compound 1-125)

The reaction was carried out under the same conditions as those of Example 1, except that 2-(4-chlorophenyl)-4,6-bis(4-naphthalene-1-yl-phenyl)-benzoxazole was replaced with 6-chloro-2-phenyl-4-(4-pyridine-3-yl-phenyl)-benzoxazole, and 3-pyridylboronic acid was replaced with 2-triphenyleneboronic acid, and bis(dibenzylideneacetone)palladium(0) was replaced with tris(dibenzylideneacetone)palladium(0), whereby a white powder of 2-phenyl-4-(4-pyridine-3-yl-phenyl)-6-(triphenylene-2-yl)-benzoxazole (Compound 1-125; 5.9 g; yield: 28%) was obtained.

[Chemical Formula 225]

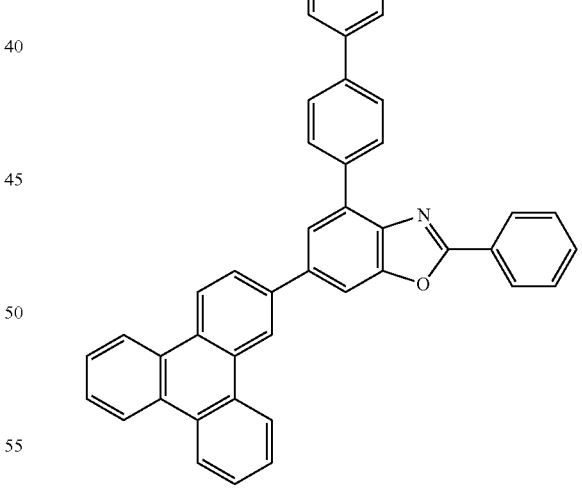

(1-125)

The structure of the obtained white powder was identified by NMR.

¹H-NMR (CDCl₃) detected 26 hydrogen signals, as follows.

δ(ppm)=8.99 (2H), 8.85-8.63 (6H), 8.35 (2H), 8.33 (2H), 8.08-7.97 (4H), 7.83 (2H), 7.72 (4H), 7.59 (3H), 7.44 (1H).

Example 24

Synthesis of 6-(phenanthrene-9-yl)-2-{3'-(pyridine-3-yl)-biphenyl-4-yl}-4-(4-pyridine-3-yl-phenyl)-benzoxazole (Compound 1-131)

The reaction was carried out under the same conditions as those of Example 1, except that 2-(4-chlorophenyl)-4,6-bis(4-naphthalene-1-yl-phenyl)-benzoxazole was replaced with 2-(4-chlorophenyl)-6-(phenanthrene-9-yl)-4-(4-pyridine-3-yl-phenyl)-benzoxazole, and 3-pyridylboronic acid was replaced with 3-(pyridine-3-yl)phenylboronic acid, and bis(dibenzylideneacetone)palladium(0) was replaced with tris(dibenzylideneacetone)palladium(0), whereby a yellow powder of 6-(phenanthrene-9-yl)-2-{3'-(pyridine-3-yl)-biphenyl-4-yl}-4-(4-pyridine-3-yl-phenyl)-benzoxazole (Compound 1-131; 3.4 g; yield: 43%) was obtained.

[Chemical Formula 226]

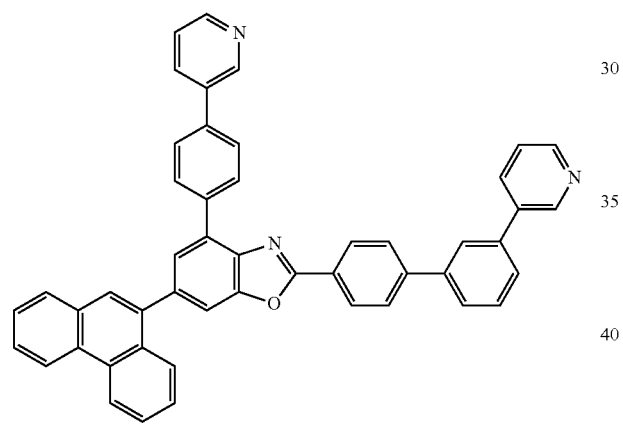

(1-131)

The structure of the obtained yellow powder was identified by NMR.

$^1$H-NMR (CDCl$_3$) detected 31 hydrogen signals, as follows.

δ(ppm)=9.04 (1H), 8.67 (1H), 8.47 (2H), 8.15 (4H), 8.08-7.72 (15H), 7.72-7.42 (8H).

Example 25

Synthesis of 4,6-bis(4-naphthalene-1-yl-phenyl)-2-(4-pyridine-3-yl-phenyl)-benzothiazole (Compound 2-1)

The reaction was carried out under the same conditions as those of Example 1, except that 2-(4-chlorophenyl)-4,6-bis(4-naphthalene-1-yl-phenyl)-benzoxazole was replaced with 2-(4-chlorophenyl)-4,6-bis(4-naphthalene-1-yl-phenyl)-benzothiazole, whereby a yellow powder of 4,6-bis(4-naphthalene-1-yl-phenyl)-2-(4-pyridine-3-yl-phenyl)-benzothiazole (Compound 2-1; 3.5 g; yield: 21%) was obtained.

[Chemical Formula 227]

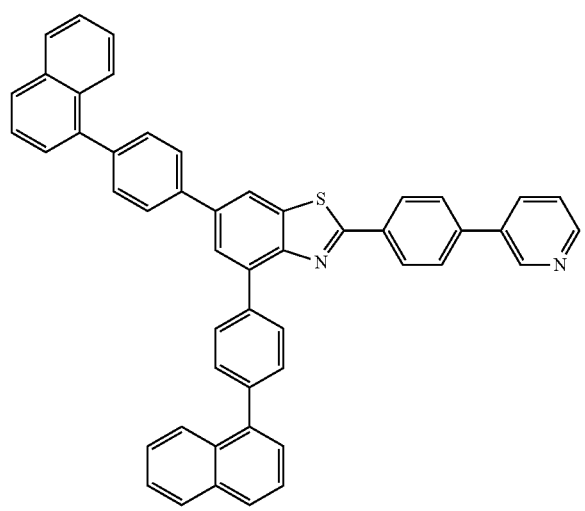

(2-1)

The structure of the obtained yellow powder was identified by NMR.

$^1$H-NMR (CDCl$_3$) detected 32 hydrogen signals, as follows.

δ(ppm)=8.98 (1H), 8.68 (1H), 8.52 (2H), 8.40-8.25 (3H), 8.12 (1H), 8.07-7.69 (15H), 7.64 (9H).

Example 26

Synthesis of 2-(biphenyl-4-yl)-6-(phenanthrene-9-yl)-4-(4-pyridine-3-yl-phenyl)-benzothiazole (Compound 2-63)

The reaction was carried out under the same conditions as those of Example 1, except that 2-(4-chlorophenyl)-4,6-bis(4-naphthalene-1-yl-phenyl)-benzoxazole was replaced with 2-(4-chlorophenyl)-6-(phenanthrene-9-yl)-4-(4-pyridine-3-yl-phenyl)-benzothiazole, and 3-pyridylboronic acid was replaced with phenylboronic acid, and bis(dibenzylideneacetone)palladium(0) was replaced with tris(dibenzylideneacetone)palladium(0), whereby a yellow powder of 2-(biphenyl-4-yl)-6-(phenanthrene-9-yl)-4-(4-pyridine-3-yl-phenyl)-benzothiazole (Compound 2-63; 2.0 g; yield: 24%) was obtained.

[Chemical Formula 228]

(2-63)

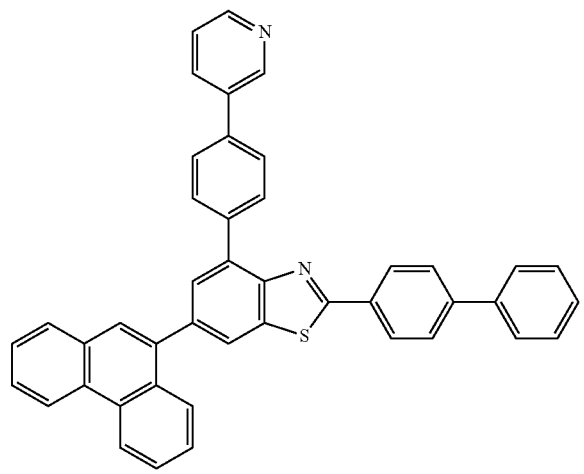

The structure of the obtained yellow powder was identified by NMR.

$^1$H-NMR (CDCl$_3$) detected 28 hydrogen signals, as follows.

δ(ppm)=8.98 (1H), 8.86 (1H), 8.80 (1H), 8.64 (1H), 8.46 (2H), 8.32 (2H), 8.12-7.93 (4H), 7.88-7.57 (12H), 7.52 (2H), 7.44 (2H).

Example 27

The melting points and the glass transition points of the compounds having a fused-azole ring structure of the general formula (1) were measured using a high-sensitive differential scanning calorimeter (DSC3100SA produced by Bruker AXS).

|  | Melting point | Glass transition point |
| --- | --- | --- |
| Compound of Example 1 | No melting point observed | 123° C. |
| Compound of Example 2 | 277° C. | 119° C. |
| Compound of Example 3 | No melting point observed | 117° C. |
| Compound of Example 4 | 254° C. | 109° C. |
| Compound of Example 5 | No melting point observed | 124° C. |
| Compound of Example 6 | 279° C. | 164° C. |
| Compound of Example 7 | No melting point observed | 117° C. |
| Compound of Example 8 | No melting point observed | 148° C. |
| Compound of Example 9 | 236° C. | 113° C. |
| Compound of Example 10 | 235° C. | 137° C. |
| Compound of Example 11 | No melting point observed | 82° C. |
| Compound of Example 12 | 291° C. | 123° C. |
| Compound of Example 13 | 242° C. | 121° C. |
| Compound of Example 14 | 273° C. | 144° C. |
| Compound of Example 15 | 254° C. | 131° C. |
| Compound of Example 16 | No melting point observed | 180° C. |
| Compound of Example 17 | 228° C. | 116° C. |
| Compound of Example 18 | No melting point observed | 124° C. |
| Compound of Example 19 | No melting point observed | 132° C. |
| Compound of Example 20 | No melting point observed | 116° C. |
| Compound of Example 21 | 263° C. | 144° C. |
| Compound of Example 22 | 271° C. | 136° C. |
| Compound of Example 23 | 282° C. | 126° C. |
| Compound of Example 24 | No melting point observed | 133° C. |
| Compound of Example 25 | No melting point observed | 118° C. |
| Compound of Example 26 | No melting point observed | 125° C. |

The compounds having a fused-azole ring structure of the general formula (1) have glass transition points of 100° C. or higher, demonstrating that the compounds have a stable thin-film state.

Example 28

A 100 nm-thick vapor-deposited film was fabricated on an ITO substrate using the compounds having a fused-azole ring structure of the general formula (1), and a work function was measured using an ionization potential measuring device (PYS-202 produced by Sumitomo Heavy Industries, Ltd.).

|  | Work function |
| --- | --- |
| Compound of Example 1 | 6.34 eV |
| Compound of Example 2 | 6.40 eV |
| Compound of Example 3 | 6.40 eV |
| Compound of Example 4 | 6.43 eV |
| Compound of Example 5 | 6.41 eV |
| Compound of Example 6 | 6.38 eV |
| Compound of Example 7 | 6.37 eV |
| Compound of Example 8 | 6.40 eV |
| Compound of Example 9 | 5.98 eV |
| Compound of Example 10 | 6.33 eV |
| Compound of Example 11 | 6.34 eV |
| Compound of Example 12 | 6.27 eV |
| Compound of Example 13 | 6.46 eV |
| Compound of Example 14 | 6.28 eV |
| Compound of Example 15 | 6.05 eV |
| Compound of Example 16 | 5.94 eV |
| Compound of Example 17 | 6.30 eV |
| Compound of Example 18 | 6.31 eV |
| Compound of Example 19 | 6.43 eV |
| Compound of Example 20 | 6.33 eV |
| Compound of Example 21 | 6.36 eV |
| Compound of Example 22 | 6.43 eV |
| Compound of Example 23 | 6.22 eV |
| Compound of Example 24 | 6.41 eV |
| Compound of Example 25 | 6.41 eV |
| Compound of Example 26 | 6.50 eV |

As the results show, the compounds having a fused-azole ring structure of the general formula (1) have a value larger than the work function 5.5 eV of common hole transport materials such as NPD and TPD, and thus possess large hole blocking ability.

Example 29

The organic EL device, as shown in the FIGURE, was fabricated by vapor-depositing a hole injection layer 3, a hole transport layer 4, a light emitting layer 5, a hole blocking layer 6, an electron transport layer 7, an electron injection layer 8, and a cathode (aluminum electrode) 9 in this order on a glass substrate 1 on which an ITO electrode was formed as a transparent anode 2 beforehand.

Specifically, the glass substrate 1 on which ITO with a film thickness of 50 nm was formed was ultrasonically cleaned in isopropyl alcohol for 20 minutes, and then dried on a hot plate heated at 200° C. for 10 minutes. Thereafter, after performing a UV ozone treatment for 15 minutes, the glass substrate 1 with ITO was installed in a vacuum vapor deposition apparatus, and the pressure was reduced to 0.001 Pa or lower. Subsequently, as the hole injection layer 3 covering the transparent anode 2, Compound HIM-1 of the structural formula below was formed in a film thickness of 5 nm. As the hole transport layer 4 on the hole injection layer 3, Compound HTM-1 of the structural formula below was formed in a film thickness of 65 nm. As the light emitting layer 5 on the hole transport layer 4, Compound EMD-1 of the structural formula below and Compound EMH-1 of the structural formula below were formed in a film thickness of 20 nm by dual vapor deposition at a vapor deposition rate that satisfies a vapor deposition rate ratio of EMD-1/EMH-1=5/95. As the hole blocking layer 6 also serving as an electron transport layer 7 on the light emitting layer 5, the compound (Compound 1-1) of Example 1 of the invention and Compound ETM-1 of the structural formula below were formed in a film thickness of 30 nm by dual vapor deposition at a vapor deposition rate that satisfies a vapor deposition rate ratio of Compound 1-1/ETM-1=50/50. As the electron injection layer 8 on the hole blocking layer 6/the electron transport layer 7, lithium fluoride was formed in a film thickness of 1 nm. Finally, aluminum was vapor-deposited in a thickness of 100 nm to form the cathode 9. The characteristics of the organic EL device were measured in the atmosphere at ordinary temperature. Table 1 summarizes the results of measurement of emission characteristics when applying a DC voltage to the fabricated organic EL device.

[Chemical Formula 229]

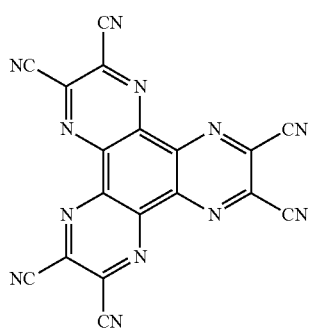

(HIM-1)

[Chemical Formula 230]

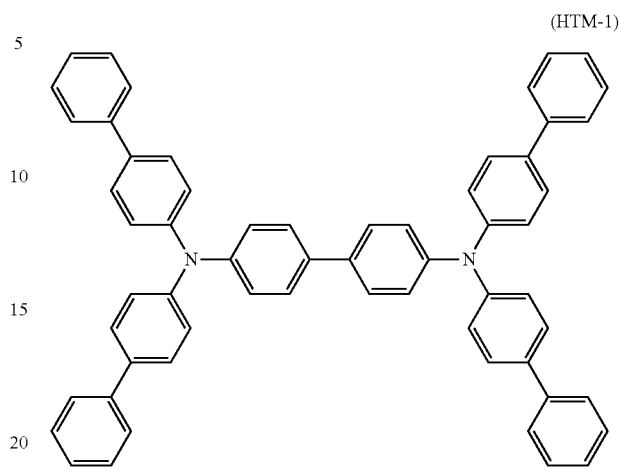

(HTM-1)

[Chemical Formula 231]

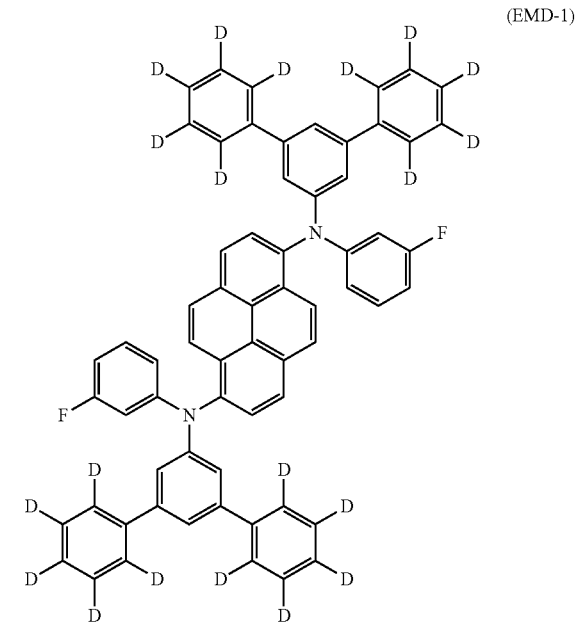

(EMD-1)

[Chemical Formula 232]

(EMH-1)

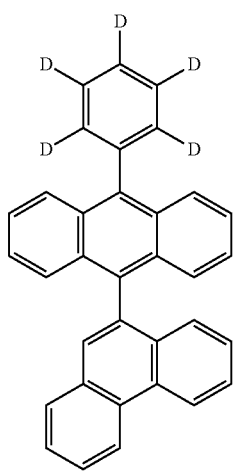

[Chemical Formula 233]

(1-1)

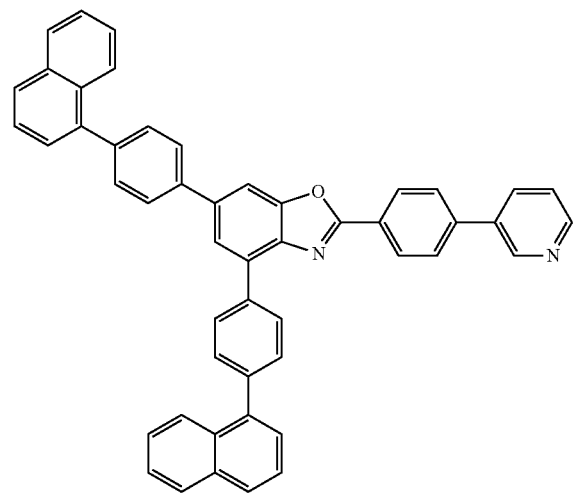

[Chemical Formula 234]

(ETM-1)

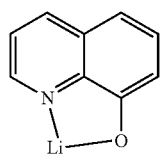

Example 30

An organic EL device was fabricated under the same conditions used in Example 29, except that the compound (Compound 1-1) of Example 1 was replaced with the compound (Compound 1-2) of Example 2 as the material of the hole blocking layer 6/the electron transport layer 7, and the layer was formed by dual vapor deposition of the compound (Compound 1-2) of Example 2 and the compound ETM-1 at a vapor deposition rate ratio of Compound 1-2/ETM-1=50/50. The characteristics of the organic EL device thus fabricated were measured in the atmosphere at an ordinary temperature. Table 1 summarizes the results of measurement of emission characteristics when applying a DC voltage to the fabricated organic EL device.

[Chemical Formula 235]

(1-2)

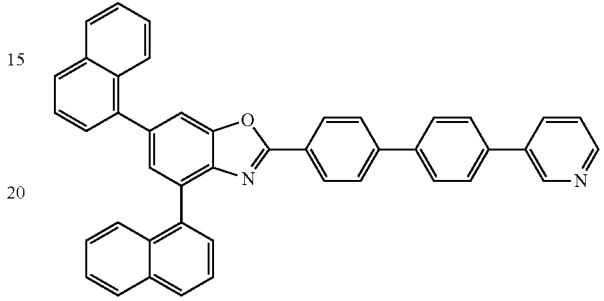

Example 31

An organic EL device was fabricated under the same conditions used in Example 29, except that the compound (Compound 1-1) of Example 1 was replaced with the compound (Compound 1-6) of Example 6 as the material of the hole blocking layer 6/the electron transport layer 7, and the layer was formed by dual vapor deposition of the compound (Compound 1-6) of Example 6 and the compound ETM-1 at a vapor deposition rate ratio of Compound 1-6/ETM-1=50/50. The characteristics of the organic EL device thus fabricated were measured in the atmosphere at an ordinary temperature. Table 1 summarizes the results of measurement of emission characteristics when applying a DC voltage to the fabricated organic EL device.

[Chemical Formula 236]

(1-6)

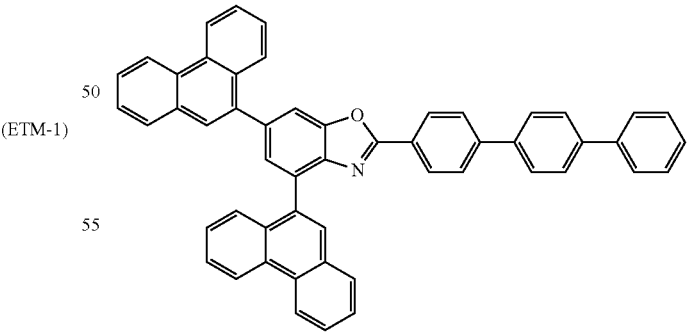

Example 32

An organic EL device was fabricated under the same conditions used in Example 29, except that the compound (Compound 1-1) of Example 1 was replaced with the compound (Compound 1-8) of Example 8 as the material of the hole blocking layer 6/the electron transport layer 7, and the layer was formed by dual vapor deposition of the compound (Compound 1-8) of Example 8 and the compound ETM-1 at a vapor deposition rate ratio of Compound 1-8/ETM-1=50/50. The characteristics of the organic EL device thus fabricated were measured in the atmosphere at an ordinary temperature. Table 1 summarizes the results of measurement of emission characteristics when applying a DC voltage to the fabricated organic EL device.

[Chemical Formula 237]

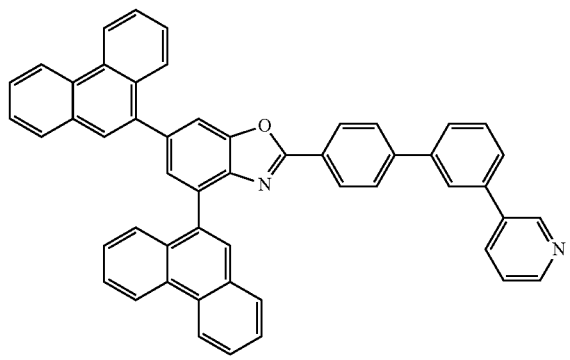

(1-8)

Example 33

An organic EL device was fabricated under the same conditions used in Example 29, except that the compound (Compound 1-1) of Example 1 was replaced with the compound (Compound 1-112) of Example 17 as the material of the hole blocking layer 6/the electron transport layer 7, and the layer was formed by dual vapor deposition of the compound (Compound 1-112) of Example 17 and the compound ETM-1 at a vapor deposition rate ratio of Compound 1-112/ETM-1=50/50. The characteristics of the organic EL device thus fabricated were measured in the atmosphere at an ordinary temperature. Table 1 summarizes the results of measurement of emission characteristics when applying a DC voltage to the fabricated organic EL device.

[Chemical Formula 238]

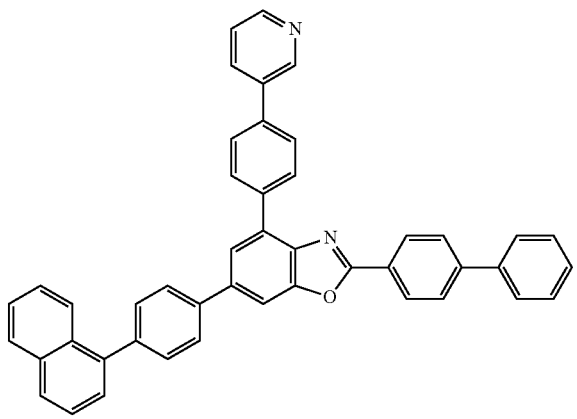

(1-112)

Example 34

An organic EL device was fabricated under the same conditions used in Example 29, except that the compound (Compound 1-1) of Example 1 was replaced with the compound (Compound 1-113) of Example 18 as the material of the hole blocking layer 6/the electron transport layer 7, and the layer was formed by dual vapor deposition of the compound (Compound 1-113) of Example 18 and the compound ETM-1 at a vapor deposition rate ratio of Compound 1-113/ETM-1=50/50. The characteristics of the organic EL device thus fabricated were measured in the atmosphere at an ordinary temperature. Table 1 summarizes the results of measurement of emission characteristics when applying a DC voltage to the fabricated organic EL device.

[Chemical Formula 239]

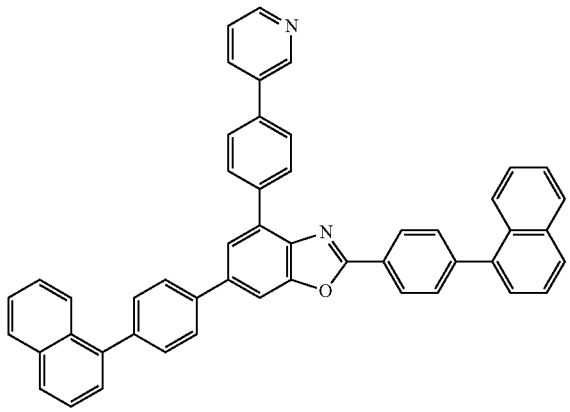

(1-113)

Example 35

An organic EL device was fabricated under the same conditions used in Example 29, except that the compound (Compound 1-1) of Example 1 was replaced with the compound (Compound 1-118) of Example 19 as the material of the hole blocking layer 6/the electron transport layer 7, and the layer was formed by dual vapor deposition of the compound (Compound 1-118) of Example 19 and the compound ETM-1 at a vapor deposition rate ratio of Compound 1-118/ETM-1=50/50. The characteristics of the organic EL device thus fabricated were measured in the atmosphere at an ordinary temperature. Table 1 summarizes the results of measurement of emission characteristics when applying a DC voltage to the fabricated organic EL device.

[Chemical Formula 240]

(1-118)

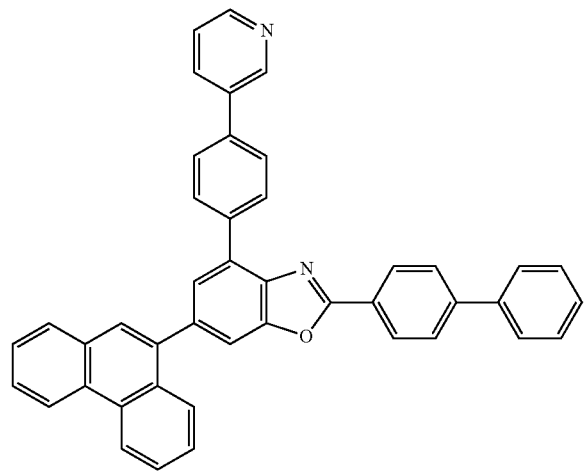

Example 36

An organic EL device was fabricated under the same conditions used in Example 29, except that the compound (Compound 1-1) of Example 1 was replaced with the compound (Compound 1-119) of Example 20 as the material of the hole blocking layer 6/the electron transport layer 7, and the layer was formed by dual vapor deposition of the compound (Compound 1-119) of Example 20 and the compound ETM-1 at a vapor deposition rate ratio of Compound 1-119/ETM-1=50/50. The characteristics of the organic EL device thus fabricated were measured in the atmosphere at an ordinary temperature. Table 1 summarizes the results of measurement of emission characteristics when applying a DC voltage to the fabricated organic EL device.

[Chemical Formula 241]

(1-119)

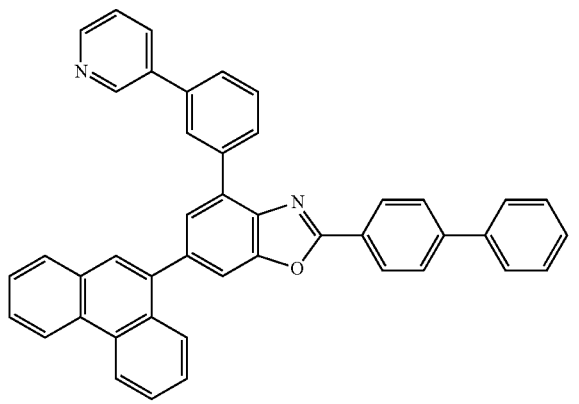

Example 37

An organic EL device was fabricated under the same conditions used in Example 29, except that the compound (Compound 1-1) of Example 1 was replaced with the compound (Compound 1-120) of Example 21 as the material of the hole blocking layer 6/the electron transport layer 7, and the layer was formed by dual vapor deposition of the compound (Compound 1-120) of Example 21 and the compound ETM-1 at a vapor deposition rate ratio of Compound 1-120/ETM-1=50/50. The characteristics of the organic EL device thus fabricated were measured in the atmosphere at an ordinary temperature. Table 1 summarizes the results of measurement of emission characteristics when applying a DC voltage to the fabricated organic EL device.

[Chemical Formula 242]

(1-120)

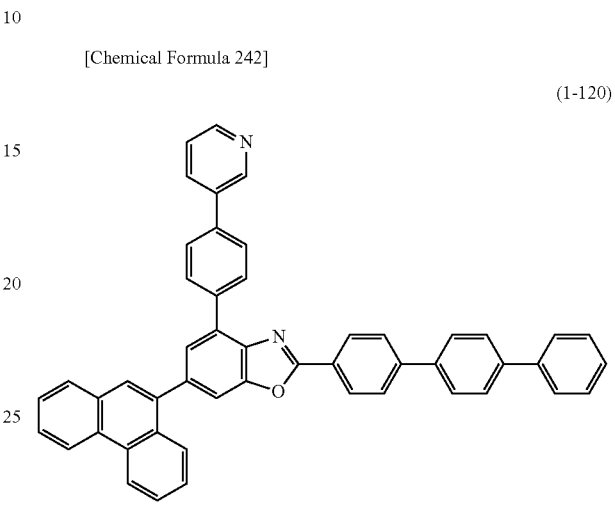

Example 38

An organic EL device was fabricated under the same conditions used in Example 29, except that the compound (Compound 1-1) of Example 1 was replaced with the compound (Compound 1-122) of Example 22 as the material of the hole blocking layer 6/the electron transport layer 7, and the layer was formed by dual vapor deposition of the compound (Compound 1-122) of Example 22 and the compound ETM-1 at a vapor deposition rate ratio of Compound 1-122/ETM-1=50/50. The characteristics of the organic EL device thus fabricated were measured in the atmosphere at an ordinary temperature. Table 1 summarizes the results of measurement of emission characteristics when applying a DC voltage to the fabricated organic EL device.

[Chemical Formula 243]

(1-122)

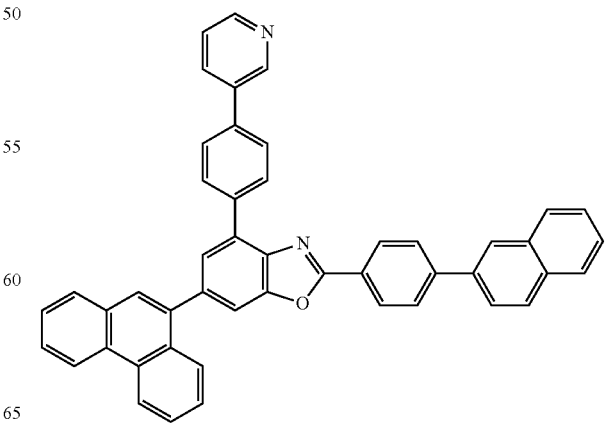

Example 39

An organic EL device was fabricated under the same conditions used in Example 29, except that the compound (Compound 1-1) of Example 1 was replaced with the compound (Compound 1-125) of Example 23 as the material of the hole blocking layer 6/the electron transport layer 7, and the layer was formed by dual vapor deposition of the compound (Compound 1-125) of Example 23 and the compound ETM-1 at a vapor deposition rate ratio of Compound 1-125/ETM-1=50/50. The characteristics of the organic EL device thus fabricated were measured in the atmosphere at an ordinary temperature. Table 1 summarizes the results of measurement of emission characteristics when applying a DC voltage to the fabricated organic EL device.

[Chemical Formula 244]

(1-125)

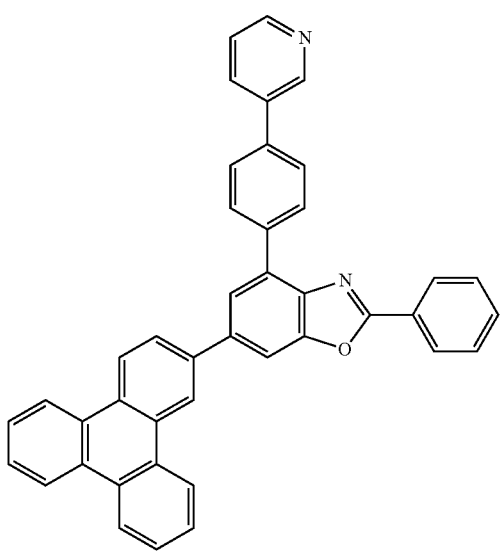

Example 40

An organic EL device was fabricated under the same conditions used in Example 29, except that the compound (Compound 1-1) of Example 1 was replaced with the compound (Compound 1-131) of Example 24 as the material of the hole blocking layer 6/the electron transport layer 7, and the layer was formed by dual vapor deposition of the compound (Compound 1-131) of Example 24 and the compound ETM-1 at a vapor deposition rate ratio of Compound 1-131/ETM-1=50/50. The characteristics of the organic EL device thus fabricated were measured in the atmosphere at an ordinary temperature. Table 1 summarizes the results of measurement of emission characteristics when applying a DC voltage to the fabricated organic EL device.

[Chemical Formula 245]

(1-131)

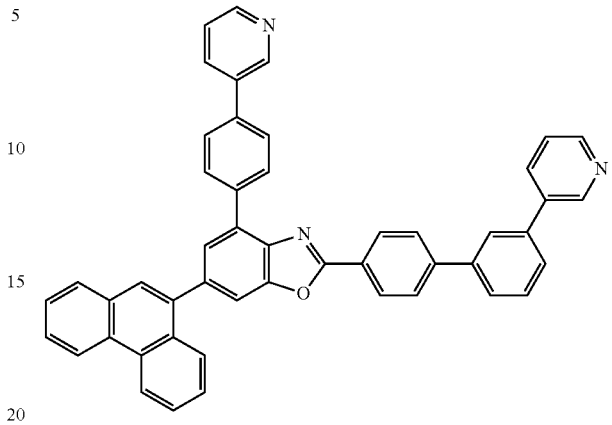

Example 41

An organic EL device was fabricated under the same conditions used in Example 29, except that the compound (Compound 1-1) of Example 1 was replaced with the compound (Compound 2-1) of Example 25 as the material of the hole blocking layer 6/the electron transport layer 7, and the layer was formed by dual vapor deposition of the compound (Compound 2-1) of Example 25 and the compound ETM-1 at a vapor deposition rate ratio of Compound 2-1/ETM-1=50/50. The characteristics of the organic EL device thus fabricated were measured in the atmosphere at an ordinary temperature. Table 1 summarizes the results of measurement of emission characteristics when applying a DC voltage to the fabricated organic EL device.

[Chemical Formula 246]

(2-1)

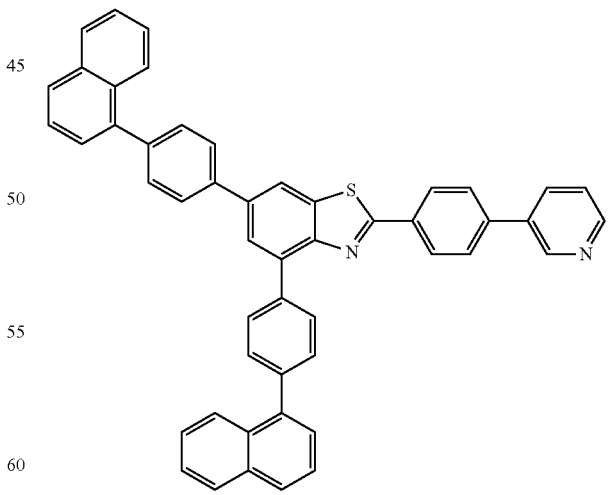

Example 42

An organic EL device was fabricated under the same conditions used in Example 29, except that the compound (Compound 1-1) of Example 1 was replaced with the compound (Compound 2-63) of Example 26 as the material of the hole blocking layer 6/the electron transport layer 7, and the layer was formed by dual vapor deposition of the compound (Compound 2-63) of Example 26 and the compound ETM-1 at a vapor deposition rate ratio of Compound 2-63/ETM-1=50/50. The characteristics of the organic EL device thus fabricated were measured in the atmosphere at an ordinary temperature. Table 1 summarizes the results of measurement of emission characteristics when applying a DC voltage to the fabricated organic EL device.

[Chemical Formula 247]

(2-63)

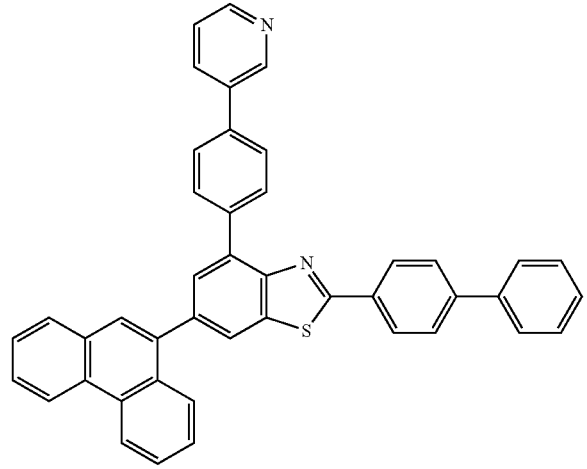

Comparative Example 1

For comparison, an organic EL device was fabricated under the same conditions used in Example 29, except that the compound (Compound 1-1) of Example 1 was replaced with the compound ETM-2 (refer to PTL 3, for example) of the structural formula below as the material of the hole blocking layer 6/the electron transport layer 7, and the layer was formed by dual vapor deposition of the compound ETM-2 of the structural formula below and the compound ETM-1 at a vapor deposition rate ratio of ETM-2/ETM-1=50/50. The characteristics of the organic EL device thus fabricated were measured in the atmosphere at an ordinary temperature. Table 1 summarizes the results of measurement of emission characteristics when applying a DC voltage to the fabricated organic EL device.

[Chemical Formula 248]

(ETM-2)

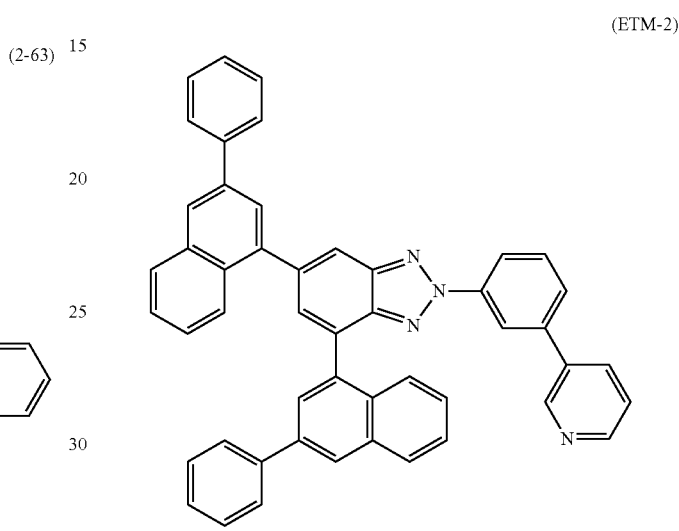

Table 1 summarizes the results of measurement of a device lifetime using the organic EL devices fabricated in Examples 29 to 42 and Comparative Example 1. The device lifetime was measured as a time elapsed until the emission luminance of 2,000 cd/m² (initial luminance) at the start of emission was attenuated to 1,900 cd/m² (corresponding to 95% when taking the initial luminance as 100%: Attenuation to 95%) when carrying out constant current driving.

TABLE 1

| | Hole blocking layer/ Electron transport layer | Voltage [V] (@10 mA/cm²) | Luminance [cd/m²] (@10 mA/cm²) | Luminous efficiency [cd/A] (@10 mA/cm²) | Power efficiency [1 m/W] (@10 mA/cm²) | Lifetime of device, attenulation to 95% |
|---|---|---|---|---|---|---|
| Example 29 | Compound 1-1/ETM-1 | 3.49 | 999 | 10.00 | 9.02 | 150 hours |
| Example 30 | Compound 1-2/ETM-1 | 3.60 | 1011 | 10.11 | 8.83 | 118 hours |
| Example 31 | Compound 1-6/ETM-1 | 3.55 | 994 | 9.93 | 8.78 | 108 hours |
| Example 32 | Compound 1-8/ETM-1 | 3.55 | 800 | 7.98 | 7.04 | 157 hours |
| Example 33 | Compound 1-112/ETM-1 | 3.40 | 975 | 9.75 | 9.02 | 174 hours |
| Example 34 | Compound 1-113/ETM-1 | 3.32 | 951 | 9.51 | 9.02 | 122 hours |
| Example 35 | Compound 1-118/ETM-1 | 3.37 | 1006 | 10.06 | 9.37 | 133 hours |
| Example 36 | Compound 1-119/ETM-1 | 3.49 | 1000 | 10.00 | 9.01 | 162 hours |
| Example 37 | Compound 1-120/ETM-1 | 3.47 | 971 | 9.71 | 8.80 | 211 hours |
| Example 38 | Compound 1-122/ETM-1 | 3.42 | 977 | 9.77 | 8.97 | 171 hours |

TABLE 1-continued

|  | Hole blocking layer/ Electron transport layer | Voltage [V] (@10 mA/cm$^2$) | Luminance [cd/m$^2$] (@10 mA/cm$^2$) | Luminous efficiency [cd/A] (@10 mA/cm$^2$) | Power efficiency [1 m/W] (@10 mA/cm$^2$) | Lifetime of device, attenulation to 95% |
|---|---|---|---|---|---|---|
| Example 39 | Compound 1-125/ETM-1 | 3.28 | 796 | 7.96 | 8.51 | 139 hours |
| Example 40 | Compound 1-131/ETM-1 | 3.40 | 962 | 9.62 | 8.88 | 147 hours |
| Example 41 | Compound 2-1/ETM-1 | 3.59 | 956 | 9.56 | 8.37 | 137 hours |
| Example 42 | Compound 2-63/ETM-1 | 3.54 | 838 | 8.38 | 7.43 | 110 hours |
| Comparative Example 1 | ETM-2/ETM-1 | 3.82 | 795 | 7.94 | 6.53 | 42 hours |

As shown in Table 1, the driving voltage on application of an electric current of a current density of 10 mA/cm$^2$ was 3.82 V for the organic EL device of Comparative Example 1 using the compound ETM-2 of the structural formula above, but was lowered to 3.28 to 3.60 V for the organic EL device of Examples 29 to 42. Also, the luminous efficiency was 7.96 to 10.11 cd/A for the organic EL device of Examples 29 to 42, which showed great improvements over the luminous efficiency 7.94 cd/A of the organic EL device of Comparative Example 1. Further, the power efficiency was 7.04 to 9.37 lm/W for the organic EL device of Examples 29 to 42, which showed great improvements over the power efficiency 6.53 lm/W of the organic EL device of Comparative Example 1. Table 1 also shows that the device lifetime (attenuation to 95%) was 108 to 211 hours for the organic EL devices in Examples 29 to 42, showing achievement of a far longer lifetime than 42 hours for the organic EL devices in Comparative Example 1.

Example 43

The glass substrate 1 on which ITO with a film thickness of 50 nm was formed was ultrasonically cleaned in isopropyl alcohol for 20 minutes, and then dried on a hot plate heated at 200° C. for 10 minutes. Thereafter, after performing a UV ozone treatment for 15 minutes, the glass substrate with ITO was installed in a vacuum vapor deposition apparatus, and the pressure was reduced to 0.001 Pa or lower. Subsequently, as the hole injection layer 3 covering the transparent anode 2, the compound HIM-1 of the structural formula above were formed in a film thickness of 5 nm. As the hole transport layer 4 on the hole injection layer 3, the compound HTM-1 of the structural formula above was formed in a film thickness of 65 nm. As the light emitting layer 5 on the hole transport layer 4, the compound EMD-1 of the structural formula above and the compound EMH-1 of the structural formula above were formed in a film thickness of 20 nm by dual vapor deposition at a vapor deposition rate that satisfies a vapor deposition rate ratio of EMD-1/EMH-1=5/95. As the hole blocking layer 6 on the light emitting layer 5, the compound (Compound 1-107) of Example 14 of the invention was formed in a film thickness of 5 nm. As the electron transport layer 7 on the hole blocking layer 6, the compound ETM-3 of the structural formula below and the compound ETM-1 of the structural formula below were formed in a film thickness of 25 nm by dual vapor deposition at a vapor deposition rate that satisfies a vapor deposition rate ratio of ETM-3/ETM-1=50/50. As the electron injection layer 8 on the electron transport layer 7, lithium fluoride was formed in a film thickness of 1 nm. Finally, aluminum was vapor deposited in a thickness of 100 nm to form the cathode 9. The characteristics of the organic EL device were measured in the atmosphere at ordinary temperature. Table 2 summarizes the results of measurement of emission characteristics when applying a DC voltage to the fabricated organic EL device.

[Chemical Formula 249]

(ETM-3)

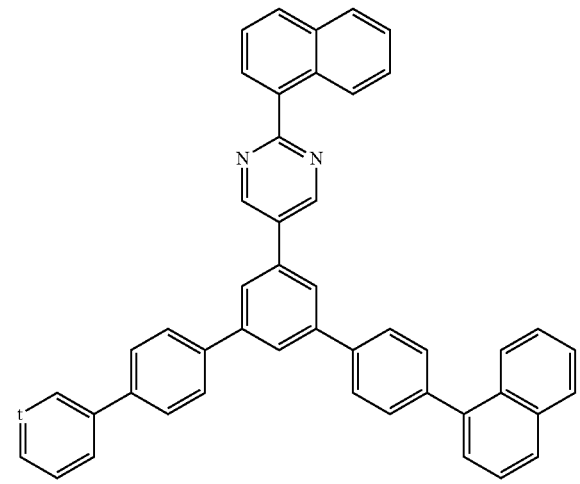

Comparative Example 2

For comparison, an organic EL device was fabricated under the same conditions used in Example 43, except that the compound (Compound 1-107) of Example 14 was replaced with the compound ETM-2 (refer to PTL 3, for example) of the structural formula above as the material of the hole blocking layer 6. The characteristics of the organic EL device thus fabricated were measured in the atmosphere at an ordinary temperature. Table 2 summarizes the results of measurement of emission characteristics when applying a DC voltage to the fabricated organic EL device.

Table 2 summarizes the results of measurement of a device lifetime using the organic EL devices fabricated in Example 43 and Comparative Example 2. The device lifetime was measured as a time elapsed until the emission luminance of 2,000 cd/m$^2$ (initial luminance) at the start of emission was attenuated to 1,900 cd/m$^2$ (corresponding to 95% when taking the initial luminance as 100%: Attenuation to 95%) when carrying out constant current driving.

TABLE 2

|  | Hole blocking layer | Voltage [V] (@10 mA/cm$^2$) | Luminance [cd/m$^2$] (@10 mA/cm$^2$) | Luminous efficiency [cd/A] (@10 mA/cm$^2$) | Power efficiency [1 m/W] (@10 mA/cm$^2$) | Lifetime of device, attenuation to 95% |
|---|---|---|---|---|---|---|
| Example 43 | compound 1-107 | 3.49 | 990 | 9.90 | 8.92 | 183 hours |
| Comparative Example 2 | ETM-2 | 3.60 | 837 | 8.37 | 7.31 | 44 hours |

As shown in Table 2, the driving voltage on application of an electric current of a current density of 10 mA/cm$^2$ was 3.60 V for the organic EL device of Comparative Example 2 using the compound ETM-2 of the structural formula above, but was lowered to 3.49 V for the organic EL device of Example 43. Also, the luminous efficiency was 9.90 cd/A for the organic EL device of Example 43, which showed great improvements over the luminous efficiency 8.37 cd/A of the organic EL device of Comparative Example 2. Further, the power efficiency was 8.92 lm/W for the organic EL device of Example 43, which showed great improvements over the power efficiency 7.31 lm/W of the organic EL device of Comparative Example 2. Table 2 also shows that the device lifetime (attenuation to 95%) was 183 hours for the organic EL device in Example 43, showing achievement of a far longer lifetime than 44 hours for the organic EL device in Comparative Example 2.

As described above, the organic EL device of the present invention can achieve an excellent luminous efficiency, an excellent power efficiency and a long lifetime compared to the organic EL device using the compound ETM-2 of the structural formula above used as a general electron transport material.

INDUSTRIAL APPLICABILITY

The compounds having a specific fused-azole ring structure have a high electron injection performances, an excellent hole blocking ability, and a stable thin-film state, and are desirable for organic EL devices. The organic EL device produced by using the compounds can have high efficiency, and a low driving voltage, and can thus have improved durability. There are potential applications for, for example, home electronic appliances and illuminations.

REFERENCE SIGNS LIST

1 Glass substrate
2 Transparent anode
3 Hole injection layer
4 Hole transport layer
5 Light emitting layer
6 Hole blocking layer
7 Electron transport layer
8 Electron injection layer
9 Cathode

The invention claimed is:

1. A compound having a fused-azole ring structure, wherein the compound is represented by the formula:

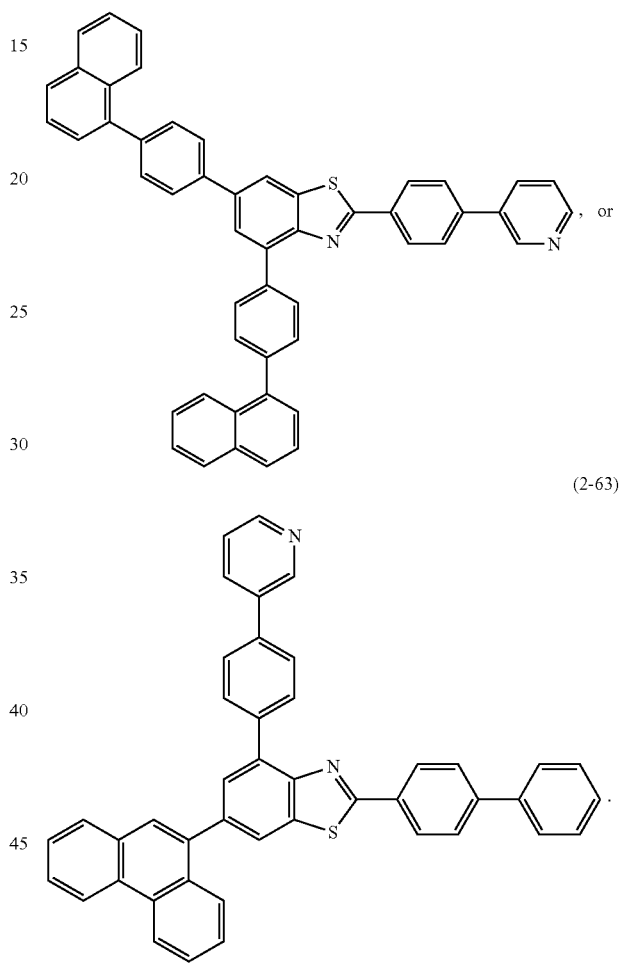

2. An organic electroluminescent device comprising a pair of electrodes, and one or more organic layers sandwiched between the pair of electrodes, wherein the compound having a fused-azole ring structure according to claim 1 is used as a constituent material of at least one organic layer.

3. The organic electroluminescent device according to claim 2, wherein the organic layer using the compound having a fused-azole ring structure is an electron transport layer.

4. The organic electroluminescent device according to claim 2, wherein the organic layer using the compound having a fused-azole ring structure is a hole blocking layer.

5. The organic electroluminescent device according to claim 2, wherein the organic layer using the compound having a fused-azole ring structure is a light emitting layer.

6. The organic electroluminescent device according to claim 2, wherein the organic layer using the compound having a fused-azole ring structure is an electron injection layer.

* * * * *